US 6,395,891 B1

(12) United States Patent
Karn et al.

(10) Patent No.: US 6,395,891 B1
(45) Date of Patent: May 28, 2002

(54) METHODS AND COMPOSITIONS FOR COMBATING HIV INFECTION

(75) Inventors: Jonathan Karn, Cambridge; Rodney Warren Zemmel, London; Peter Jonathan Gasking Butler, Cambridge; Roger K. Craig, Cheshire; Alistair Simpson Irvine, Derbyshire, all of (GB)

(73) Assignee: RiboTargets Limited, Cambridge (GB)

( * ) Notice: Subject to any disclaimer, the term of this patent is extended or adjusted under 35 U.S.C. 154(b) by 0 days.

(21) Appl. No.: 09/150,812

(22) Filed: Sep. 11, 1998

Related U.S. Application Data

(62) Division of application No. 08/839,624, filed on Apr. 15, 1997, now Pat. No. 6,225,045.
(60) Provisional application No. 60/017,268, filed on May 13, 1996.

(30) Foreign Application Priority Data

Apr. 15, 1996 (GB) .............................................. 9607819

(51) Int. Cl.$^7$ .............................................. C07H 21/04
(52) U.S. Cl. ........................ 536/24.1; 536/23.1; 435/5
(58) Field of Search ............................. 435/5; 536/24.1, 536/23.1

(56) References Cited

FOREIGN PATENT DOCUMENTS

WO    WO 92/05195    4/1992

OTHER PUBLICATIONS

Bartel et al., 1991, HIV–1 Rev regulation involves recognition of non–Watson–Crick base pairs in viral RNA, *Cell*, 67: 529–236.

Bogerd et al., 1995, Identification of a novel cellular co–factor for the Rev/Rex class of retroviral regulatory proteins, *Cell*, 82: 485–494.

Cochrane et al., 1990, Specific interaction of the human immunodeficiency virus Rev protein with a structured region in the env mRNA, *Proc. Natl. Acad. Sci. U.S.A.*, 87: 1198–1202.

Daly et al., 1989, Specific binding of HIV–1 recombinant Rev protein to the Rev–responsive element in vitro, *Nature*, 342: 816–819.

Dayton et al., 1989, Functional analysis of CAR, the target sequence for the Rev protein of HIV–1, *Science*, 246: 1625–1629.

Dayton et al., 1992, Extensive sequence–specific information throughout the CAR/RRE, the target sequence of the human immunodeficiency virus type 1 rev protein, *J. Virol.*, 66: 1139–1151.

Emerman et al., 1989, The rev gene product of the human immunodeficiency virus affects envelope specific RNA localization, *Cell*, 57: 1155–1165.

Fischer et al., 1994, Evidence that HIV–1 Rev directly promotes the nuclear export of unspliced RNA, *EMBO J.*, 13: 4105–4112.

Fischer et al., 1995, The HIV–1 Rev activation domain is a nuclear export signal that accesses an export pathway used by specific cellular RNAs, *Cell*, 82: 475–483.

(List continued on next page.)

*Primary Examiner*—Laurie Scheiner
*Assistant Examiner*—Jeffrey S. Parkin
(74) *Attorney, Agent, or Firm*—Kathleen Madden Williams; Palmer & Dodge LLP

(57) ABSTRACT

The invention relates to an isolated nucleic acid comprising two operatively linked binding sites for HIV Rev protein, the sites comprising a nucleation motif and an oligomerization motif, wherein the nucleic acid binds Rev protein monomers with a higher degree of cooperativity than wild-type RRE.

17 Claims, 22 Drawing Sheets

OTHER PUBLICATIONS

Giver, et al., 1993, Selective optimization of the Rev–binding element of HIV–1, *Nucleic Acids Research*, 21(23) 5509–5516.

Heaphy et al., 1990, HIV–1 regulator of virion expression (Rev) protein binds to an RNA stem–loop structure located within the Rev–response element region, *Cell*, 60:685–693.

Heaphy et al., 1991, Human immunodeficiency virus type 1 regulator of virion expression, Rev, forms nucleoprotein filaments after binding to a purine–rich "bubble" located within the Rev–responsive region of viral RNA, *Proc. Natl. Acad. Sci. U.S.A.*, 88: 7366–7370.

Holland et al., 1992, A specific sequence with a bulged guanosine residue(s) in a stem–bulge–stem structure rev–responsive element RNA is required for trans–activation by human immunodeficiency virus type 1 rev, *J. Virol.*, 66: 3699–3706.

Huang et al., 1991, Minimal Rev–response element for type 1 human immunodeficiency virus, *J. Virol.*, 65: 2131–2134.

Iwai et al., 1992, Recognition of the high affinity binding site in rev–responsive element RNA by the human immunodeficiency virus type–1 rev protein, *Nucl. Acids Res.*, 20: 6465–6472.

Jensen, K.B. et al., 1995, Using in vitro selection to direct the covalent attachment of the human immunodeficiency virus type 1 Rev protein to high–affinity RNA ligands, *Proc. Natl. Acad. Sci. U.S.A.*, 92: 12220–12224.

Kimura, et al., 1994, Interaction with the rev response element along an extended stem I duplex structure is required to complete human immunodeficiency virus type 1 rev–mediated trans activation in vivo, *J. of Biochem.*, 115, 945–952.

Kjems et al., 1991, Structural analysis of the interaction between the human immunodeficiency virus Rev protein and the Rev–resonse element, *Proc. Natl. Acad. Sci. U.S.A.*, 88: 683–687.

Kjems et al., 1992, Specific binding of a basic peptide from HIV–1 Rev, *EMBO J.*, 11: 1119–1129.

Malim et al., 1989a, Functional dissection of the HIV–1 Rev trans–activator: Derivation of a trans–dominant repressor of Rev function, *Cell*, 58: 205–214.

Malim et al., 1989b, The HIV–1 Rev trans–activator acts through a structured target sequence to activate nuclear export of unspliced viral mRNA, *Nature*, 338: 254–257.

Malim et al., 1990, HIV–1 structural gene expression requires binding of the Rev trans–activator to its RNA target sequence, *Cell*, 60: 675–683.

Malim et al., 1991, Mutational definition of the human immunodeficiency virus type 1 Rev activation domain, *J. Virol.*, 65: 4248–4254.

Malim and Cullen, 1991, HIV–1 structural gene expression requires the binding of multiple Rev monomers to the RRE: Implications for HIV–1 latency, *Cell*, 65: 241–248.

Malim and Cullen, 1993, Rev and the fate of pre–mRNA in the nucleus: Implications for the regulation of RNA processing in eukaryotes, *Mol. Cell. Biol.*, 13: 6180–6189.

Mann et al., 1994, A molecular rheostat: co–operative Rev binding to Stem I of the Rev–response element modulates human immunodeficiency virus type–1 late gene expression, *J. Mol. Biol.*, 241: 193–207.

Meyer and Malim, 1994, The HIV–1 rev trans–activator shuttles between the nucleus and the cytoplasm, *Genes Dev.*, 8: 1538–1547.

Olsen et al., 1990, Secondary structure is the major determinant for interaction of HIV rev protein with RNA, *Science*, 247: 845–848.

Powell et al., 1995, Sequence specificity in the higher order interaction of the Rev protein of HIV–1 with its target sequence, the RRE, *J. Acq. Imm. Def. Syndr. and Hum. Retrovir.*, 10: 317–323.

Pritchard et al., 1994 Methylphosphonate mapping of phosphate contacts critical for RNA recognition by the human immunodeficiency virus tat and rev proteins, *Nucleic Acids Res.*, 22: 2592–2600.

Rosen et al., 1988, Intragenic cis–acting art–responsive sequences of the human immunodeficiency virus, *Proc. Natl. Acad. Sci. U.S.A.*, 85: 2071–2075.

Stutz et al., 1995, Identification of a novel nuclear pore–associated protein as a functional target of the HIV–1 Rev protein in yeast, *Cell*, 82: 495–506.

Sun, et al., 1995, Resistance to human immunodeficiency virus type 1 infection conferred by transduction of human peripheral blood lymphocytes with ribozyme, antisense, or polymeric trans–activation response element contructs, *Proceedings of the National Academy of Sciences*, 92, 7272–7276.

Tiley et al., 1992, Identification of a high–affinity RNA–binding site for the human immunodeficiency virus type 1 rev protein, *Proc. Natl. Acad. Sci. U.S.A.*, 89: 758–762.

Wen et al., 1995, Identification of a signal for rapid export of proteins from the nucleus, *Cell*, 82: 463–473.

Wolff et al., 1995, Nucleocytoplasmic transport of the rev protein of human immunodeficiency virus type 2 is dependent of the activation domain of the protein, *Exp. Cell Res.*, 217: 31–41.

Zapp and Green, 1989, Sequence–specific binding by the HIV–1 rev protein, *Nature*, 342: 714–716.

Zapp et al., 1991 Oligomerization and RNA binding domains of the type 1 human immunodeficiency virus rev protein: A dual function for an arginine–rich binding motif, *Proc. Natl. Acad. Sci. U.S.A.*, 88: 7734–7738.

Zemmel, R. et al., 1996, Flexible regions of RNA structure facilitate co–operative rev assembly on the rev–response element, *J. Molecular Biology.*, 258(5): 763–777.

FIG. 1

| FIG. 1A |
|---|
| FIG. 1B |

FIG. 1B

RNA structures

RWZ1

RWZ2

RNA structures

RWZ2

RWZ5

RWZ6

RNA structures

RWZ7

RWZ8

RWZ9

RNA structures

RWZ1

RWZ2

RWZ15

RNA structures

RWZ1

RWZ10

RWZ11

RWZ12

RNA structures

RWZ2

RWZ13

RWZ6

RWZ14

HIV-2 TAR

```
       G  G
      U    G
       C  A
       CG
       CG
       GU
       AU
       GC
      U
      U
       AU
       GC
       AU
       C
       GC
       GC
       UA
       CG
       GC
          A
       GC
       AU
       G
      A
       G   A
       G
       CG
       GC
       UA
       CG
     5'    3'
```

METHODS AND COMPOSITIONS FOR COMBATING HIV INFECTION

RELATED APPLICATIONS

This application claims priority as a divisional application to U.S. patent application Ser. No. 08/839,624, filed Apr. 15, 1997, now U.S. Pat. No. 6,225,045 which claims priority to U.S. Provisional Application 60/017,268, filed May 13, 1996.

FIELD OF THE INVENTION

This invention relates to inhibition of replication of human immunodeficiency virus (HIV).

BACKGROUND OF THE INVENTION

HIV is the causative agent of acquired immunodeficiency syndrome (AIDS). The trans-activation region (TAR) and the Rev-response element (RRE) (Rosen et al., 1988; Dayton et al., 1989; Malim et al., 1990) of HIV are found in unspliced or partially spliced HIV mRNA introns. During replication of HIV, the RRE and TAR RNAs interact with specific HIV proteins. The RRE is recognized by the HIV protein Rev (Daly et al., 1989; Zapp & Green, 1989; Cochrane et al., 1990; Heaphy et al., 1930; Malim et al., 1990) which stimulates mRNA export from the nucleus (Emerman et al., 1989; Malim et al., 1990; Malim & Cullen 1993; Fischer et al., 1994; Meyer & Malim, 1994; Bogerd et al., 1995; Stutz et al., 1995) via the formation of a Rev/RRE complex which displays a nuclear export signal that is essential for Rev-mediated export of RNA from the nucleus and also for Rev shuttling (Malim et al., 1991; Fischer et al., 1994; Meyer & Malim, 1994; Fischer et al., 1995; Stutz et al., 1995; Wen et al., 1995; Wolff et al., 1995). The Rev/RRE interaction regulates the cytoplasmic accumulation of HIV genomic and structural mRNAs and is therefore essential if the virus is to propagate.

The RRE contains a series of stem-loop structures protruding from a long central stem, known as Stem I (Dayton et al., 1989; Malim et al., 1989b; Dayton et al., 1992; Mann et al., 1994), as shown in FIG. 1 (RRE-WT)[SEQ ID NO: 1]. At the base of Stem IIb is a high-affinity Rev-binding motif which is recognized by a single Rev protein with a $K_d$ of approximately 1nM (Bartel et al., 1991; Heaphy et al., 1991; Iwai et al., 1992; Kjems et al., 1992; Tiley et al., 1992). This high-affinity motif is a purine-rich bubble stabilized by non-Watson-Crick G•A and G•G base pairs (Heaphy et al., 1991; Bartel et al., 1991; Iwai et al., 1992; Pritchard et al., 1994). Together with a bulged-out uridine nucleotide, these non-Watson-Crick base pairs open the major groove of the mRNA duplex and permit the recognition of functional groups on the two base pairs either side of the bulged region inside the widened major groove. In addition to these base-specific contacts, phosphate contacts are made around the bubble as well as with base-paired nucleotides further away from the bubble (Iwai et al., 1992; Kjems et al., 1992; Pritchard et al., 1994).

Mutational analysis of the RRE has shown that the high-affinity interaction with a single Rev protein is necessary, but not sufficient, for Rev activity in vivo (Dayton et al., 1989; Malim et al., 1989b; Malim et al., 1990; Olsen et al., 1990; Bartel et al., 1991; Huang et al., 1991; Dayton et al., 1992; Holland et al., 1992; Mann et al., 1994). For full activity, further Rev monomers must be able to oligomerize along stem I of the RRE (Heaphy et al., 1990, 1991; Malim & Cullen, 1991; Mann et al., 1994). Truncations of Stem I that do not affect the high-affinity motif reduce Rev responses by removing additional potential binding sites for Rev monomers, with the longest truncations producing the greatest losses of activity (Mann et al., 1994). Similarly, mutations in the Rev protein that block oligomerization along the RNA stem result in an inactive protein (Malim & Cullen, 1991; Zapp et al., 1991).

It has been suggested that up to twelve Rev monomers in total can bind to each wild-type RRE (Mann et al., 1934). The high-affinity motif is not the sole Rev binding site on the RRE, however, unless a monomer is bound to the high-affinity motif, the oligomerization of Rev cannot take place. The binding of a single Rev to the high-affinity motif facilitates the binding and co-operative oligomerization of additional Rev monomers along the RRE (Iwai et al., 1992; Mann et al., 1994), with neighboring Rev monomers in contact with one another (Mann et al., 1994).

Various models have been proposed as to the mechanism by which Rev oligomerization is achieved. Kjems et al. (1991) suggested that Rev monomers bind to a variety of sequence-specific sites in the RRE. Zapp et al. (1991) argued that Rev binds to the RRE high-affinity site as a pre-existing tetramer. Malim & Cullen (1991) ascribed the oligomerization solely to protein/protein interactions between neighboring Rev monomers, and Tiley et al. (1992) reached the same conclusion. Powell et al. (1995) refined this view, believing that sequence-specific information in the RNA can exert a subtle influence on higher-order binding, but maintain that protein/protein interactions are the major determinant directing oligomerization.

Disruption of the natural Rev/RRE interaction via mutation of the natural sequences has been explored in the prior art as a potential avenue to the use of altered Rev or RRE molecules in anti-HIV therapy. Transdominant Rev mutants which retain the RRE-binding features of wild-type Rev but which are defective in certain other features have been described(e.g. Malim et al., 1989a; Malim et al., 1991; Bogerd et al., 1995).

Harada et al. (1996) relates to in vivo methods for selecting short peptides which bind Rev.

Jensen, K. B. et ,a. (1995) disclose chemically modified RNA sequences (i.e., containing 5-iodouridine) which bind Rev in vitro with higher affinity than the RRE and which are able to crosslink with Rev at a 1:1 ratio. These are postulated as potential suicide ligands for in vivo disease inhibition, however, non-specific interactions with chemically reactive bases cannot be ruled out in an in vivo situation.

WO92/05195 discloses molecules which mimic the high-affinity binding site of the native RRE in order to act as competitive inhibitors, thus sequestering free Rev protein and preventing it from interacting with those mRNAs which contain the RRE. These molecules contain a greater number of Rev binding sites than are contained in viral RRE-containing mRNAs.

One object of the invention is to provide nucleic acid molecules which inhibit HIV replication.

Another object of the invention is to provide a nucleic acid decoy which binds HIV Rev protein so as to inhibit HIV infection.

Another object of the invention is to provide a nucleic acid decoy which binds HIV Rev protein with greater co-operativity than the wild-type RRE.

SUMMARY OF THE INVENTION

The invention is based on the unexpected discovery that model RREs comprising a high-affinity binding-motif flanked by perfect duplex RNA can only bind a monomer of Rev, and that disruptions to the RNA duplex in the vicinity of the high-affinity motif are necessary to permit the binding of additional Rev monomers. It also has been discovered that each disruption seems to allow the binding of an additional Rev monomer.

Therefore, according to the present invention there is provided an isolated nucleic acid comprising two or more operatively linked binding sites for HIV Rev protein, the sites comprising at least one nucleation motif and at least one oligomerization motif, wherein the nucleic acid binds Rev protein monomers with a higher degree of co-operativity than wild-type RRE.

As used herein, the term "operatively linked" means that oligomerization of a second HIV Rev protein along a nucleic acid molecule of the invention is initiated by the sequence-specific binding of a single Rev monomer at a nucleation motif. Therefore, in order for binding of a second Rev protein to occur, the binding of a first Rev protein at a high affinity site (i.e., a nucleation motif) must occur.

As used herein, the term "nucleation motif" refers to a nucleic acid binding site for Rev protein, wherein the Rev occupancy of the binding site is independent of the presence of any other bound Rev monomers.

The term "oligomerization motif" refers to a nucleic acid binding site for Rev protein, wherein the Rev occupancy of the binding site requires at least one Rev monomer to have already bound to an operatively linked Rev-binding site.

The nucleation motif is recognized by Rev in a sequence-specific manner. The nucleation motif may comprise a sequence of the following generic structural formula:

—EG RN AYP—

—FCR'(N')$_n$GR"Q— where n=0 or 1; Y & R" are, respectively, a pyrimidine and purine; E & F are nucleotides which can form a base pair; P & Q are nucleotides which can form a base pair; R and R' is a purine; and N and N' is any nucleotide.

The nucleation motif is preferably the RNA minimal Rev binding motif present in the native RRE, shown boxed in FIG. 1 [SEQ ID NO: 1; nucleotides 103–108 and 127–133].

As used herein, the term "isolated nucleic acid" refers to nucleic acids which are produced by chemical synthesis or utilizing nucleotide polymerases, in vivo or ex vivo, and refers to a plurality of joined nucleotide units, or nucleotide analogue units, but does not include a nucleic acid in its natural environment. Thus nucleic acids of the invention may contain any of the five naturally-occurring bases found in DNA and RNA, and also may contain alternative bases such as inosine, or purine or pyrimidine bases not normally found in nature, or modifications to the cyclofranose portions of bases. Isolated nucleic acids of the invention may contain some altered inter-sugar linkages, as exemplified by phosphorothioate and other sulphur-containing species well-known in the art; altered sugar moieties, such as those with substitutions at their 2' position. Such 2' substituents might be OH, SH, F, OCH$_3$ groups.

It is preferred that the nucleic acid is RNA. This may be prepared by direct transcription from a coding or complementary DNA sequence in vitro or in vivo, or by chemical synthesis. RNAs according to the invention are termed RNA decoys.

The oligomerization motifs preferably comprise a double-stranded nucleic acid in which there is a small region of disruption of the duplex structure. The term "disruption" refers to any feature in the nucleic acid sequence which results in a bulge in the duplex structure, and is further defined hereinbelow.

Preferably, the nucleic acid has a single nucleation motif and preferably one or more oligomerization motifs. The oligomerization motifs may be upstream or downstream of the nucleation motif, and may be the same sequence or a different sequence of nucleotides.

A nucleic acid molecule may also be provided which contains two or more nucleation motifs, which may be the same or different in sequence, some or all of which may be functionally linked to one or more oligomerization motifs.

The invention also encompasses a composition comprising an isolated nucleic acid as described above in combination with another anti-HIV agent, for example, a Tat decoy.

The invention also encompasses an assay for the oligomerization of Rev using a nucleic acid template as described herein, and also encompasses an assay for screening for a candidate inhibitor of the oligomerization interaction between Rev and a nucleic acid template.

The invention thus also encompasses a screening assay for inhibition of Rev binding to a nucleic acid substrate, comprising detecting a decrease in the amount of a complex comprising Rev and a nucleic acid according to the invention in the presence of a candidate inhibitor relative to the absence of the candidate inhibitor.

The invention also encompasses an assay for identifying a candidate inhibitor of HIV, comprising contacting a nucleic acid according to the invention with Rev protein in the presence of a candidate inhibitor under conditions such that a complex is permitted to form between the nucleic acid and Rev protein, and determining the amount of complex formed in the presence of the candidate inhibitor, wherein a determination of a decrease in the amount of complex formed in the presence of the candidate inhibitor relative to its absence is indicative of inhibition.

The invention thus also encompasses an assay for identifying a candidate inhibitor of HIV, comprising providing a nucleic acid according to the invention, Rev protein, and a candidate inhibitor, detecting formation of a complex between the nucleic acid and Rev protein in the presence and absence of the candidate inhibitor, and comparing the detected formation of complex in the presence and absence of the candidate inhibitor, wherein a difference in the detected formation of complex in the presence and absence of the candidate inhibitor is indicative of inhibition.

The invention also encompasses nucleic acid templates that may form part of an assay, or assay kit, for use in the detection of oligomerization of Rev on a nucleic acid template.

The invention thus also encompasses a kit for identifying candidate inhibitor of Rev binding to a nucleic acid molecule, comprising a nucleic acid according to the invention and packaging means therefor.

The invention also encompasses a vector which encodes an isolated nucleic acid as described herein.

Preferably, the vector is targeted to cells susceptible to infection by HIV.

In the embodiment of the invention wherein the vector is targeted to cells susceptible to infection by HIV, the vector may be targeted using a vector delivery system which specifically targets cell-specific antigens found on susceptible cells, or which targets progenitor cells so that the delivered DNA is subsequently expressed in cells of a particular lineage susceptible to infection by the virus.

The vector also may encode one or more additional anti-HIV agents, such as antisense nucleic acids or ribozymes. In such a case, the anti-HIV agents may be part of the same species or may be a different species of HIV, such as HIV-1, HIV-2, HIV-3, etc.

Alternatively, the vectors may be suitable for producing nucleic acids according to the invention which may then be purified and subsequently administered to patients.

The invention also encompasses a method of transfecting a cell, comprising transfecting a target cell with a vector according to the invention.

The invention also encompasses a host cell transformed with a vector according to the invention.

The invention also encompasses a delivery system comprising a nucleic acid molecule of the invention and means to deliver the nucleic acid molecule to a target cell.

In another embodiment of the invention, tissue-specific control sequences and tissue-specific delivery systems may be combined to provide two levels of specificity to target the therapeutic nucleic acid molecule to the appropriate cells.

The invention also encompasses a nucleic acid molecule according to the invention for use in therapy, and administration of such nucleic acid molecules for treatment of HIV infection.

Particular therapeutic uses include the treatment of a patient infected with HIV and the prophylactic treatment of individuals at risk of HIV infection. Preferably, the nucleic acid molecules may be used in association with other therapeutic agents or pharmaceuticals.

The invention also encompasses the use of a nucleic acid molecule according to the invention in the preparation of a medicament for the treatment or prophylaxis of HIV infection.

The invention also encompasses a method of treating an HIV-infected patient, comprising administering an effective amount of a nucleic acid molecule according to the invention.

Preferably, the method also comprises administering one or more additional anti-HIV agents.

The invention also encompasses a method of protecting individuals at risk of HIV infection, comprising administering an effective prophylactic amount of a nucleic acid of the invention.

The above-described method may also comprise the administration of one or more additional prophylactic agents.

The invention also encompasses a pharmaceutical composition comprising a nucleic acid according to the invention admixed with a pharmaceutically acceptable carrier.

Preferably, the composition further comprises one or more other antiviral agents.

The invention also encompasses a process for producing a pharmaceutical composition according to the invention comprising bringing a nucleic acid molecule of the present invention into association with a pharmaceutically acceptable carrier.

Further features and advantages of the invention will become more fully apparent in the following description of the embodiments and drawings thereof, and from the claims.

BRIEF DESCRIPTION OF THE DRAWINGS

Figure 1B:
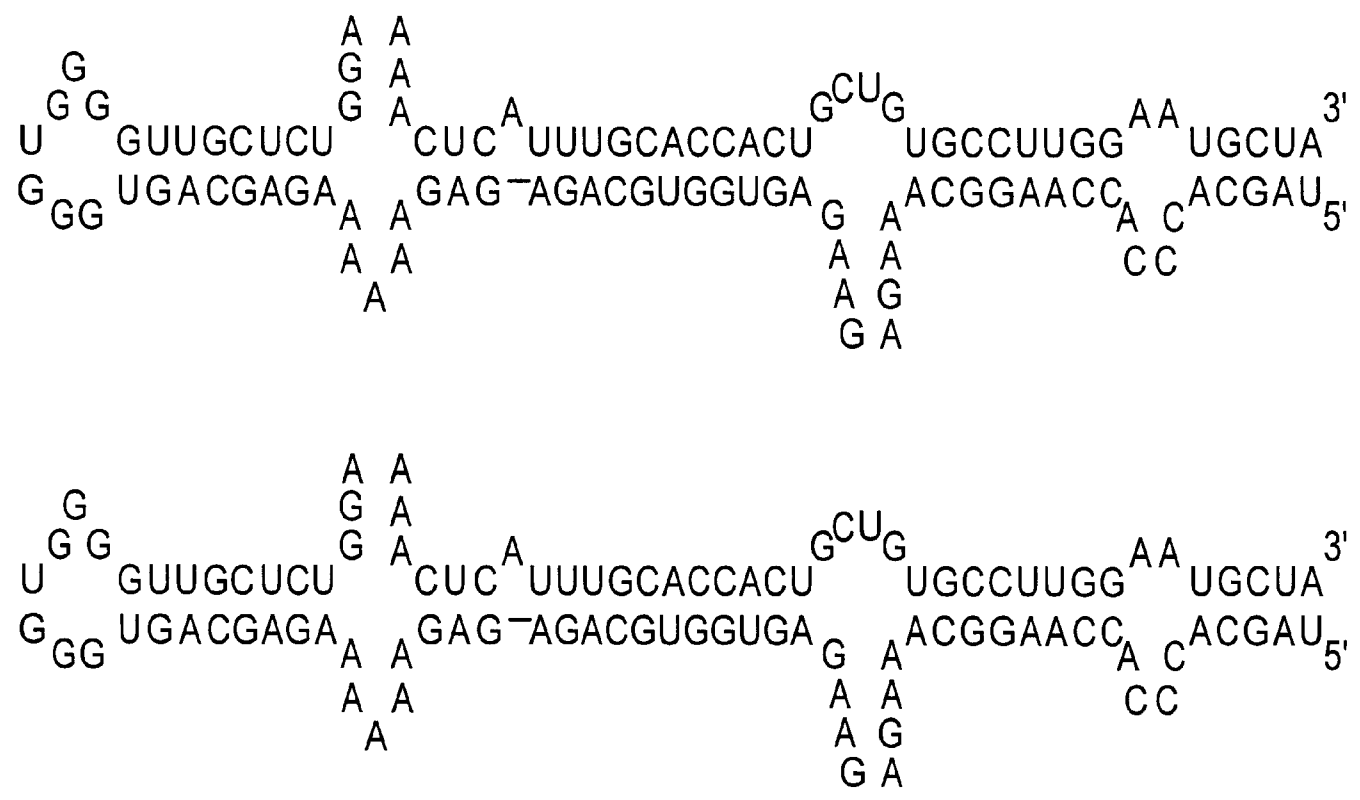

FIG. 1 shows the structure of the 351 nt wild-type RRE (RRE-WT), [SEQ ID NO: 1] an RRE-analogue (RRE-S), [SEQ ID NO: 2] and of the high-affinity nucleation motif. The structures given are predicted to be the most stable (Jaeger et al., 1989a,b; Zuker, 1989).

DESCRIPTION

Figure 2A:
FIG. 2 shows the predicted secondary structures of model substrates RWZ1 [SEQ ID NO: 3] and RWZ2 [SEQ ID NO: 4] along with the results from gel-retardation assays using these substrates.

The contents of all references referred to herein are incorporated by reference in their entirety.

The HIV Rev/PRE interaction involves two well-documented distinct steps, namely an initial nucleation event, involving a sequence-specific interaction at the high-affinity motif of RRE, followed by co-operative oligomerization along the RRE, involving a series of sequence-non-specific lower-affinity interactions, the requirements of which have not been well-understood. The invention is based on the observation that the initial high-affinity Rev binding site is insufficient to initiate Rev oligomerization, and that sequences bordering and outside the high-affinity site make a contribution to Rev assembly.

The invention provides nucleic acid decoys which bind HIV Rev monomers with a higher degree of co-operativity than the wild-type RRE. These nucleic acids possess anti-HIV activity in cell culture, and are useful according to the invention as anti-HIV agents in gene therapy.

The invention also encompasses nucleic acid templates that may form part of an assay, or assay kit, for use in the detection of oligomerization of Rev on a nucleic acid template.

The invention provides nucleic acid molecules which include two or more (for example, up to ten or even twenty) binding sites for HIV Rev protein, which sites are operatively linked, at least one site comprising a Rev nucleation motif and at least one other site comprising a Rev oligomerization motif, wherein the nucleic acid molecule binds Rev protein monomers better than (that is, with a higher degree of co-operativity) than wild-type RRE. Methods for determining the degree of cooperative binding of Rev to a given RNA are described herein.

Nucleic acid molecules of the invention are either synthetic or in vitro or in vivo synthesized nucleic acids, preferably RNAs. In a preferred embodiment of the invention, the nucleic acid molecules may be encoded by a vector, wherein the term "vector" signifies a nucleic acid which is capable of transferring DNA to a host cell. Preferably this DNA is capable of expressing an RNA according to the invention.

Alternatively, Where the nucleic acid of the invention is an RNA, the RNA may be isolated from in vitro or ex vivo cells which are transfected with a DNA encoding the RNA, and administered to a patient in need thereof, as described herein. The nucleic acid molecules described herein and are prepared and administered as described below.

Mechanism of Action

In investigating the nature of these Rev/RRE interactions, it is observed that Rev oligomerization along the wild-type viral RRE is not a fully co-operative process. If full co-operativity were evident, at limiting concentrations of Rev, the Rev monomers would fully coat a limited number of RRE templates by a process of co-operative saturation. Instead, it is observed that Rev monomers distribute evenly between a large number of RRE templates and binding sites are filled up according to the prevailing Rev concentration. Since more than six Rev monomers must bind to the RRE before a maximal Rev response is obtained (Mann et al., 1994), this means that at low Rev concentrations there will be no response. If the Rev/RRE interactions were fully co-operative, however, the increasing Rev concentration would result in the saturation of individual RREs, thus allowing a steady leakage of mRNAs from the nucleus even at the lowest Rev concentrations as each RRE is coated. The limited co-operativity of Rev oligomerization on the wild-type RRE therefore allows the degree of oligomerization along the RRE to give a sensitive indication of the intracellular concentration of Rev (Mann et al., 1994).

It is postulated that the Rev/RRE interaction achieves two essential functions, namely the assembly of Rev monomers along a mRNA molecule, without which the mRNA would not be exported from the nucleus, and the measurement of intercellular Rev concentration, which serves as an indicator of progress through HIV's life-cycle. It is believed that during the evolution of these two functions, a compromise had to be made between the structural features of the RRE essential for each function. By minimizing the features of the RRE which are believed to be responsible for its concentration measurement activity, it has been possible to construct enhanced RRE decoys which bind Rev with a higher degree of co-operativity than wild-type RRE and which therefore sequester Rev more efficiently than simple copies of features from the native RRE. This allows sequestration to move away from a simple population-based approach to a more useful approach relying on an understanding of the nature of the interaction between Rev and the RRE. With a high degree of co-operativity, these nucleic acid molecules will thus sequester more Rev monomers than the low co-operativity distributive structures.

Determining the Structural Features of a Nucleic Acid Molecule of the Invention.

The following experiments describe testing of nucleation and oligomerization motifs which constitute nucleic acid molecules according to the invention, and mutants thereof which lack nucleation and oligomerization activities and therefore inactive for therapeutic purposes but which serve as control molecules in assays for Rev oligomerization, and the establishment of the therapeutic potential of active nucleic acid molecules according to the invention.

Results of experiments described below provide the following guidelines for determining whether a nucleic acid molecule which fits the sequence requirements provided herein for preferred nucleic acid molecules of the invention fall within the functional parameters of nucleic acid molecules useful in the invention.

First, nucleic acid molecules of the invention must possess at last two HIV Rev binding sites, one of which is a nucleation motif and the other of which is an oligomerization motif. These two sites are "operatively linked", which means that oligomerization of HIV Rev protein along a nucleic acid molecule of the invention is initiated by the sequence-specific binding of a single Rev monomer at a nucleation motif. Therefore, in order for binding of a second Rev protein to occur, the binding of a first Rev protein at a high affinity site must occur.

Second, nucleic, acid molecules of the invention must possess a disruption in the RNA duplex structure which forms the Rev binding sites according to the invention. It is observed hereinbelow that if the nucleation motif is inserted into a stretch of RNA having perfect duplex structure, only a single Rev monomer binds and oligomerization does not proceed. However, the insertion of a bulge on either strand to disrupt the duplex structure permits the co-operative incorporation of a second Rev molecule.

The term "disruption" refers to any feature in the duplex wherein at least one nucleotide subunit on either strand of the nucleic acid is unable to form a Watson-Crick base pair with another nucleotide. The term "disruption" also refers to any modification to either of the nucleic acid strands which introduces a flexible bend into the duplex's double-helix structure, which produces local distortion resulting in the opening of the double-helix's major groove (Weeks & Crothers, 1991; Puglisi et al., 1992; Battiste et al., 1994; Peterson et al., 1994a,b; Aboul-ela et al., 1995), or which mimics the three-way junction with stem IIc found in the wild-type RRE.

The disruption may be, for example, the insertion or deletion of a single nucleotide into one strand of perfect duplex RNA resulting in a "bulge" of a single nucleotide, or it might be a larger insertion. Larger insertions may be dinucleotides, trinucleotides, or oligonucleotides, which may inherently possess independent secondary structure. Additionally, any such disruption may be on either strand of the double-stranded nucleic acid. Other disruptions might include the insertion of a non-Watson-Crick base pair into the duplex structure, giving rise to a double stranded "bubble".

Third, additional disruptions of the RNA duplex structure of a nucleic acid molecule of the invention provide for binding of additional Rev monomers which oligomerize with a higher degree of co-operativity than they do along the native RRE. As used herein, a "higher" degree of co-operativity refers to a higher co-operativity factor ($\omega$)), as calculated hereinbelow, wherein the baseline degree of co-operativity is, e.g., for RWZ1[SEQ ID NO: 3], 4.6, and a higher degree of co-operativity is, e.g., 29.4–133, or at least 6.5-fold–30-fold higher than baseline co-operativity.

Fourth, the optimum spacing between any given pair of Rev-binding motifs to give maximum co-operativity can be easily determined by routine experimentation. The spacing between the disruptions in adjacent oligomerization motifs may be the same sequence or a different nucleic acid sequence, and these may be the same length or a different length from the spacing between the disruptions in the nucleation motif and its neighboring oligomerization motif. It is preferred that the positions of the oligomerization motifs correspond to the positions of disruptions in the native RRE. Preferably, the spacing between the disruptions in adjacent Rev-binding motifs are less than 11 base pairs. In more preferred embodiments the spacing is less than 8 base pairs, and may be less than 5 base pairs.

Fifth, the nucleation motif is recognized by Rev in a sequence-specific manner.

—EG RN AYP—

—FCR'(N')$_n$GR"Q— where n=0 or 1; Y & R" are, respectively, a pyrimidine and purine; E & F are nucleotides which can form a base pair; P & Q are nucleotides which can form a base pair; R and R' is a purine; and N and N' is any nucleotide.

In an especially preferred nucleation motif sequence, n=0, E is C, F is G, N is U, R is G, R' is G, Y is C, R" is G. This preferred nucleation motif corresponds to the RNA minimal Rev binding motif present in the native RRE (see WO92/051595, the contents of which are incorporated herein by reference), shown boxed in FIG. 1[SEQ ID NO: 1; nucleotides 103–108 and 127–133].

Another preferred nucleation motif sequence n=0, E is C, F is G, N is U, R is A, R' is A, Y is C, R" is G. The nucleation motif also can be a sequence corresponding to an aptamer that binds Rev with high affinity as described by Symensma et al., 1996, Jour. Virol. 70:179; Leclerc et al., 1994, Nature Structural Biol. 1 :293, and Ye et al., 1996, Nature Structural Biol. 3:1026. When the nucleic acid is produced by chemical synthesis, then the nuleation motif can contain modified bases that are not normally present in the RRE, such as inosine, as described by Iwai et al., 1992, Nucl. Acids Res. 20:6465.

Methods described below for determining the usefulness of specific nucleic acid sequences as Rev decoys according to the invention also may be used to determine whether other nucleic acid sequences having the general properties described and defined herein are useful in the invention. These methods include testing of model RREs for the sequence and length requirements which determine binding site affinity, testing for the effect of duplex disruptions on HIV Rev binding, spacing requirements between the nucleation and oligomerization binding sites for HIV Rev binding, the effect of polarity of nucleation and oligomerization sites on HIV Rev binding, and how to calculate the co-operativity of Rev binding, and whether cooperative binding of the nucleic acid molecule by two or more Rev protein monomers occurs with a higher degree of co-operativity than the wild-type RRE.

The methods described below also may be used by one of skill in the art to screen for candidate inhibitors of the Rev/nucleic acid binding interaction and/or for candidate inhibitors of Rev oligomerization on the RRE RNA molecule. Such assays are performed by reacting Rev protein with a nucleic acid prepared according to the invention, and containing both a nucleation and an oligomerization motif, in the presence of a candidate inhibitor (tested at a variety of concentrations). The reaction mixture is then analyzed by gel electrophoresis to determine both the degree of binding of Rev and the cooperativity of binding of Rev, as described herein.

Inhibition is identified as follows: (i) a reduction of binding or cooperativity with respect to a control reaction performed in parallel in the absence of the candidate inhibitor (for example, a reduction by at least 10% in terms of binding or cooperativity relative to the control), and/or (ii) a statistically significant reduction in either the binding constant or cooperativity index with respect to a previously determined value is indicative of inhibition by the candidate inhibitor.

Candidate inhibitors may be found in any class of RNA binding compounds that bind to RNA disruptions present in the RRE, including for example antibiotics in the aminoglycoside family, linear peptides carrying basic amino acids, cyclic peptide antibiotics, and peptidomimetics.

The inhibition assay also can be used to detect a compound that interferes with protein-protein interactions responsible for Rev oligomerization. This type of inhibitor would not confer inhibition of the binding interaction between Rev and the nucleic acid via direct binding to the nucleic acid, but instead would inhibit the binding interaction via inhibition of Rev oligomerization. Thus, there would be a reduction in the cooperativity of binding.

Nucleic Acid molecules of the invention also can be used as the basis for additional assays for cooperative binding of Rev to RRE using physical detection techniques, such as surface plasmon resonance or filter binding assays, in order to determine the number of Rev molecules that are able to bind to a model RRE substrate in the presence or absence of the candidate inhibitor. Such nucleic acids also are used as a component of a kit for determining the degree of Rev binding to an RNA and the cooperativity of binding of Rev to RNA.

Model RRE substrates

To investigate the sequence and structural requirements for Rev oligomerization along the RRE, model substrates were constructed (eg. Bartel et al., 1991; Cook et al., 1991; Heaphy et al., 1991; Iwai et al., 1992; Kjems et al., 1992; Tiley et al., 1992; Giver et al., 1993; Jensen et al., 1994; Pritchard et al., 1994; Jensen, T. H. et al., 1995).

The footprint of a Rev molecule bound to the high-affinity site on wild-type RRE is known to cover around 11 base pairs (Iwai et al., 1992; Kjems et a!, 1992; Tiley et al., 1992; Pritchard et al., 1994), while the binding of each extra Rev monomer covers an additional 6 to 8 base pairs of stem length (Mann et al., 1994). In order to accommodate the binding of further Rev monomers, the model substrates used contain 16 base pairs of duplex on one side of the wild-type RRE nucleation motif. Therefore, the minimum length of a model substrate according to the invention includes an 11 base pair region joined to two regions of 6–8 bases, or 23–27 bases. This basic model substrate is termed RWZ1 [SEQ ID NO: 3] (see FIG. 2). All other model substrates are based on RWZ1 [SEQ ID NO: 3], but they feature added duplex disruptions at sites corresponding to the positions of stems IIc, III/IV, and V in the native RRE[SEQ ID NO: 1]. None of the model substrates are fully active as Rev response elements in vivo. The maximum length of an RRE oligomerization substrate useful according to the invention is limited by the length of a nucleic acid decoy which may be retained in the nucleus and which does not form internal secondary structures prohibitive of Rev binding. This length may be sufficient to bind 20–30 Rev monomers (wherein after the binding of the first Rev monomer each successive Rev monomer occupies 6–8 nucleotides, corresponding to about 160–240 nucleotides in length). Long molecules capable of binding Rev cooperatively also must form a continuous duplex structure which is periodically interrupted by disruptions such as those described in this invention. Sequences carrying stretches of uninterrupted duplex RNA that are longer than 11 base pairs may inhibit the addition of subsequent Rev molecules.

A model substrate RNA molecule of the invention also may be presented in the form of a multiple copy nucleic acid molecule to provide multiple Rev binding substrates on a single vector. Linker sequences may be inserted between the Rev binding sites to ensure that the multi-site molecule folds so as to permit Rev binding, thus generating a series of contiguous nucleation and oligomerization sites. Alternatively, individual Rev binding sites may include sequence variations in their duplex regions that favor folding of the entire multi-site molecule into individual Rev binding sites. Such sequences can be designed using RNA folding algorithms such as those described in Jaeger et al., 1989, Proc. Nat. Acad. Sci. 86:7706, and Jaeger et al., 1989, Methods Enzymol. 183:281.

The Requirement for Duplex disruption

Figure 2A:
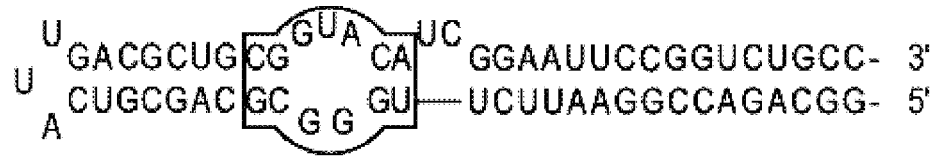
Figure 2B:
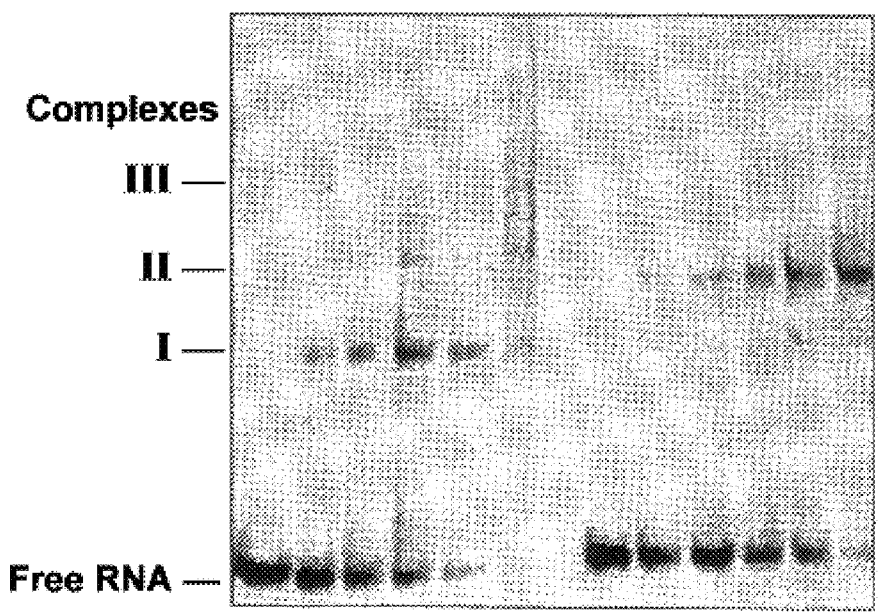

The basic model substrate RWZ1 [SEQ ID NO: 3] was found primarily to bind a single Rev monomer (complex I, FIG. 2). Complexes II and III (which represent two or three bound Rev monomers, respectively) are not observed until there is at least a fourfold excess of Rev.

To investigate the structural features of the RRE which enable Rev oligomerization to take place, disruptions of the duplex structure were introduced at sites corresponding to the positions of stems IIc, III/IV, and V in the native RRE.

The addition of a small dinucleotide bulge (UC) adjacent to the nucleation motif followed by a potential non-Watson-Crick G•U base pair (RWZ2) [SEQ ID NO: 4] produces a dramatic change in Rev-binding activity (FIG. 2). The main complex formed with RWZ2 [SEQ ID NO: 4] is complex II. Rather than there being an intermediate situation with Rev being distributed between complexes I and II, potential Rev-binding sites are filled up with a strong preference for complex II. Even at low Rev. concentrations, complex II is formed in preference to complex I. Oligomerization on RWZ2 [SEQ ID NO: 4] therefore appears to be highly co-operative.

Figure 3A:
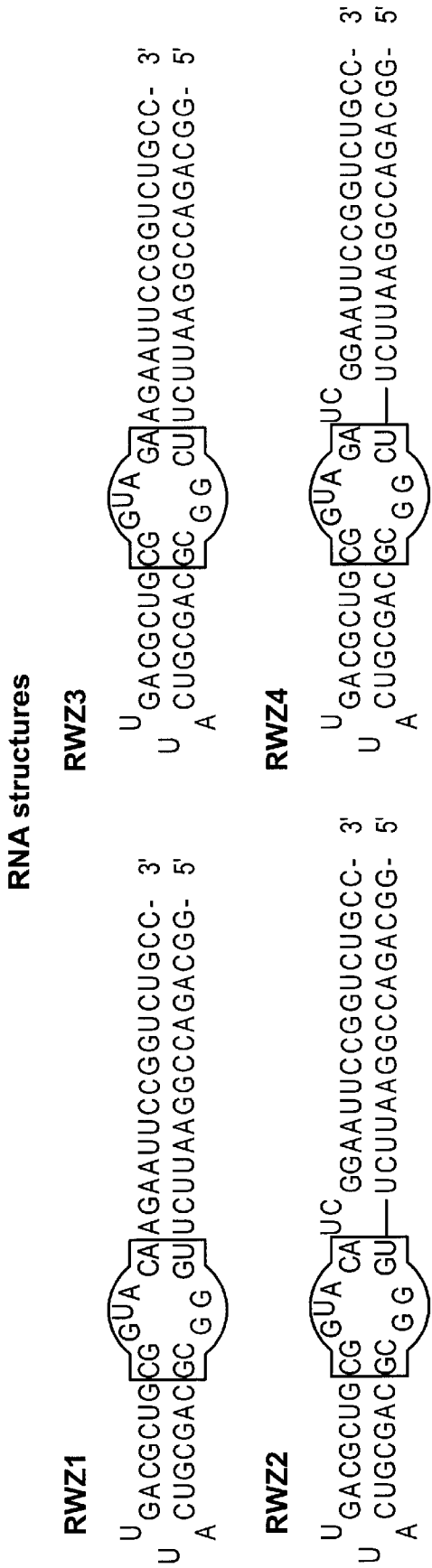
FIG. 3 shows the predicted secondary structures of model substrates RWZ1, [SEQ ID NO: 3] RWZ2[SEQ ID NO: 4], RWZ3 [SEQ ID NO: 5] and RWZ4 [SEQ ID NO: 6] along with the results from gel-retardation assays using these substrates.
Figure 3B:
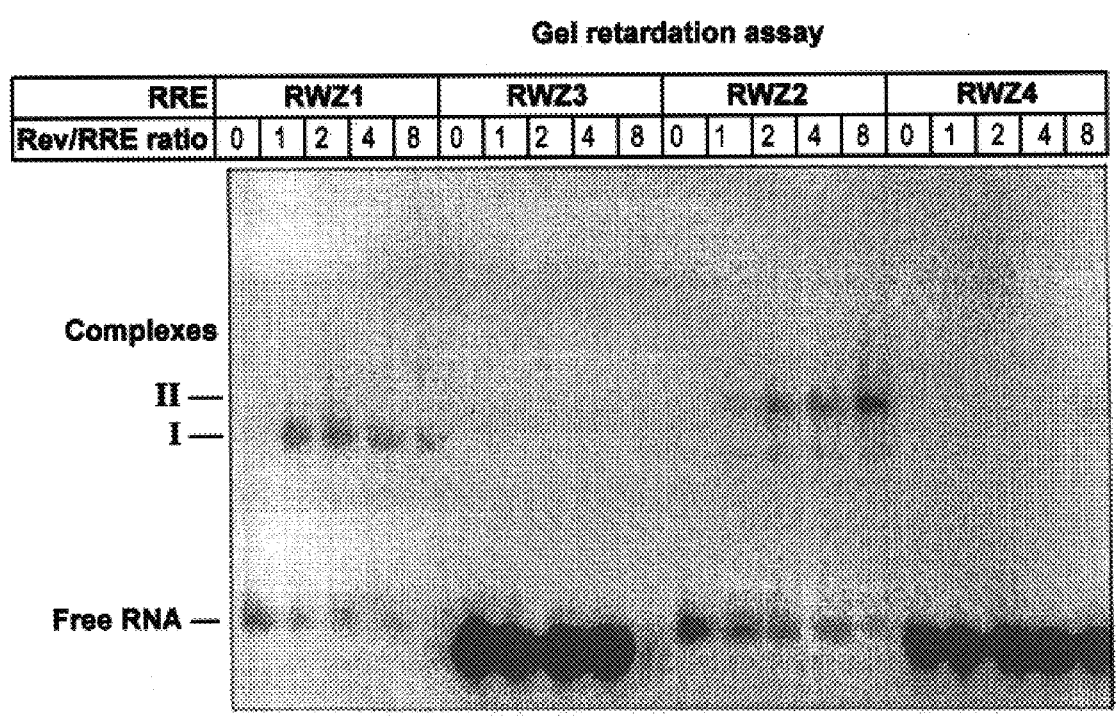
Figure 4A:
FIG. 4 shows the predicted secondary structures of model substrates RWZ2 [SEQ ID NO: 4], RWZ5 [SEQ ID NO: 7] and RWZ6 [SEQ ID NO: 8] along with the results from gel-retardation assays using these substrates.
Figure 4A:
Figure 4A:
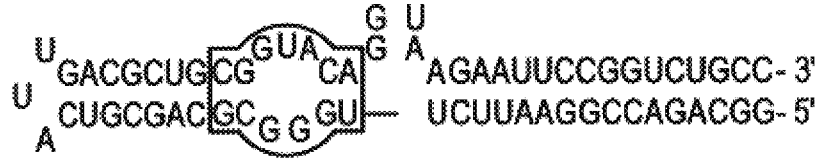
Figure 4B:
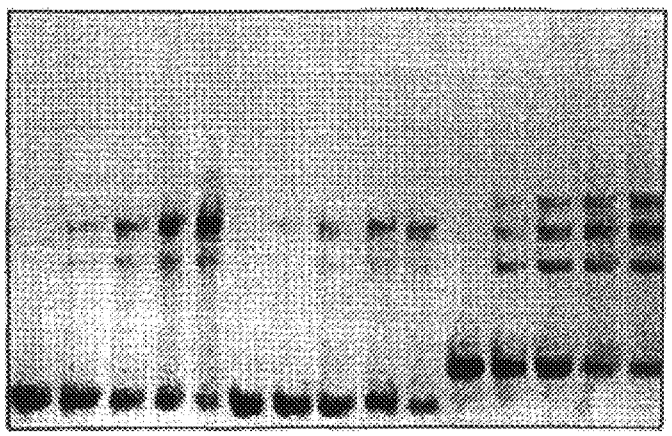
Figure 5A:
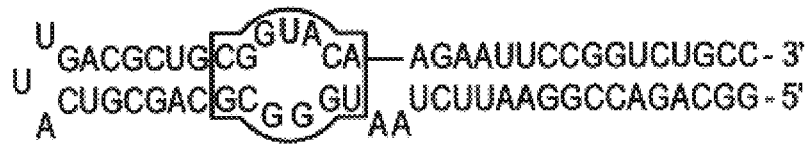
FIG. 5 shows the predicted secondary structures of model substrates RWZ7, [SEQ ID NO: 9] RWZ8 [SEQ ID NO: 10] and RWZ9 [SEQ ID NO: 11] along with the results from gel-retardation assays using these substrates.
Figure 5A:
Figure 5A:
Figure 5B:
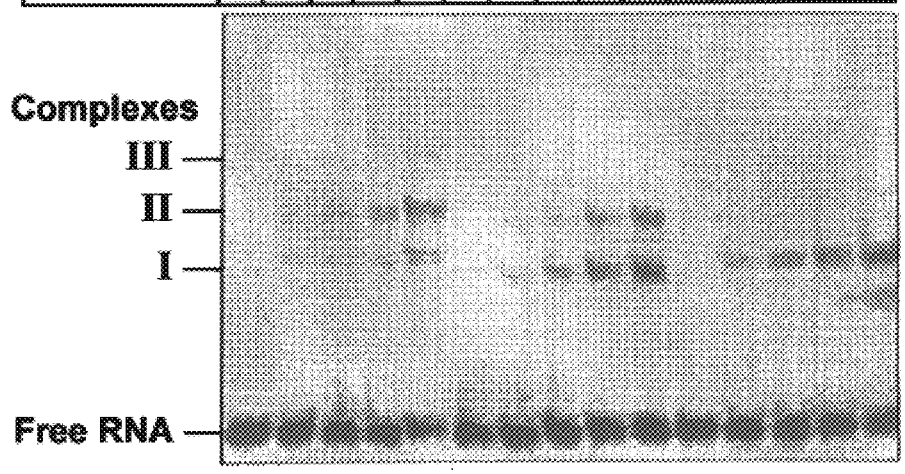
Figure 6A:
FIG. 6 shows the predicted secondary structures of model substrates RWZ1 [SEQ ID NO: 3] RWZ2 [SEQ ID NO: 4] and RWZ15 [SEQ ID NO: 12] along with the results from gel-retardation assays using these substrates.
Figure 6A:
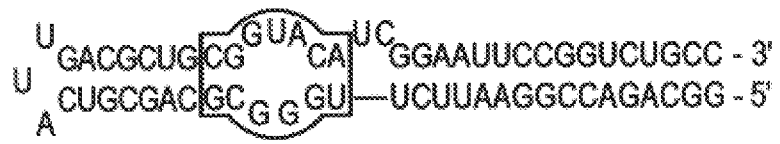
Figure 6A:
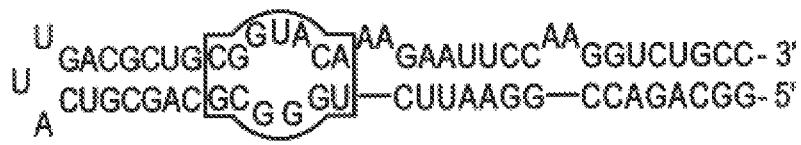
Figure 6B:
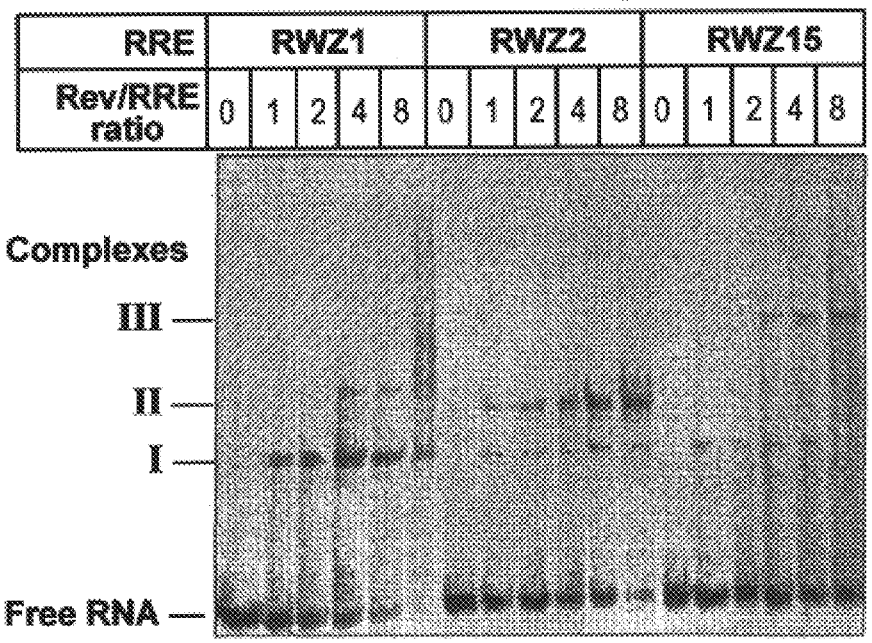
Figure 7A:
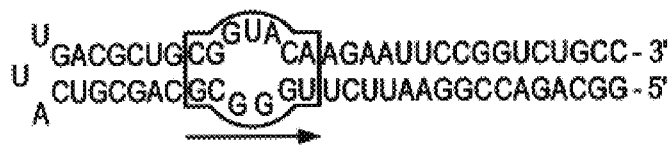
FIG. 7 shows the predicted secondary structures of model substrates RWZ1 [SEQ ID NO: 3], RWZ10 [SEQ ID NO: 13], RWZ11 [SEQ ID NO: 14], and RWZ12 [SEQ ID NO: 15] along with the results from gel-retardation assays using these substrates. The arrows indicate the direction of assembly on the wild-type RRE.
Figure 7A:
Figure 7A:
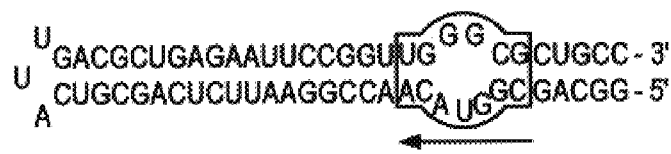
Figure 7A:
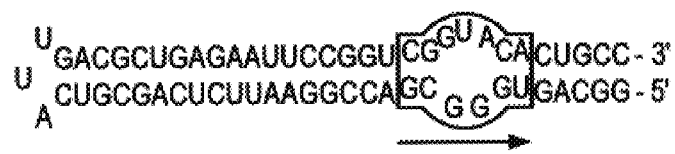
Figure 7B:
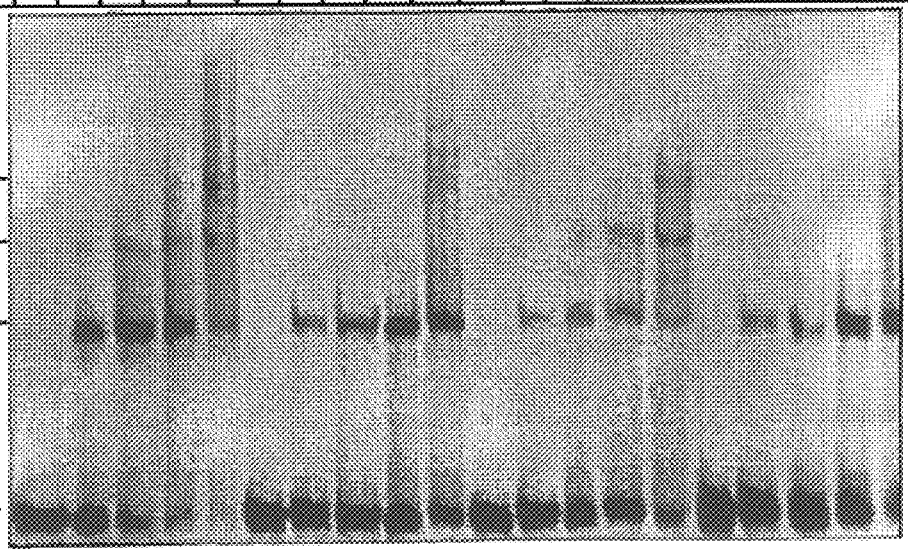
Figure 8A:
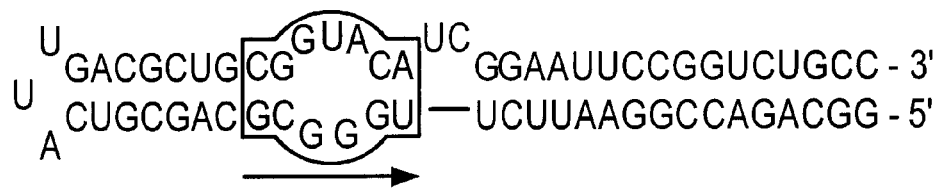
FIG. 8 shows the predicted secondary structures of model substrates RWZ2 [SEQ ID NO: 4], RWZ6 [SEQ ID NO: 8], RWZ13 [SEQ ID NO: 16], and RWZ14 [SEQ ID NO: 17] along with the results from gel-retardation assays using these substrates. The arrows indicate the direction of assembly on the wild-type RRE.
Figure 8A:
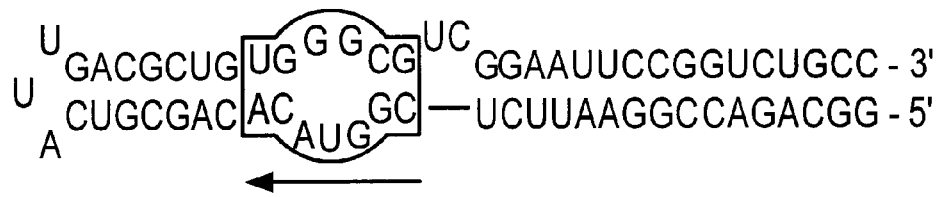
Figure 8A:
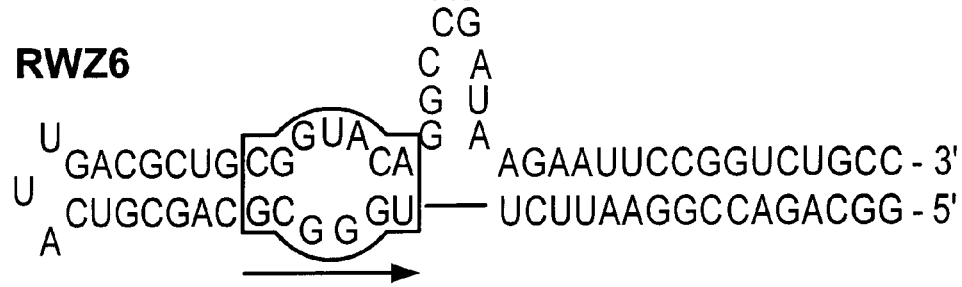
Figure 8A:
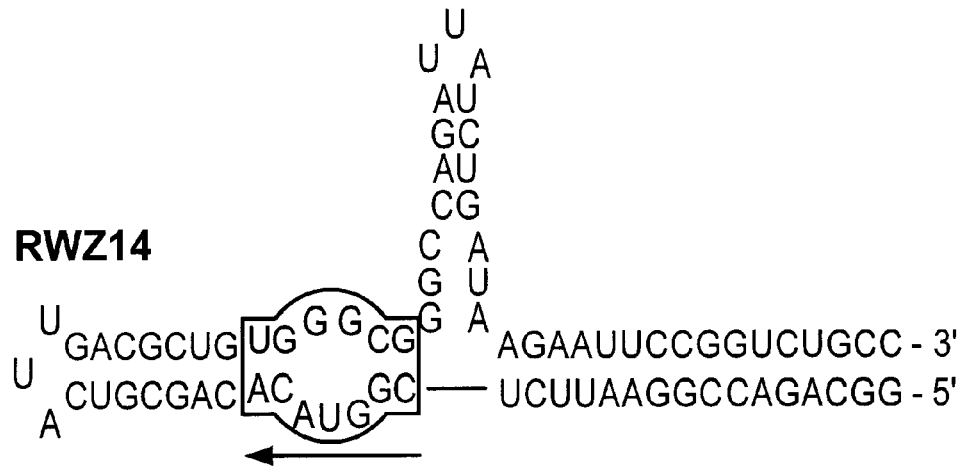
Figure 8B:
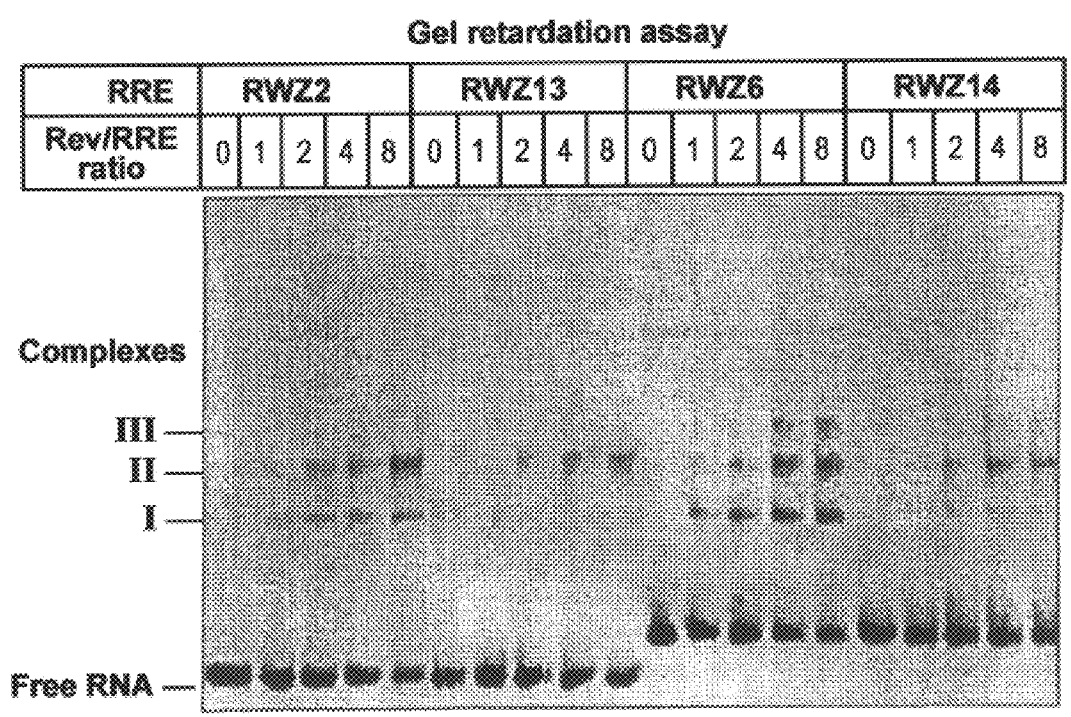

To demonstrate that the efficient assembly observed on RWZ$^2$ [SEQ ID NO: 4] was initiated at the nucleation motif rather than at a second, independent Rev binding site, control experiments were performed using substrates carrying defective nucleation motifs. In RWZ3 [SEQ ID NO: 5] and RWZ4 [SEQ ID NO: 6], two base pairs in the high affinity motif were reversed (FIG. 3). These mutations preserve the secondary structure of the nucleation motif but remove functional groups necessary for Rev recognition (Iwai et al., 1992; Kjems et ,2., 1992; Pritchard et al., 1994). Neither RWZ3 [SEQ ID NO: 5] nor RWZ4 [SEQ ID NO: 6] formed any significant complexes with Rev, even at an eightfold protein excess (FIG. 3).

It seems, therefore, that a UC dinucleotide bulge functionally linked to the nucleation motif followed by a potential non-Watson-Crick G•U base pair is an effective oligomerization motif.

To investigate whether efficient oligomerization can also take place when different types of disruption are introduced into the duplex flanking the nucleation motif, substrates RWZ5 [SEQ ID NO: 7] and RWZ6 [SEQ ID NO: 8] were constructed (FIG. 4). In RWZ5 [SEQ ID NO: 7] the UC bilge of RWZ2 [SEQ ID NO: 4] is replaced by an AA bulge, and the G•U base pair is absent. In RWZ6 [SEQ ID NO: 8] a shortened form (17 nucleotides) of Stem IIc from the wild-type RRE, sequence [SEQ ID NO: 1] is inserted, creating a three-way junction adjacent to the nucleation motif.

Rev oligomerized on both RWZ5 [SEQ ID NO: 7] and RWZ6 [SEQ ID NO: 8] (FIG. 4). The ratio of complex I:complex II with RWZ5 [SEQ ID NO: 7] is comparable to that of RWZ2 [SEQ ID NO: 1], indicating a similar degree of co-operativity of Rev binding, but the lighter band on the gel suggests that RWZ5's [SEQ ID NO: 7] binding affinity is weaker. The presence of the stem on RWZ6 [SEQ ID NO: 8] had a large influence on oligomerization, allowing up to three Rev molecules to bind (complex III), but the continued presence of complex I even at an eight-fold excess of Rev suggests that Rev binding is not fully co-operative.

The Strandedness of Disruption

To investigate the strand-specificity of the disruption which formed the oligomerization motif in RWZ5 [SEQ ID NO: 7], substrate RWZ7 [SEQ ID NO: 9] was constructed (FIG. 5). The disruption was introduced at the same distance from the nucleation motif as in RWZ5 [SEQ ID NO: 7], but into the opposite strand. While this is presented as a dinucleotide insertion in one strand, in structural terms this oligomerization motif is the same as a dinucleotide deletion in the other strand. The binding activity of RWZ7 [SEQ ID NO: 9] is similar to that of RWZ5 [SEQ ID NO: 7]. Complex II was the main product throughout the concentration range, even at low Rev:RRE ratios. This indicates that an oligomerization motif may be a disruption positioned on either strand of the duplex.

The Separation of Nucleation and Oligomerization Motifs

The effect of the separation between the nucleation and oligomerization motifs was investigated using substrates RWZ5 [SEQ ID NO: 7], RWZ8 [SEQ ID NO: 10] and RWZ9 [SEQ ID NO: 11] (FIG. 5). These substrates contain the same oligomerization motif disruption, namely an AA bulge, but at different distances from the nucleation motif. While RWZ$^5$ [SEQ ID NO: 7] favors complex II formation, RWZ9 [SEQ ID NO: 11] forms almost exclusively complex I at all Rev concentrations studied (FIG. 5). RWZ8 [SEQ ID NO: 10] is intermediate, with complex I always in excess over complex II. Moving the oligomerization motif disruption away from the nucleation motif therefore makes the binding of a second Rev less favorable, and the disruption which forms the oligomerization motif is unable to influence Rev oligomerization when it is separated from the nucleation motif bubble by nine nucleotides or more.

For the AA bulge oligomerization motif disruption, the distance between the nucleation motif and the first adjacent oligomerization motif appears to be crucial to the formation of protein-protein contacts. Therefore while oligomerization motifs seem to be able to function in a strand-independent manner, there seems only to be a "window" of effective distance between neighboring Rev-binding motifs, which encompasses a spacing of 1–12 nucleotides.

Binding Successive Rev Monomers

At an excess of Rev, some complex III is formed with RWZ1 [SEQ ID NO: 3] and RWZ6 [SEQ ID NO: 1]. It is clear, therefore, that there is a sufficient length of duplex to bind three Rev molecules, though this does not seem to be favored. To investigate whether a second oligomerization motif promotes the binding of a third Rev monomer, construct RWZ15 [SEQ ID NO: 12] was synthesized (FIG. 6). This is based upon RWZ5 [SEQ ID NO: 7], but features a second identical disruption 8 base pairs away from the first. The gel retardation results for RWZ15 [SEQ ID NO: 18] FIG. 6) show that the addition of a single further disruption leads to the formation of complex III exclusively under conditions where RWZ1 [SEQ ID NO: 3] and RWZ2 [SEQ ID NO: 4] form complexes I and II respectively. This demonstrates the principle that the addition of successive oligomerization motifs facilitates the co-operative binding of successive Rev monomers.

Polarity of Oligomerization

Chemical probing, nuclease protection experiments, and footprinting studies indicate that Rev monomers bind asymmetrically to the nucleation motif (Iwai et al., 1992; Kjems et al., 1992; Tiley et al., 1992; Pritchard et al., 1994) and oligomerize in a single direction along stem I of the RRE (Bartel et al., 1991; Heaphy et al., 1991; Iwai et al., 1992; Kjems et al., 1992; Tiley et al., 1992; Mann et al., 1994).

If the direction of assembly is determined primarily by protein-protein interactions between Rev molecules, then it must be specified by the orientation of the Rev bound at the nucleation motif. Alternatively, assembly could be permitted in either direction away from the nucleation motif with the structure of the flanking RNA creating the polar pattern of assembly. To investigate which of these scenarios is correct, RNA molecules RWZ10 [SEQ ID NO: 1], RWZ11 [SEQ ID NO: 14], RWZ12 [SEQ ID NO: 12], RWZ13[SEQ ID NO: 16], and RWZ14 [SEQ ID NO: 14] were constructed (FIGS. 7 & 8).

RWZ10 [SEQ ID NO: 13] contains a nucleation motif in reverse orientation compared to the motif in RWZ1[SEQ ID NO: 3]. In RWZ11 [SEQ ID NO: 14] and RWZ12 [SEQ ID NO: 15] the nucleation motif is displaced along the duplex, but in RWZ11 [SEQ ID NO: 14] it is in reverse orientation. As the interaction between Rev and the nucleation motif involves base-specific contacts, the orientation of the initial monomer binding event is fixed by the RNA sequence. Reversing the nucleation binding motif therefore reverses the orientation of the first Rev monomer.

RWZ10 [SEQ ID NO: 13], RWZ11 [SEQ ID NO: 14], and RWZ12 [SEQ ID NO: 15], none of which contain an oligomerization motif, all form exclusively complex I (FIG. 7). Even at a 16-fold excess of Rev, there was no evidence of complex II or III formation except in RWZ11 [SEQ ID NO: 14], which was able to form small amounts of these two complexes. The ability to bind a Rev monomer is therefore not affected by the orientation of the nucleation motif.

RWZ13 [SEQ ID NO: 16] and RWZ14 [SEQ ID NO: 17] are identical to RWZ2 [SEQ ID NO: 4] and RWZ6 [SEQ ID NO: 1], except that the orientation of their nucleation motifs are reversed FIG. 8). FIG. 8 shows that the assembly activities of RWZ13 [SEQ ID NO: 16] and RWZ14 [SEQ ID NO: 17] are comparable to those of RWZ2 [SEQ ID NO: 4] and RWZ6 [SEQ ID NO: 10]: RWZ2 [SEQ ID NO: 8] and RWZ13 [SEQ ID NO: 4] [SEQ ID NO: 16] both formed complex II; RWZ6 [SEQ ID NO: 8] and RWZ14 [SEQ ID NO: 17] both formed complexes II and m. Rev oligomerization is therefore not dependent on the orientation of the nucleation motif.

It should be noted that while the Rev oligomerization can occur in the reverse direction to that normally seen, RWZ13 [SEQ ID NO: 16] does seems to bind Rev with a lower affinity but higher co-operativity than RWZ2 [SEQ ID NO: 4] (higher ratio of complex II:complex I). RWZ14 [SEQ ID NO: 17] also showed reduced affinity for Rev and formed only small amounts of Complex III compared to RWZ66 [SEQ ID NO: 8].

Therefore, while oligomerization motifs have slightly different influences on Rev oligomerization depending on which side of the nucleation motif they are situated, it is clear that oligomerization motifs can direct the addition of further Rev monomers when placed either upstream or downstream of the nucleation motif. Rev can oligomerize at either end of an already formed nucleoprotein complex and proceeds in the direction of the oligomerization motif disruption. The unidirectional assembly of the oligomer would therefore appear to be due to the structure of the RRE rather than being an intrinsic property of the Rev protein. On a substrate carrying a nucleation motif flanked by perfect duplex RNA, little oligomerization occurs, even when sufficient length of duplex is present. The effect of flanking RNA structure clearly dominates over the we<k, nucleation motif-mediated directionality seen on perfect duplex RNA.

Co-operativity Calculations

Figure 9:
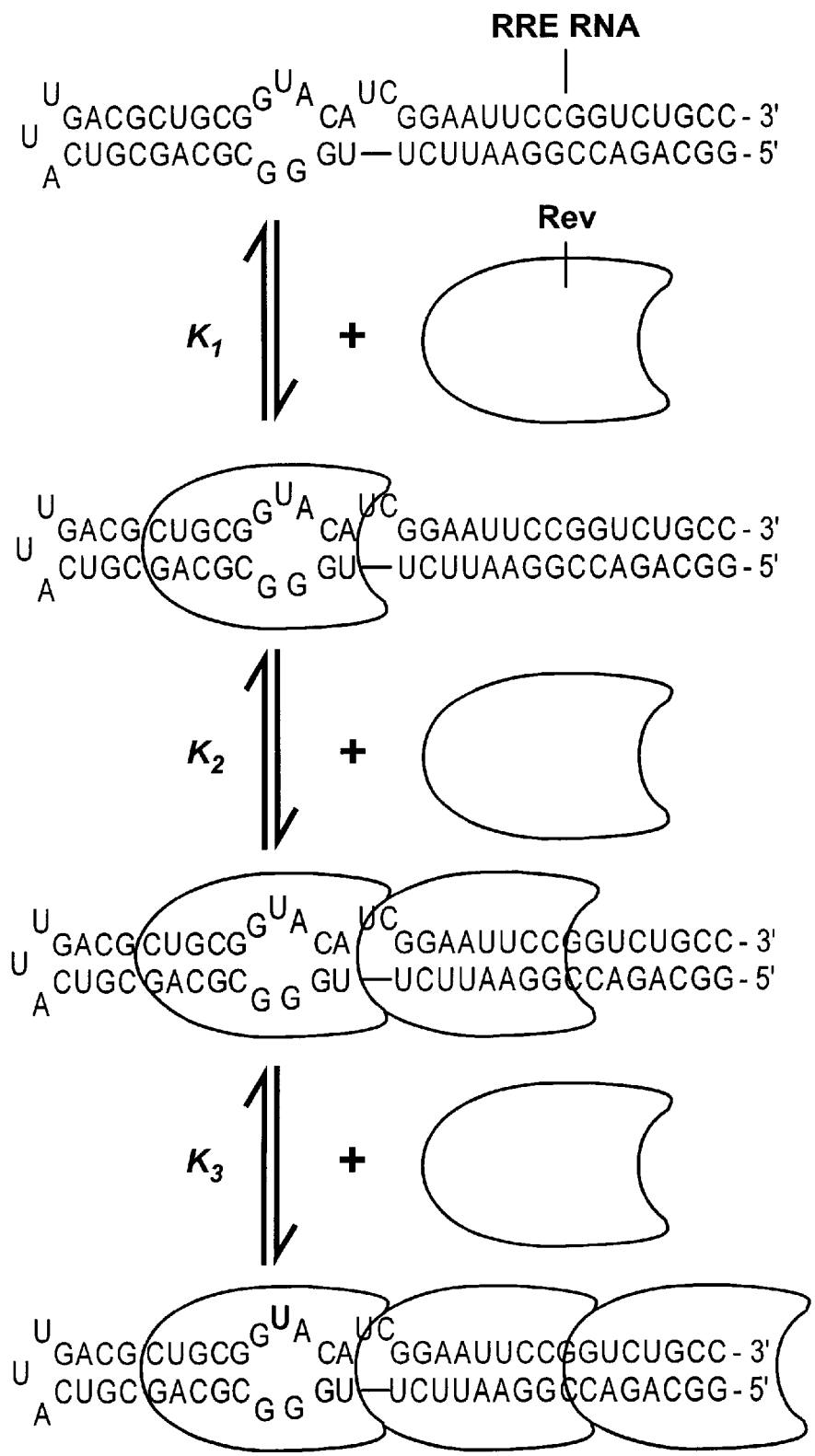
FIG. 9 shows a schematic model for Rev oligomerization onto model RRE substrates (RWZ2 [SEQ ID NO: 4] shown). The first Rev monomer binds to the nucleation motif with dissociation constant $K_1$. Further Rev monomers then elongate the nucleoprotein complex by binding to the protruding RNA stem alongside the already-bound Rev, with dissociation constants $K_2$ and $K_3$.

In order to obtain an estimate of the extent of the co-operativity of Rev binding by the structures described above, the Rev/RNA interaction was modeled. The model gives estimate values for the dissociation constants ($K_d$) for each successive Rev binding (FIG. 9). The classical model of protein/nucleic acid interactions (McGhee & von Hippel, 1974) includes the effect of co-operative binding, but assumes random binding of the first molecule, rather than, as in the present case, binding to a specific site. It was therefore necessary to derive new equations to model Rev binding to the RRE (see below). These are simpler than those of McGhee & von Hippel as each successive binding is to a specific unique location.

In the adopted model, each Rev monomer is assumed to bind to the complex formed by the earlier monomers, interacting both with the terminal Rev and the stem of the RRE protruding from the nucleoprotein complex. While the model can produce independent estimates of each $K_d$ ($K_1$, $K_2$, $K_3$ ...), it is also possible to obtain values for $K_1$ and $K_2$ from the fitting to simpler RRE variants. For example, the estimates of $K_1$ were within the estimated error of fitting irrespective of whether the data was fitted for an RNA which forms mainly complex I (eg. RWZ1 [SEQ ID NO: 3]) or for the related RNA which favors complex II (eg. RWZ2 [SEQ ID NO: 2]). The observation that similar values obtained for $K_1$ are obtained from the analysis of either molecule suggests that the binding of Rev molecules to the high-affinity site is a primary event which is not affected by the availability of potential binding sites for subsequent monomers.

In order to obtain as accurate values as possible, the value from the simpler model substrates were usually used as this often gave a more reliable fit than attempting to fit all the higher-order binding constants onto the limited data available. Thus, taking the value from the fit to RWZ1 [SEQ ID NO: 3] forward to the fit of, for instance, RWZ2 [SEQ ID NO: 4] resulted in a smaller error of fit for $K_2$. In the cases where the structure of the RNA was altered significantly (RWZ8 [SEQ ID NO: 10], RWZ9 [SEQ ID NO: 11], & RWZ15 [SEQ ID NO: 12]), $K_d$ values for the addition of Rev monomers differed significantly and these were each taken from a single fitting calculation.

Figure 10A:
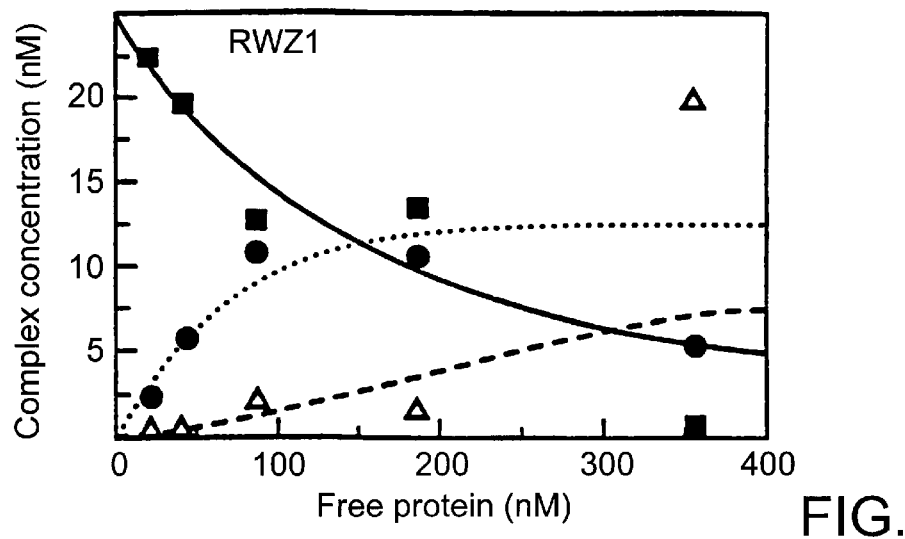
FIG. 10 show examples of the results of fitting binding data from RWZ1 [SEQ ID NO: 3], RWZ2 [SEQ ID NO: 4], and RWZ6 [SEQ ID NO: 8] to the model of FIG. 9. The data at a free protein concentration of approximately 350nM with RWZ1 [SEQ ID NO: 3] was excluded during the fitting as it deviated from a smooth progression from lower protein concentrations and hence did not appear reliable. Filled square=experimental measurement of free RNA concentration; Filled circle=concentration of Rev monomer complex; Hollow triangle=concentration of Rev dimer complex; Hollow circle=concentration of Rev trimer complex; Solid line=fitted curve for free RNA concentration; Dotted line= fitted curve for monomer complex formation; Dashed line= fitted curve for dimer complex formation; Broken line=fitted curve for trimer complex formation.
Figure 10B:
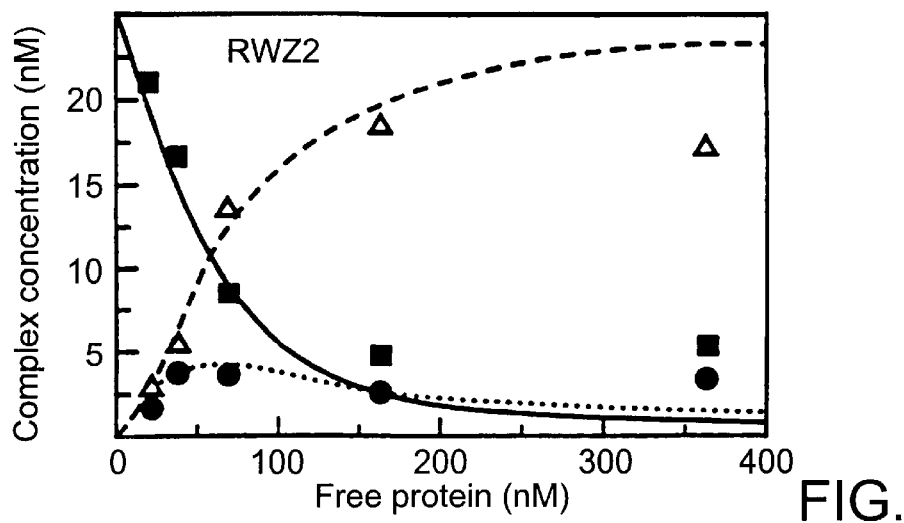
Figure 10C:
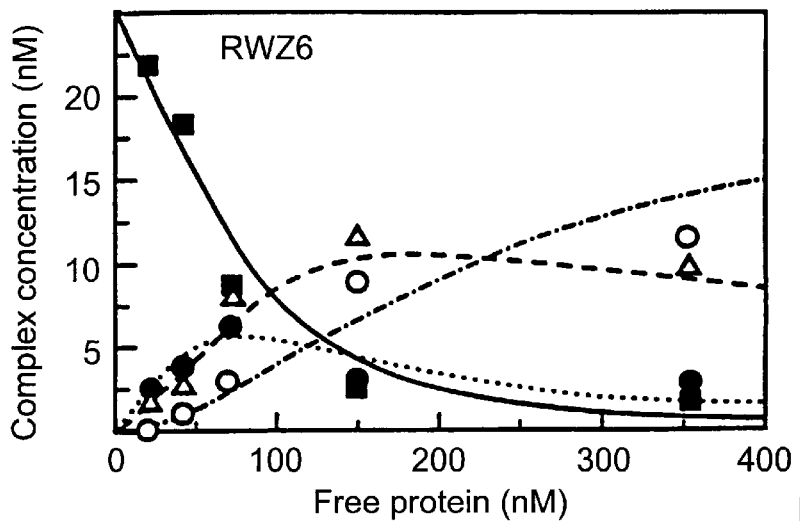

Examples of fitting the data to the model for constructs RWZ1 [SEQ ID NO: 3], RWZ2 [SEQ ID NO: 4], and RWZ6 [SEQ ID NO: 8], are shown in FIG. 10.

The effect of different oligomerization motifs on co-operativity can be estimated from the variation in $K_d$ for each successive addition of a Rev monomer($K_1$ $K_2$ $K_3$ etc.). Table 1 shows the ratios of $K_d$s compared with the initial binding of a Rev to the nucleation motif in the wild-type RRE[SEQ ID NO: 1]. Due to the specificity of binding at the nucleation motif, the contribution from the interaction of RNA molecules with oligomerization motifs will be lower than that for the first Rev.

The best estimate for the magnitude of this effect comes from the comparison of specific and non-specific Rev binding (Heaphy et al., 1991), where a difference of approximately 20-fold was obtained. In the absence of any direct Rev-Rev interaction the ratio $K_2/K_1$ would therefore be approximately 20 for arty non-specific RNA, which should most closely approximate the smooth double-stranded stem found, for instance, in RWZ1 [SEQ ID NO: 3].

In actual fact, as shown in Table 1, this ratio is found to be 4.40 for RWZ1 [SEQ ID NO: 3], corresponding to a co-operativity factor (ω) of 4.6 due to the protein-protein interaction between the Rev bound at the nucleation motif and the Rev bound at the oligomerization motif. This value corresponds to a free energy of −3.8 kjmol⁻¹ due to this interaction.

The co-operativity factors in the binding of the second and, in the case of RWZ6 [SEQ ID NO: 8] and RWZ15 [SEQ ID NO: 12], the third Rev monomers to the RNA molecules investigated herein have been calculated in the same manner and are presented in Table 1. This table also shows the difference in co-operativity compared to the second Rev binding to RWZ1 [SEQ ID NO: 3] (Δω) and the difference in free energy for binding of the Rev to the oligomerization motif due to the structural departures from a smooth stem (ΔΔG).

TABLE 1

$K_d$ ratios and approximate co-operativities for binding of Rev to already nucleated complexes on model RREs.

| RRE variant | $K_d$ ratio[a] | Co-operativity factor (ω)[b] | Δω[c] (kJmol⁻¹) | ΔΔG[d] |
|---|---|---|---|---|
| RWZ1 [SEQ ID NO: 3] | 4.40 | 4.6 | (1.0) | (0) |
| RWZ2 [SEQ ID NO: 4] | 0.15 | 133 | 29.0 | −8.4 |
| RWZ5 [SEQ ID NO: 7] | 0.36 | 55.6 | 12.1 | −6.3 |
| RWZ7 [SEQ ID NO: 9] | 0.68 | 29.4 | 6.4 | −4.6 |
| RWZ8 [SEQ ID NO: 10] | 0.61 | 32.8 | 7.1 | −5.0 |
| RWZ9 [SEQ ID NO: 11] | 15.3 | 1.3 | 0.3 | +2.9 |
| RWZ26 [SEQ ID NO: 8] | 0.41 | 48.8 | 10.6 | −5.9 |
|  | 1.51* | 13.3 | 2.9 | −2.5 |
| RWZ15 [SEQ ID NO: 12] | 0.26 | 76.9 | 16.7 | −7.1 |
|  | 0.19* | 105.3 | 22.9 | −7.5 |

[a]Ratios shown are $K_2/K_1$, except for the second values shown for RWZ6 [SEQ ID NO: 8] and RWZ15 [SEQ ID NO: 12] (marked ), which are $K_3/K_1$.
[b]The co-operativity factor (ω) is defined as $K/K_d$, where K is the dissociation constant for binding of a single Rev monomer to RNA at a non-specific site.
[c]Differences in co-operativity are relative to the binding of the second Rev monomer to RWZ1 [SEQ ID NO: 1] ie compared to binding to a fully base-paired stem, alongside the Rev bound on the nucleation motif.
[d]Differences in free energy for binding of a Rev monomer are calculated relative to that for the second Rev monomer to RWZ1 [SEQ ID NO: 3] ie compared to the co-operative binding of a Rev monomer to a fully base-paired stem.

Each of the oligomerization motifs tested resulted in an increased Rev oligomerization co-operativity, in the range from 6.5-fold to 30-fold, provided that the disruption was located between 2 and 5 base pairs from the nucleation motif (RWZ2 [SEQ ID NO: 4], RWZ5 [SEQ ID NO: 7], RWZ6 [SEQ ID NO: 8], and RWZ8 [SEQ ID NO: 10]). In contrast, moving the oligomerization motif disruption out to 11 base pairs away from the nucleation motif and onto the opposite side of the helix (RWZ9) [SEQ ID NO: 11] lowered the co-operativity of the oligomerization.

The results shown in Table 1 show that there is some sequence preference for oligomerization motifs, with a UC bulge giving about twice the co-operativity increase of any of the AA bulges. It is not known whether this preference is due to some direct protein/RNA interaction or simply due to different ease of distortion of the different bulged RNAs. It is suggested that oligomerization involves phosphate contacts that are similar to those seen at the nucleation motif but with the base-specific contacts absent. Oligomerization probably requires an RNA template with a sufficiently flexible phosphate backbone to permit Rev to make both protein-protein contacts and also the appropriate protein-RNA contacts.

Since the energetics of the Rev/Rev interactions are similar for each additional Rev monomer, the extra binding energy allowed by the distortable RNA structure is likely to be derived from a better fit of the Rev molecule onto the RNA. This is consistent with the observation that changes to the sequence of the bulge and small changes in its location have little effect on the binding energy. Thus, it seems likely that the binding of subsequent Rev monomers causes some bending in the path of the RNA double helix and that the flexibility resulting from a bulge accommodates this bend more easily than a perfect duplex.

Consistent with this hypothesis, there is evidence that Rev binding induces a subtle conformational change in the RNA structure. NMR data suggests that the purine/purine base pairs in the bulge of the high-affinity motif are stabilized by Rev binding (Battiste et al., 1994; Peterson et al., 1994a,b). The binding of Rev multimers to the RRE leads to an enhanced reactivity to single-strand specific, chemical modification reagents at positions opposite stem IIc, one to six nucleotides further away in the duplex, and at some more distant positions (Kjems et al., 1991,1992; Zapp et al., 1993).

Formation of complex III on RWZ15 [SEQ ID NO: 12] shows that the co-operativity enhancement arising from an appropriately located oligomerization motif can also include the interactions between the second and third Rev monomers binding to the RRE. Addition of the third Rev monomer shows a co-operativity difference of 23-fold compared with a smooth stem, which is in the range demonstrated during the formation of complex II on oligomerization motifs.

Routine experiments can determine the optimum separation between any two given oligomerization motifs to give maximum co-operativity, thus obtaining even better co-operativity enhancements than shown here.

Of interest in designing specific oligomerization motifs are the results from RWZ6 [SEQ ID NO: 17], whose oligomerization motif was a truncated stem IIc placed in its normal position. The gel-retardation assay suggested that oligomerization co-operativity was not fall. Table 1 shows that RWZ6 [SEQ ID NO: 17] shows only an approximate 10-fold increase in co-operativity over a pure double-stranded stem, compared with much larger increases for oligomerization motifs made from small bulges. This suggests that the stems found in the wild-type RRE [SEQ ID NO: 1] are sub-optimal for co-operative oligomerization of Rev, allowing instead elongation in a less efficient fashion than could be obtained. This may be an important feature in the function of the RRE as a "molecular rheostat" (Mann et al., 1994) as it allows a graded response to increasing Rev concentration, rather than an all-or-nothing switch which a highly co-operative system produces.

Binding of the third Rev monomer to the smooth stem of RWZ6 [SEQ ID NO: 8] lying beyond the site of the stem IIc analogue is very similar to the binding of the second Rev to the smooth stem adjacent to the high-affinity motif, with an increased co-operativity of only approximately 3. It therefore appears that stem IIc only affects Rev addition to the oligomerization motif immediately beside its junction with stem I and has little continuing effect on further oligomerizations along stem I.

The Role of RRE Stems in in vivo Rev Oligomerization

In the wild-type RRE [SEQ ID NO: 1] (FIG. 1) there is a three-way junction where stem IIc departs from Stem I adjacent to the nucleation motif, followed by six base pairs and then a second disruption at the junction of Stems III/IB and V. Stem I is also punctuated by four single-stranded bulges and nine double-stranded bubbles along its entire length. To determine whether these features are required for RRE function, an additional construct (RRE-S, [SEQ ID NO: 2] FIG. 1) was tested. In RRE-S [SEQ ID NO: 2] stems IIc, III/IV, and V, which are not themselves binding sites for Rev (Mann et al., 1994), are removed and the gaps filled in to generate double stranded RNA, effectively replacing these three stems with 17 base pairs of perfect duplex RNA.

Figure 11:
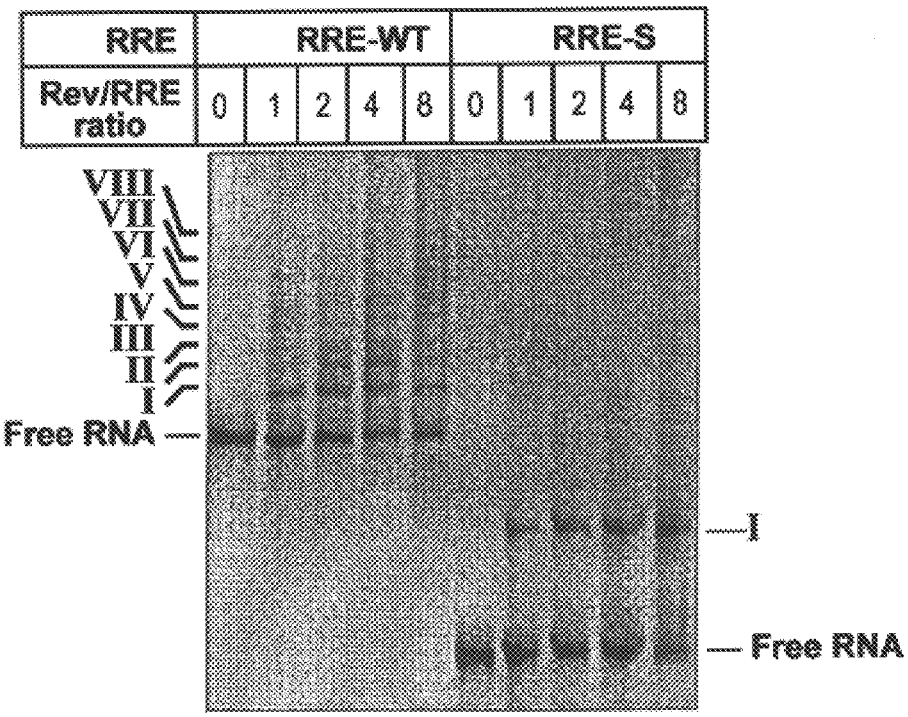
FIG. 11 shows the results from gel-retardation assays using RRE-WT [SEQ ID NO: 1] and RRE-S[SEQ ID NO: 2].

As noted previously, as the concentration of Rev increases, a series of nucleoprotein complexes are formed (Heaphy et al., 1990,1991; Malim & Cullen, 1991; Mann et al., 1994). The RRE can bind up to eight Rev monomers (complex VIII, FIG. 11). In contrast, Rev did not oligomerize on RRE-S, with only complex I being formed even at high Rev concentrations (FIG. 11). These results suggest that the wild-type RRE, [SEQ ID NO: 1] stems IIc, III/IV, and V play an essential role in directing and facilitating Rev oligomerization by altering the RNA structure to allow effective protein/protein contacts when Rev oligomerizes along Stem I. Stem IIc would also seem to direct the direction of Rev oligomerization through its role as an oligomerization motif.

RRE-S [SEQ ID NO: 2] was found not to be active in vivo. RRE-S [SEQ ID NO: 2] was cloned into the Rev-dependent reporter plasmid pIM4 (Mann et al., 1994). After co-transfection of HeLa cells by these constructs together with pF3 1, a plasmid that expresses Rev (Mann et al., 1994), the levels of gag, env, and tat/rev mRNA in the cytoplasm of transfected cells were analyzed by RNase protection assays. Rev was unable to act on RRE-S plasmids, as measured by changes in the levels of the gag or env mRNAs. It would therefore seem that a key requirement for a functional RRE is the ability to bind several Rev monomers.

Gel Retardation assays

The interactions between Rev and the above model RRE substrates were investigated using gel retardation assays (eg. Heaphy et al., 1990; Cook et al., 1991; Malim & Cullen, 1991; Iwai et al., 1992; Kjems et d., 1992; Tiley et al., 1992; Mann et al., 1994; Pritchard et al., 1994).

Binding reactions (10 μl) contained 0.2 5 pmol $^{35}$S-labeled RNA (25nM) or 0.05 pmol $^{32}$P-labeled RNA (5 nM), up to 4 pmol (400 nM) Rev protein in 10 mM Tris-HCl (pH 7.4), 50 mM NaCl, 1 mM DTT and 0.5% Triton X-100. Protein was serially diluted in 200 niM NaCl immediately before use, then a constant volume of each dilution added to successive RNA-containing samples. This was to minimize the effects of Rev aggregation. After incubation on ice for 5 min in siliconized microtiter plates (Falcon), 4 μl loading buffer (0.25% bromophenol blue, 0.25% xylene cyanol, 40% sucrose) was added. The complexes were then applied to 4% (w/v) polyacrylamide gels (acrylamide:bis-acrylamide, 20:1, w/w) containing 0.5× TBE buffer (23 mM Tris base, 23 mM boric acid, 5 mM EDTA., pH 8.3). The gels were pre-run for 1hr before samples (4 μl) were loaded. Electrophoresis was performed without buffer recirculation. Gels were dried under vacuum and products were visualized by autoradiography. Densitometry of autoradiograms was performed using the program ImageQuant on a Molecular Dynamics Computing Densitometer model 300A.

Preparation of Model RRE Substrates

The RNA substrates described above were prepared by transcription using T7 RNA polymerase (Krupp, 1988). Sequences based on the fall-length RRE RRE-WT [SEQ ID NO: 1] and RRE-S[SEQ ID NO: 2]) were transcribed from plasmids linearized by digestion with SmaI. Transcription reactions (50 μl) were performed in a buffer containing 40 mM Tris-HCl (pH 7.4), 25 mM NaCl, 16 mM MgCl$_2$, 10 mM DTT, 10 units RNasin 4RNase inhibitor (Promega)), 1 mM ATP, 1 mM CTP, 1 mM GTP, 100nM UTP, and 40 μCi uridine-5'-(α-$^{35}$S)-thio-triphosphate (Amersham). Each reaction contained 5 μg of linearized template and 0.2 μg T7 RNA polymerase.

The shorter RWZ series of substrates were produced by direct transcription from synthetic oligodeoxyribonucleotides containing the T7 RNA polymerase promoter sequence (Martin & Coleman, 1987). The DNA sequence corresponding to the reverse complement of the desired RNA sequence followed by the 17 nucleotide T7 promoter was synthesized. All designed RNA sequences began with GQCAG as this was found to transcribe efficiently. This "template" strand was mixed with "top" strand, consisting of the T7 promoter sequence alone (TTTATCGACTACACTATAG[SEQ ID NO: 20]), each DNA being present at 0.4 μM in 50 μl reaction buffer. The reaction buffer contained 50 mM $MgCl_2$, 80 mg/ml polyethylene glycol (8000 molecular weight), 40 mM Tris-HCl pH 8.1, 1 mM spermidine (Calbiochem), 5MM DTT, 0.01% Triton X-100, 10U RNasin, 2 mM ATP, 2 mM GTP, 2 mM CTP, 80 μM UTP, and 40 μCi uridine-5'-(α-$^{35}$S)-thiotriphosphate. Otherwise the reaction was exactly as above.

The transcription reaction mixes were incubated at 37° C. for 1.5 hours then stopped by the addition of RNase-free DNase I (HT Biotechnology). Incubation was continued for 5 minutes, then 50 μl of denaturing gel loading dyes (95% formamide, 20 mM EDTA, 0.05% bromophenol blue, 0.05% xylene cyanol) were added. Samples were placed in a boiling water bath for 1 minute and then fractionated on 6% polyacrylamide, 8M urea, 1× TBE gels. The RNA band was located by autoradiography and eluted by crushing the gel slice and soaking in a solution of 0.5M sodium acetate and 0.1% SDS. The eluted RNA was passed through a 0.2 μm filter, de-salted using a Sephadex G50 resin in a spin column (Costar) then ethanol precipitated. The pellet was washed with 80% ethanol, then dissolved in sterile TE buffer. Immediately before use in binding reactions, transcripts were refolded by heating to 90° C. followed by slow cooling. Secondary structure of all transcripts was predicted using the RNA folding program of Zuker (Jaeger et al., 1989a; Zuker, 1989).

Preparation of Rev Protein

A chemically synthesized Rev gene carrying the sequence from the HIV-$1_{BRU}$ (Heaphy et al., 1990) was cloned into a T7 expression vector (Tabor & Richardson, 1985) between the NdeI and HindIII restriction sites. The resulting plasmid (pT7-Rev) was transformed into *E. coli* BL21 (DE3). Cells were grown in 2× TY medium at 37° C. to $A_{600}$=0.8 then expression of Rev was induced with 0.4 mM IPTG. Incubation was continued for 1 hour then cells were concentrated by centrifugation. The expressed Rev protein was in the *E. coli* soluble fraction. Purification required cell lysis then ion-exchange (Q-Sepharose) and affinity (Heparin-Sepharose) chromatography. Protein was stored at up to 2 mg/ml in 50 mM Tris-HCl pH 8.0, 1 mM EDTA, 1 mM DTT, 2 mM NaCl in liquid nitrogen.

The protein was analyzed by mass spectrometry and found to be homogenous and unmodified apart from the removal of the N-terminal methionine. The experimentally measured mass of Rev protein agreed with the predicted mass to within 0.5 atomic mass units. The protein could be denatured in 8M urea and refolded with little effect on binding activity. The binding activity of each batch was assayed by gel-retardation under standard conditions using a synthetic oligoribonucleotide corresponding to the high-affinity motif of the RRE, and was found to be essentially constant between preparations.

Mutagenesis of the RRE

Mutant RRE-S [SEQ ID NO: 2] FIG. 11) was constructed by two-step PCR mutagenesis (Hall & Emery, 1991) using the full-length RRE sequence [SEQ ID NO: 1] (Mann et al., 1994) cloned into pUC19 between the EcoRI and XmaI sites as a template. PCR reactions contained 50 ng of DNA template, up to 0.5 μM each primer, 0.4 mM dNTPs (Pharmacia), 2 units of Vent DNA polymerase and the buffer supplied (New England Biolabs). The first PCR reaction used a 3'-end primer and a 5'-biotinylated mutagenic primer to produce an amplified product covering nucleotides 83 to 133, 157 to 162, and 258–351 (numbers refer to the RNA sequence in FIG. 1, and see also Mann et al., 1994). The sequence TTCCT was inserted immediately before nucleotide 258. The product of the first PCR reaction was bound to streptavidin-coated magnetic beads (Dynal) and washed in 2M NaCl, lmM EDTA, 10 mM Tris-HCl, pH 7.5. The two strands of the PCR product were separated by incubation for 10 min at 20° C. in 0.1M NaOH. The biotinylated strand remained bound to the beads, which were then removed by magnetic collection. The resulting supernatant contained single-stranded, non-biotinylated DNA, consisting a large portion of the target sequence and including the desired mutations. The supernatant was neutralized with 0.2M HCl then used as a primer in the second PCR reaction, along with a primer complementary to the 5' end of the target sequence. The fall length product was cloned into pUC19 between the EcoRI and XmaI sites.

Data Analysis

The model for Rev interaction with the RRE is outlined in FIG. 9. The model assumes that initially a Rev monomer binds to the high-affinity motif and that subsequent monomers bind unidirectionally along the flanking RNA sequences. Hence:

$K_1 = (R_f P_f)/RP_1,$ $K_2 = (RP_1 \cdot P_f)/RP_2,$ etc.

$P_f = P_t - (RP_1 + 2 \cdot RP_2 + \ldots) \&$ $R_f = R_t - (RP_1 + RP_2 + \ldots);$ where $R_t$ is the total concentration of RNA, $R_f$ the concentration of free RNA, $P_1P$ the concentration of the Rev monomer complex with RNA, $RP_2$ the concentration of the Rev-dimer complex with RNA etc. and $P_t$ is the total concentration of protein and $P_f$ the concentration of free protein.

After reduction of the terms the equations for the monomer-dimer complex formation can be re-written:

$$RP_1 = \frac{R_1(K_2 \cdot P_f + K_1 \cdot K_2)}{(1 + K_1/P_f)(P_f^2 + K_2 \cdot P_f + K_1 \cdot K_2)} \&$$

$$RP_2 = \frac{R_1 \cdot P_f^2}{P_f^2 + K_2 \cdot P_f + K_1 \cdot K_2}$$

and those for monomer-dimer-trimer complex formation become:

$$RP_3 = \frac{R_1 \cdot P_f^3}{P_f^3 + K_3 \cdot P_f^2 + K_2 \cdot K_3 \cdot P_f + K_1 \cdot K_2 \cdot K_3} \text{ etc.}$$

These equations were used to estimate the values of $K_1$, etc. by non-linear regression fitting to the data, using the program ProFit (Cherwell Scientific Publishing Ltd., Oxford UK) and estimating errors of approximately 10% of the value (or 0.2 nM if this is greater) to allow reasonable simultaneous fitting of the data for different complexes, which are present over a wide range of absolute values in any given experimental series. Graphs of the data were also plotted, and the curves corresponding to the estimated dissociation constants drawn, with the same program.

Values for the concentrations of free RNA and the various complexes were estimated from the normalized ratios of counts in the various bands in the gels, taken from ImageQuant software, and the total RNA concentration taken for each experiment. The free protein values ($P_f$) were estimated from the total protein added for each lane and the amount which was calculated to be bound into each complex in that lane.

DELIVERY OF NUCLEIC ACID MOLECULES OF THE INVENTION TO CELLS

Vectors Accord Invention

Nucleic acid molecules according to the invention may be encoded by a vector, wherein the term "vector" signifies a nucleic acid which is capable of transferring DNA to a host cell.

The vector malt be any circular or linear length of DNA which either integrates into the host genome or is maintained in episomal form.

The invention contemplates the use of a vector containing a DNA according to the invention. Vectors useful according to the invention will include vectors that integrate into host cell nuclear DNA or stable episomal vectors. One skilled in the art will recognize that a variety of vectors will work according to the invention. Some preferred vectors are described below.

A) Episomal Vectors

Extrachromosomal replicators, generally, in addition to their origin function, encode functions that assure equal distribution of replicated molecules between daughter cells at cell division. In higher organisms, different mechanisms exist for partitioning of extrachromosomal replicators. For example, artificial (ARS-containing) plasmids in yeast utilize chromosomal centromeres as extrachromasomal replicators (Struhl et. al., 1979, Proc. Natl. Acad. Sci USA, 76, 1035–1039). In metazoan cells, one well studied example of a stable extrachromosomal replicator exists—the latent origin oriP from Epstein-Barr Virus (EBV). The maintenance function of EBV requires the viral replication factor EBNA-1 and a series of binding sites for EBNA-1 termed the family of repeats (FR). Replication from oriP requires cis-acting elements (the Family of Repeats—FR and the dyad symmetry element) and the viral origin-binding protein, EBNA-1 (Yates et. al., 1984, Proc. Natl. Acad. Sci USA, 81, 3806–3810; Yates et al., 1985, Nature, 313, 812–815). FR has an effect on the stable extrachromosomal replication of the oriP by nuclear retention of the FR containing plasmids in mitosis. This activity directs plasmids into the newly forming nucleus in the telophase stage of the cell division (Krysan et al., 1989, MoL Cell. Biol., 9, 1026–1033).

Particularly preferred vectors useful according to the invention are maintained at a high copy number in dividing and non-dividing cells of a patient. This may be achieved by employing an episomal vector such as the BPV-I vector system described in WO 94/12629 and in Piirsoo et al., 1996, EMBO Jour. 15:1, comprising a plasmid harboring the BPV-1 origin of replication (minimal origin plus minichromosomal maintenance element) and optionally the E1 and E2 genes. The BPV-1 E1 and E2 genes are required for stable maintenance of a BPV episomal vector. These factors ensure that the plasmid is replicated to a stable copy number of up to thirty copies per cell independent of cell cycle stat1s. The gene construct therefore persists stably in both dividing and non-dividing cells. This allows the maintenance of the gene construct in cells such as hemopoietic stem cells and more committed precursor cells.

"Minimal origin of replication" (MO) refers to a minimal cis-sequence within a papillomavirus that is necessary for initiation of DNA synthesis. The MO of BPV-1 is located at the 3' end of the upstream regulatory region within a 60 base pair DNA fragment (7914–7927) including an AT-rich region, a consensus sequence to which all papilloma viral E2 proteins bind, and an E1 protein binding site spanning nucleotide 1. The MO of 9PV is located in the URR fragment (nt 7072–793.3/1–99) (Chiang et al. PNAS 1992).

"E1" refers to the protein encoded by nt 849–2663 of BPV subtype 1; or to nt 832–2779 of HPV of subtype 11, or to equivalent E1proteins of other papillomaviruses, or to functional fragments or mutants of a papillomavirus E1protein, i.e., fragments or mutants of E1which possess the replicating properties of E1.

"E2" refers to the protein encoded by nt 2594–3837 of BPV subtype 1; or to nt 2723–3823 of HPV subtype 11, or to equivalent E2 proteins of other papillomaviruses, or to functional fragments or mutants of a papillomavirus E2 protein, i.e., fragments or mutants of E2 which possess the replicating properties of E2. "Minichromosomal maintenance element" (MME) refers to a region of the papilloma viral genome to which viral or human proteins essential for papilloma viral replication bind, which region is essential for stable episomal maintenance of the papilloma viral MO in a host cell, as described in Pirsoo et al. Preferably, the M is a sequence containing multiple binding sites for the transcriptional activator E2. The MM in BPV is herein defined as the region of BPV located within the upstream regulatory region which includes a minimum of about six sequential E2 binding sites, and which gives optimum stable maintenance with about ten sequential E2 binding sites. E2 binding site 9 is a preferred sequence for this site, as described hereinbelow, wherein the sequential sites are separated by a spacer of about 4–10 nucleotides, and optimally 6 nucleotides. E1 and E2 can be provided to the plasmid either in cis or in trans, also as described in WO 94/12629 and in Piirsoo et al.

"E2 binding site" refers to the minimum sequence of papillomavirus double-stranded DNA to which the E2 protein binds. An E2 binding site may include the sequence 5' ACCN6GGT 3 [SEQ ID NO: 21]', optimally the sequence 5' ACCGTTGCCGGT 3 [SEQ ID NO: 17], the latter of which is the high affinity E2 binding site 9 of the BPV-1 URR; alternatively, an E2 binding site may include permutations of binding site 9, which permutations are found within the URR. One or more transcriptional activator E2 binding sites are, in most papillomaviruses, located in the upstream regulatory region, as in BPV and HPV.

A vector useful according to the invention may include a region of BPV between 6959–7945/1–470 on the BPV genetic map (see WO 94/12629), which region includes an origin of replication, a first promoter operatively associated with a gene encoding an antigen or epitope thereof, the BPV E1gene operatively associated with a second promoter to drive transcription of the E1gene; and the BPV E2 gene operatively associated with a third promoter to drive transcription of the E2 gene.

The promoters which drive expression of the E1 and E2 genes may be identical or different, and may be a tissue-specific promoter, such as the immunoglobulin heavy chain promoter/enhancer for B-cell and the Ig heavy or light chain promoters for blood cell expression, or from ubiquitously expressed genes, for example from the phosphoglycerolkinase, IE-CMV, RSV-LTR or DHFR genes. The arrangement of E1 and E2 genes relative to the BPV origin of replication may mimic the natural orientations of the sequences in the BPV genome, or it may assume a variety of other orientations, the choices of which will be apparent to one of skill in the art.

B) Viral Vectors

In another preferred approach for introducing nucleic acid according to the invention into a target cell, a viral vector containing the nucleic acid is used for transfer. Infection of cells with a viral vector has the advantage that a large proportion of cells receive the nucleic acid, which can obviate the need for selection of cells which have received the nucleic acid. Additionally, molecules encoded within the viral vector are expressed efficiently in cells which have taken up the vector nucleic acid.

1. Retroviruses:

Defective retroviruses are well characterized for use in gene transfer for gene therapy purposes (for a review see Miller, A.D. (1990) *Blood* 76:271). A recombinant retrovirus can be constructed having a nucleic acid encoding an antigen of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses c an be found in *Current Protocols in Molecular Biology*, Ausubel, F.M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2, andψ Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (19188) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad Sci. USA* 88:8377–8381; Chowdhury et al. (1991) *Science* 254:1802–1805; van Beusechem et al. (1992) *Proc. Natl. Acad Sci. USA* 89:7640–7644; Kay et al. (1992) *Human Gene Therapy* 3:641–647; Dai et al. (1992) *Proc. Natl. Acad Sci. USA* 89:10892–10895; Hwu et al. (1993) *J. Immunol*. 150:4:104–115; U.S. Pat. No. 4,868,116; U.S. Patent No. 4,980,286; PCT Application WO 89/07136; PCT Application WO 89/02468; PCT Application WO 89/05345; and PCT Application WO 92/07573).

2. Adenoviruses:

The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Adz, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89):6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Many replication-defective adenoviral vectors are deleted for all or parts of the viral E1 and E3 genes but retain as much as 80% of the adenoviral genetic material.

3. Adeno-Associated Viruses:

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol*. (1992) 158:97–129). It exhibits a high frequency of stable integration (see for example Flotte et al. (1992) *Am. J Respir. Cell. Mol. Biol*. 7:349–356; Samulski et al. (1989) *J. Virol*. 63:3822–3828; and McLaughlin et al. (1989) *J. Virol* 62:1963–1973). Vectors containing as little as 300 base pairs of AAV can be packaged and can integrate. Space for exogenous nucleic acid is limited to about 4.5 kb. An AAV vector such as that described in Tratschin et al. (1985) *Mol. Cell. Biol*. 5:3251–3260 can be used to introduce nucleic acid into cells. A variety of nucleic acids have been introduced into different cell types using AAV vectors (see for example Hermonat et al. (1984) *Proc. Natl. Acad. Sci. USA* 81 :6466–6470; Tratschin et al. (1985) *Mol. Cell. Biol*. 4:2072–2081; Wondisford et al. (1988) *Mol. Endocrinol*. 2:32–39; Tratschin et al. (1984) *J. Virol*.51:611–619; and Flotte et al. (1993) *J. Biol. Chem*. 268:3781–3790).

The vector may be delivered by non-viral means, such as a plasmid, naked DNA or liposomal delivery system, or by viral means, such as in a retroviral vector or other virus-based vectors known in the art. Certain vectors according to the invention may also act as delivery systems. Likewise, certain delivery systems according to the invention may inherently be vectors, but they may be entirely separate. For instance, a viral vector also acts as a delivery system, whereas a liposomal delivery system is not a vector.

Nucleic acid molecules of the invention may be delivered to cells either in vitro, ex vivo or in vivo using delivery methods known in the art. A delivery system useful according to the invention may be viral or non-viral. It may, for example, be a receptor-mediated delivery system. Preferably, the delivery system will be targeted so that nucleic acid molecules according to the present invention are ,;electively taken up by cells susceptible to HIV infection. This may be effected by targeting the delivery system to specific receptors found on cells infected by HIV, such as the CD4 molecule, or by targeting to progenitor cells such that the delivered molecule is subsequently delivered in cells of a particular lineage susceptible to infection by the virus. Non-viral systems avoid some of the difficulties associated with virus-based systems, such as the expense of scaled production, poor persistence of expression, and concerns about safety.

The delivery of nucleic acids according to the present invention to pluripotent progenitor cells, or the use of a non-targeted delivery system has an obvious drawback in that where more than one cell type derives from the progenitor but not all such cell types are susceptible to HIV infection, delivery of the nucleic acid is not fully specific. This problem may be addressed, for instance, where DNA encoding an RNA of the present invention is under the control of tissue-specific and cell-type specific control elements. In preferred embodiments this may be achieved by the use of locus control region (LCR) sequences as described in, for example, EP-B-0332667, EP-A-0668357 and W(95/33841, all of which are incorporated herein by reference. Additional examples of such control elements include tissue-specific promoters and enhancers.

Locus Control Regions (LCRs) (Grosveld et al., Cell 51:975–985, 1987), also known as Dominant Activator Sequences, Locus Activating Regions or Dominant Control Regions, are responsible for conferring tissue specific, integration-site independent, copy number dependent expression on a transgene integrated into chromatin of a host cell. First discovered in the human globin gene system, which was prone to strong position effects when integrated into the chromatin of transgenic mice or mouse erythroleukemia (MEL) cells (Magram et al., Nature 315:338–340, 1985; Townes et al., EMBO J. 4:1715–1723, 1985; Kollias et al., Cell 46:89–94, 1986; Antoniou et al., EMBO J. 7:377–3:34, 1988), LCRs have the ability to overcome such position effects when linked directly to transgenes (Grosveld et al., supra). Numerous LCRs have been defined in the art, including but not limited to the β-globin and CD2 LCRs (Greaves et al., 1989), the macrophage-specific lysozyme LCR (Bonifer et al., 1985, 1990), and a class II MHC LCR (Carson et al., Nucleic Acids Res. 21, 9:2065–2072, 1993).

Delivery of a Vector or Nucleic Acid According to the Invention

Targeted delivery to cells or precursor cell types can be achieved by receptor-mediated gene transfer using a delivery vehicle containing a ligand which is targeted to a cognate receptor on a cell surface. Targeting ligands useful according to the invention include but are not limited to the following: (a) for T-cells: an anti-CD7 monoclonal antibody or anti-T cell receptor antibody; (b) for monocytes and macrophages, an anti-CD14 monoclonal antibody; (c) for dendritic cells, a mannose receptor binding ligand; (d) for hemopoietic stem cells: anti-CD34 monoclonal antibody, or the Stem cell factor (c-Kit or CDt 17), or flk-2 ligand (human homolog STK-1); and (e) for MHC class II bearing cells: an antibody that is specific for the constant region of MHC class II proteins or a ligand that binds MHC class II, for example soluble CD4.

Targeted delivery vehicles for delivery of DNA constructs to cells are known in the art and include DNA/polycation complexes which are specific for a cell surface receptor, as described in, for example, Wu and Wu (1988) *J. Biol. Chem* 263:14621; Wilson et al. (1992) *J. Biol. Chem*. 267:963–967; and U.S. Pat. No. 5,166,320. A particularly preferred mode of delivery employs a self-assembling viruslike particle which includes a DNA or RNA according to the invention and condensing peptides which are heteropeptides with respect to their amino acid composition (i.e., containing at least two different amino acids which are preferably basic and thus good DNA binding and DNA condensing peptides) and which have low polydispersion (i.e., a given preparation of a heteropeptide which has low polydispersion contains peptides of very similar, if not identical lengths, such that the preparation is essentially monodispersed).

The invention thus also relates to a nucleic acid construct which is delivered to a cell using a synthetic virus like particle for transfecting nucleic acid into a mammalian cell. The synthetic virus like particle includes a recombinant nucleic acid, a plurality of nucleic acid condensing peptides, the peptides being non-covalently associated with the recombinant nucleic acid such that the nucleic acid is in condensed form, wherein each nucleic acid condensing peptide is a heteropeptide, and plurality of nucleic acid condensing peptides has low polydispersion.

The plural nucleic acid condensing peptides may include a first nucleic acid condensing peptide and a second nucleic acid condensing peptide, wherein the first nucleic acid condensing peptide comprises a first functional group covalently bound thereto. The first nucleic acid condensing peptide may further include a second functional group which may be directly bound to the peptide or may be covalently bound to the first functional group, where the first functional group is bound to the peptide. Alternatively, a second nucleic acid condensing peptide also may include a second functional group covalently bound thereto, the second functional group being different from the first functional group. The first and second nucleic acid condensing peptides may have identical or different amino acid sequences.

The functional groups which are bound to peptides useful according to the invention include a ligand that is an antigenic peptide, such as influenza nucleoprotein (NP) or a ligand that targets a specific cell-type such as a monoclonal antibody, insulin, transferrin, asialoglycoprotein, or a sugar. The ligand thus may target cells in a non-specific manner or in a specific manner that is restricted with respect to cell type.

The first nucleic acid condensing peptide may include 8–24 positively charged amino acid side groups; for example, the number of positively charged amino acid side groups may be in the range of 12–18.

A nucleic acid condensing peptide which is particularly useful for condensing the nucleic acid construct and therefore for delivering nucleic acid to a cell includes an amino acid sequence of the generic formula

$$NH_2-A-(X_1X_2Y_1Y_2)_nX_3X_4-(Z_1Z_2Z_3Z_4)$$
$$(X_5X_6Y_3Y_4)_mX_7X_8BCOOH$$

wherein each of $X_{1-8}$ is, independently, an amino acid having a positively charged group on the side chain; wherein each of $Y_{1-4}$ is, independently, a naturally occurring amino acid which promotes alpha helix formation; wherein each of $Z_{1-4}$ is, independently, a naturally occurring amino acid with at least 3 amino acids having a high propensity to form a stabilized turn structure; wherein A is an amino-terminal serine or threonine residue; wherein B is any amino acid; and wherein n=2–4 and m=2.

Other peptides are those wherein each of $X_{1-8}$ is, independently, lysine, arginine, 2.4-diamino-butyric acid or ornithine; wherein each of $Y_{1-4}$ is, independently, glutamic acid, alanine, leucine, methionine, glutamine, tryptophan or histidine; wherein each of $Z_{1-4}$ is, independently, asparagine, glycine, praline, serine, and aspartic acid; wherein B is any one of alanine, glutamic acid or cysteine.

Peptides which fall within this generic sequence include:

NBC2 H-KAVKPKAAKPKKPKKKRKVEKKSPKKA-KKPAAC(Acm)-OH; [SEQ ID NO: 23]

NBC8 H-KKSPKKAKKPAAKKSPKKAKKPAAC (Acm)-OH[SEQ ID NO: 24],

NBC9 H-KKSPKKAKKPAAKKSPKKAKKPAAKKSP-KKAKKPAAC(Acm)-[SEQ ID NO: 25] OH;

NBC10 [SEQ ID NO: 26]

H-KKSPKKAKKPAAKKSPKKAKKPAAKKSPKKAK-KPAAKKSPKKAKKP AAC(Acm)-OH.

NBC7 TRRAWRRAKRRAARCGVSARRAAWRRE-OH[SEQ ID NO: 17]; and

NBC11 [SEQ ID NO: 17] H-TKKAWKKABKKAAK-KCGVSAKKAAKKAWKKA-NH$_2$.

Host Cells Useful According to the Invention

The type of host cell useful according to the invention may be, for instance, prokaryotic or eukaryotic, e.g., a mincellular organism in culture or a mammalian cell in vivo. The host cell may also be a cell that can be introduced into a patient so that expression of a nucleic acid molecule of the invention occurs in vivo. Such a cell could be a cell previously removed from a patient for subsequent re-introduction, with the vector delivered to the cells in vivo or ex vivo. Cells which are particularly preferred targets for delivery of a nucleic acid of the invention are, for patients infected with HIV or susceptible to such infection, cells which HIV targets, e.g., T cells, and in addition, precursor T cells, hematopoietic Stem cells, and macrophages, and monocytes.

Vectors Containing Additional Anti-HIV Elements According to the Invention

Recent clinical trials provide strong evidence that combination therapy is more effective in blocking HIV replication and significantly suppresses the emergence of drug resistant escape mutants. In addition, therefore, a molecule according to the invention may also comprise one or more additional anti-HIV agents. An example of such a combinational agent might be a single RNA molecule comprising both a Rev decoy according to the invention and an anti-Tat decoy.

To increase further the HIV inhibitory potency of the RRE decoys described above in accordance with combination therapy according to the invention, additional constructs were prepared in which sequences designed to inhibit Tat-mediated transactivation of the HIV LTR as well as Rev function were incorporated. It is contemplated according to the invention that any combination anti-HIV therapy may be performed according to the invention, the three types of anti-Tat constructs described below being representative of such combination therapies.

Figures 13, 13A:
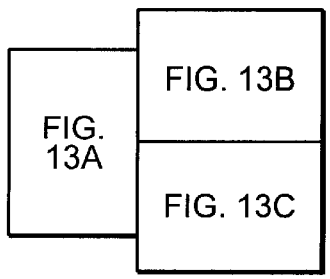
FIG. 13 shows the TAR[SEQ ID NO: 18], hammerhead ribozymes[SEQ ID NO: 19], and antisense sequences used in combinational vectors.
Figure 13B:
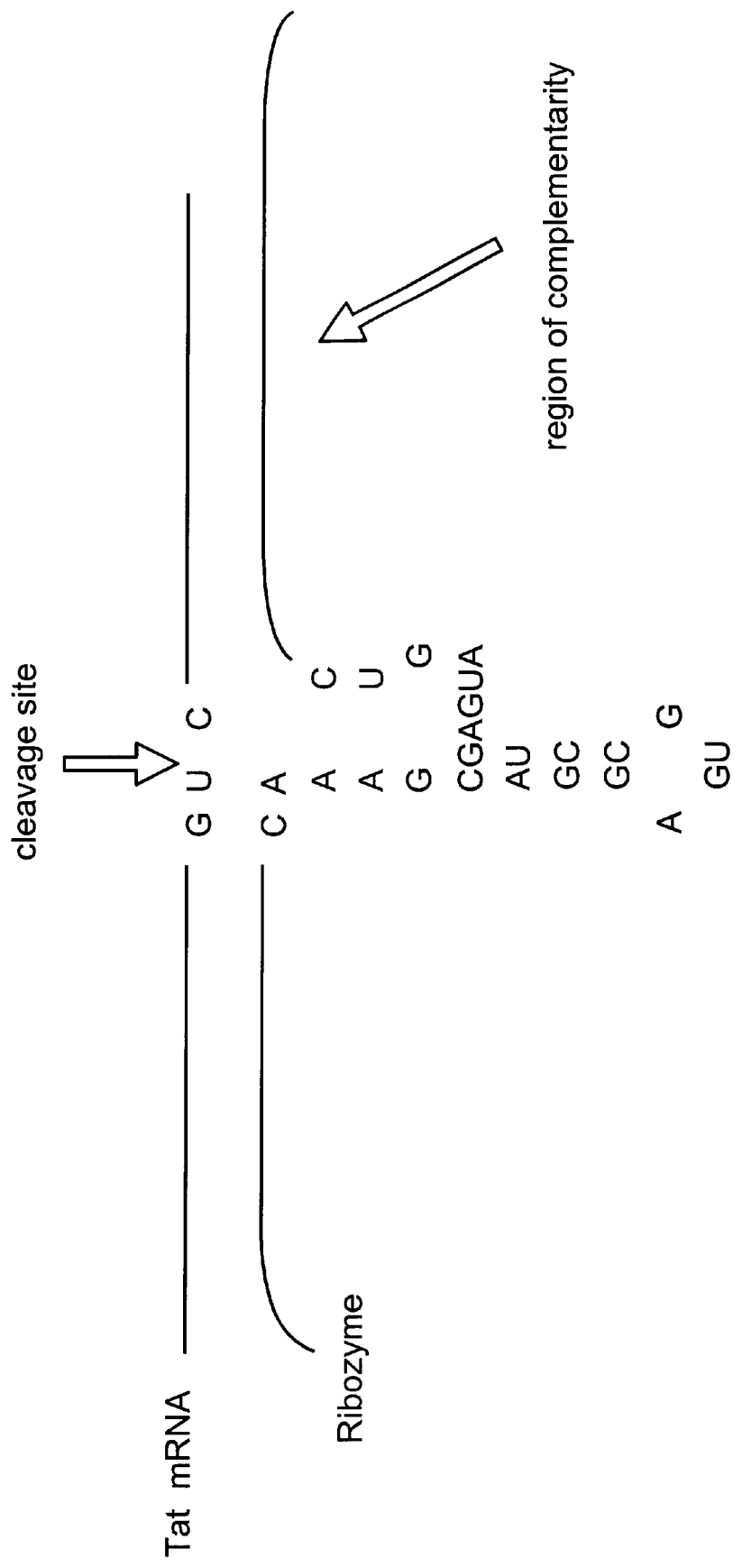
Figure 13C:
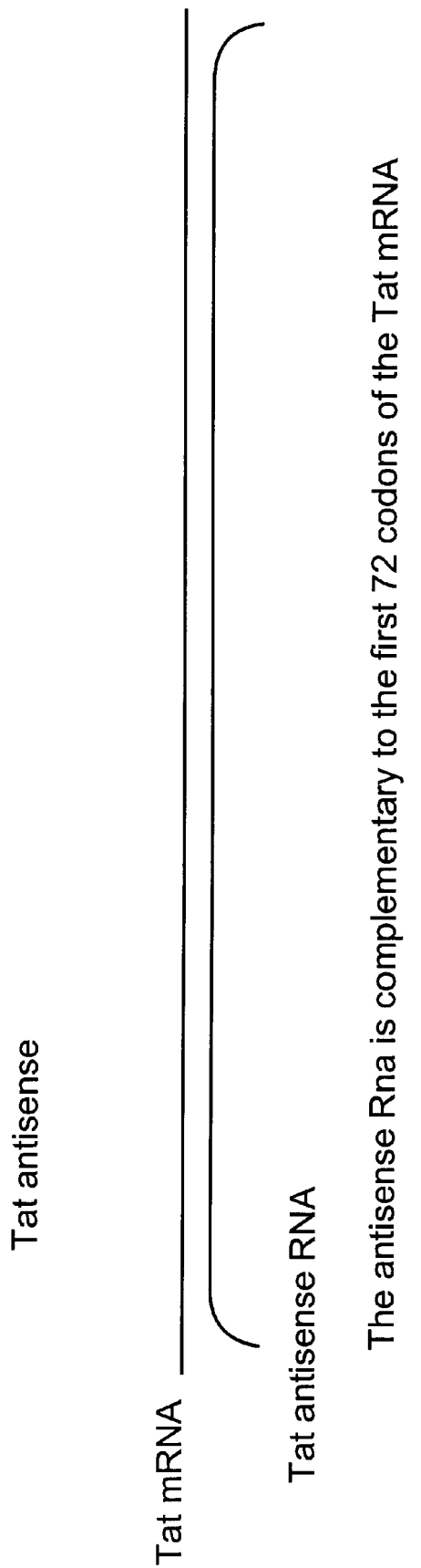

Three combination vectors were prepared and tested, as described below (see FIG. 13): (i) the Tat responsive (TAR) element from [SEQ ID NO: 18] the HIV-2 LTR (Emennan et al., 1987); (ii) hammerhead ribozymes [SEQ ID NO: 19] designed to cleave within the Tat open reading frame; and (iii) an anti-Tat antisense sequence, as described in detail in Examples 3–5.

Determination of Efficacy of RNA Molecules of the Invention

The relative efficacy of the transcripts containing Rev decoys of the present invention in inhibiting HIV replication is determined according to a number of assays, as follows.
(i) HIV Spread assay on Jurkat T-cells.

In an 11V spread assay, transfected Jurkat T-cell pools expressing the different inhibitory transcripts are infected at a low multiplicity of infection (moi) and the efficiency of spread of virus through the majority uninfected cells is monitored over a 3 week period and compared to control cells. Two control cell-lines are used, one being non-transfected and the other being transfected with an expression vector lacking decoy inserts. An example of effective inhibition of HIV replication is provided in Example 14.
(ii) Efficacy in PBMC and SCID-HU Models.

Inhibition of HID replication observed in continuous T cell lines such as Jurkat and CEM provides evidence that the Rev decoy-expressing constructs are likely also to be effective in primary cells. Efficacy in primary cells could be demonstrated at different levels, initially in cultured transduced primary cells, in SCID-HU mice which will provide an approximation to the in vivo situation and finally in HIV-infected patients. In each case, the decoy-expressing plasmid is introduced into primary T cells. For this purpose, a defective recombinant retroviruses may be used to provide a high transfection efficiency and efficient integration to permit stable inheritance of the plasmid. A moloney-based vector may be used. To not exceed the packaging capacity of the vector, a 2 kb locus control region of the CD2 locus is used.
(iii) Ex vivo Transduction of Decoy Constructs.

Decoy-expressing constructs of the invention may be demonstrated to be effective in CD4+ T cells derived from HIV infected patients as follows. CD4+ T cells are isolated from blood aphoresed from HIV-infected/pre-AIDS patients, and transduced with a high titre retrovirus expressing the decoy under drug selection. Surviving cells may be analysed in two ways; (i) by exposure to exogenous virus, e.g., PBMC-adapted MN and measurement of virus produced by p24 ELISA compared to cells transduced with an empty control virus and (ii) co-culture with non-infected CD4+T cells to determine the degree of endogenous virus spread into the non-infected cells, again using a p24 ELISA to measure virus production.
(iv) Testing of Decoy Constructs in Mouse Models of HIV Infection.

Mouse models of HIV infection may be used as in vivo models for testing and demonstration of efficacy of the decoy constructs according to the invention. Such models include SCID-hu and NOD/Lt3z-scid mice. See McCune et al (1991) Ann. Rev. Immunol. 9, 399; Mosier et al (1991) Science 251, 791; and Shultz et al (1995) J. Immunol 154, 180. Where long-term experiments are contemplated, NOD/LtSz-scid mice are preferred as these mice also lack innate immunity.

Briefly, non-HIV infected primary human CD4+ T cells are transduced with decoy-expressing vector or a control vector that lacks the decoy sequences. $1\times10^7$–$4\times16^7$ transduced cells are then introduced into SCID mice by intraperitoneal injection. Mice are then challenged with cell free virus or with virus-infected autologous T cells by IP injection. The spread of infection may be evaluated by, e.g., (i) co-culture of lymphoid tissue with fresh human PBLs and measurement of virus produced (ii) in situ hybridization of PB T cells or spleen using an HIV-specific probe.

Alternatively, a 50:50 mix of decoy expressing and empty vector containing cells may be infused into the animal, the animal infected with HIV, and the viral load monitored by RT-PCR. The ratio of decoy-expressing/empty vector containing cells is then monitored by in situ hybridisation. If the decoy is effective, then the ratio of decoy-expressing/empty vector containing cells will increase in virus-infected cells.
(v) Ex vivo Transduction of Cells with Decoy Sequence and Introduction into HIV Patients.

CD4+ T cells are isolated, transduced, selected, expanded, and reinfused into the patient. Viral load is measured by RT-PCR. Infection of decoy-expressing cells may be monitored via in situ hybridisation.

Determination of Inhibition of HIV Viral Titer According to the Invention

The efficacy of RNA molecules of the invention also can be determined by determining the inhibition of HIV viral titer, as follows. In addition, an "effective amount" of a nucleic acid molecule of the invention is determined using the HIV viral titer, as described below.

Serial virus dilutions are applied to Jurkat T-cells in 24 well plates. 7 days after infection, cell free supernatant is harvested from each well and virus levels are determined by assaying levels of two HIV proteins: p24 and reverse transcriptase (RT). p24 levels are determined with a sandwich ELISA (DuPont NEN, HIV p24 core profile ELISA, catalogue no. NEK-060B) and RT levels by a non-radioactive enzymic assay (RT assay from Amersham International, PolyR(A) RT SPA enzyme assay, catalogue no. NK-9020). Both kits are used according to the manufacturers' instructions.

The $TCID_{50}$ is defined as the dilution which results in productive virus production in 50% of wells.

To determine a moi for HIV-IIIB which results in progressive virus spread throughout Jurkat cultures, cells are infected with 100, 1000 and 10,000×T $CID_{50}$ and processed as follows. After a 16 hour adsorption step, infected cells are collected by centrifugation and resuspended in fresh growth medium to remove non-adsorbed virus and virus debris. Virus release is then monitored over successive 3 day periods by resuspending the infected cell cultures at the end of each 3 day period in fresh medium and assaying levels of p24 and RT in the cell free supernatants taken. An moi is selected to challenge cells expressing candidate decoys in the above HIV spread assay.

The spread assay results indicate that molecules according to the present invention are able to inhibit HIV replication.

DOSAGE, MODE OF ADMINISTRATION AND PHARMACEUTICAL FORMULATION

Nucleic acids of the invention are useful in therapy, and may be administered to a mammal, preferably a human patient, for the purpose of treatment of HIV infection.

Particular therapeutic uses include the treatment of a patient infected with HIV and the prophylactic treatment of individuals at risk of HIV infection. As described hereinabove, nucleic acids also may be used in association with other therapeutic agents or pharmaceuticals.

According to the invention, an effective amount of a nucleic acid molecule of the invention is administered to an HIV-infected patient or to an individual at risk of HIV infection to inhibit replication of the virus. For an individual at risk for HIV infection, a prophylactic amount of a nucleic acid of the invention is administered. An "effective amount" of a nucleic acid molecule of the invention is determined via the ability of the administered dose to reduce HIV viral titer. An assay for determining HIV viral titer is described below.

Serial dilutions of serum from a patient to which a given dose of a nucleic acid molecule of the invention (or a given dose of cells transfected with a DNA of the invention or a given dose of a delivery vehicle containing a DNA or RNA of the invention), that is serum suspected of containing a reduced amount of HIV as a result of treatment, are applied to T-cells in 24 well plates. 7 days after infection, cell free supernatant is harvested from each well and virus levels are determined by assaying levels of two HIV proteins: p24 and reverse transcriptase (RT). p24 levels and RT levels are determined as described above. The TCID, is defined as the dilution which results in productive virus infection in 50% of wells. An "effective amount" of a molecule of the invention will be that amount which reduces the viral titer by at least 50% within 10 days after administration of the nucleic acid molecule of the invention, and preferably by at least 75%. Of course, any reduction in viral titer as a result of such administration is desirable according to the invention. A "prophylactic amount" of a nucleic acid molecule will be less than an "effective amount" as used in treatment of HIV infection; generally, a prophylactic amount is in the range of 1–10%, and preferably about 2–5% of an effective amount. A prophylactic amount of a nucleic acid molecule of the invention is that amount which results in a continued inability to detect an HIV titer in an individual at-risk for HIV infection.

A nucleic acid according to the invention may be delivered to cells cultured ex vivo prior to reinfusion of the transfected cells into the patient or the gene may be delivered in a nucleic acid delivery vehicle complex by direct in vivo injection into the patient or in a body area rich in the target cells. The in vivo injection may be made subcutaneously, intravenously, intramuscularly or intraperitoneally. Techniques for ex vivo and in vivo gene therapy are known to those skilled in the art. Generally, the compositions are administered in a manner compatible with the dosage formulation, and in such amount as will be prophylactically and/or therapeutically effective. The quantity to be administered depends on the subject to be treated, including, e.g., whether the subject has been exposed to HIV or infected with HIV, or is afflicted with AIDS, and the degree of protection desired. Suitable dosage ranges are on the order of, where a dose of RNA molecules is administered, in the range of 0.1 ug–100 ug/kg body weight, a dose of DNA encoding an RNA molecule of the invention, in the range of 0.00 $\mu$g–10 ug/kg body weight, a dose of a delivery vehicle containing an RNA or DNA according to the invention, in the range of 1 ug–10 ug/kg body weight; and where ex vivo transfected cells are administered to a patient $10^5$–$10^7$, and optionally $10^6$–$10^7$ cells are administered in a single dose. Suitable regimens for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of a composition of this invention will depend, inter alia, upon the administration schedule, the unit dose of nucleic acid administered or expressed by an encoding nucleic acid that is administered, whether the compositions are administered in combination with other therapeutic agents, the immune status and health of the recipient, and the therapeutic activity of the particular nuclei acid molecule, delivery complex, or ex vivo transfected cell.

Compositions of the invention can be given in a single dose schedule, or in a multiple dose schedule. A multiple dose schedule is one in which a primary course of administration can include 1–10 separate doses, followed by other doses given at subsequent time intervals required to maintain and or reinforce the immune response, for example, at 1–4 months for a second dose, and if needed, a subsequent dose(s) after several months. Periodic boosters at intervals of 1–5 years, usually 3 years, may be desirable to maintain the desired levels of treatment.

Pharmaceutical compositions useful according to the invention will include a nucleic acid of the invention admixed with a pharmaceutically acceptable carrier. Such carriers may include, for example, one or more of water, saline, phosphate buffered saline, dextrose, glycerol, ethanol, or the like and combinations thereof In addition, if desired, the formulation can contain minor amounts of auxiliary substances such as wetting or emulsifying agents and pH buffering agents.

EXAMPLE 1

Construction of LCR-based vectors

Figure 12:
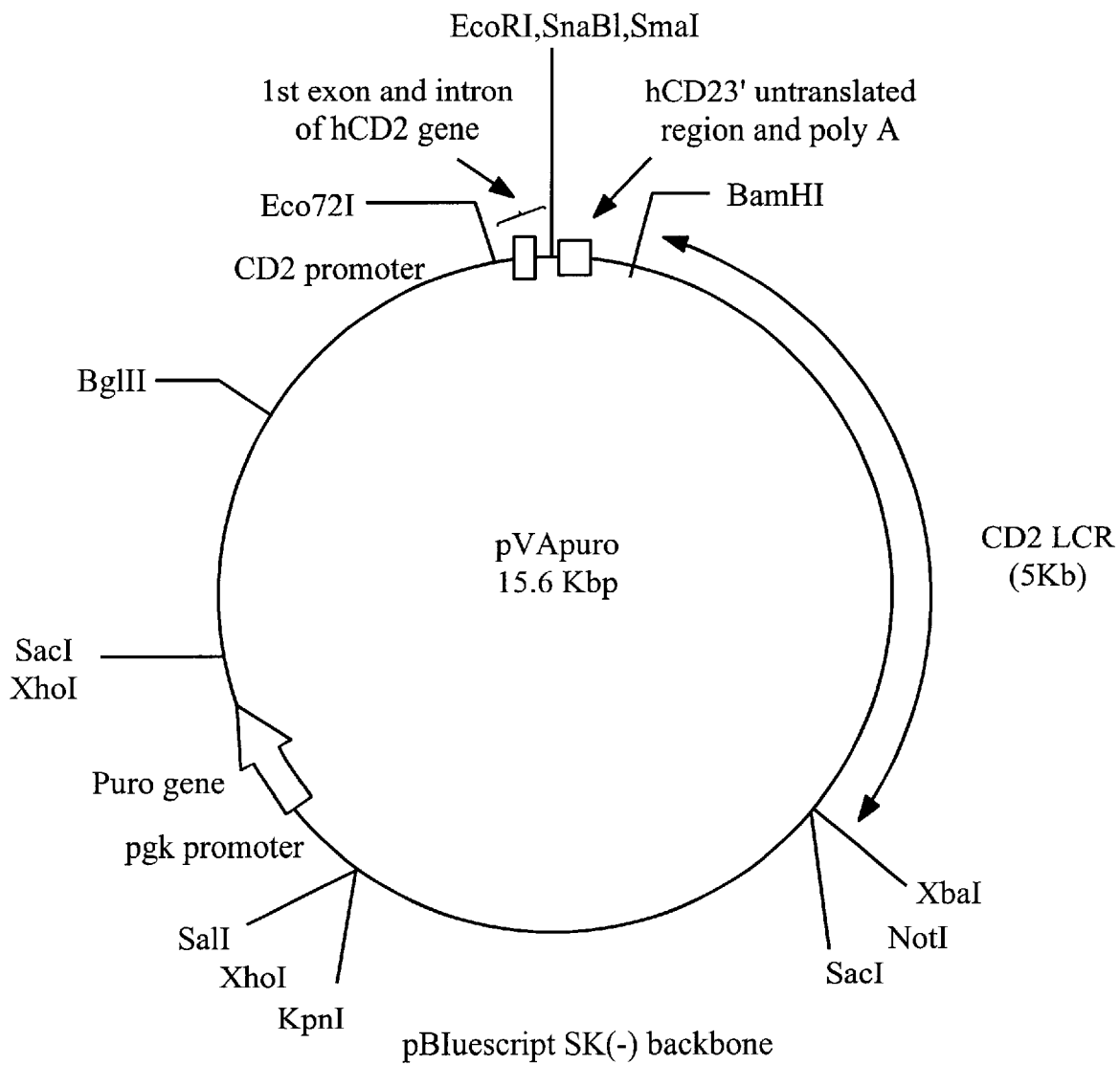
FIG. 12 shows vector pVApuro.

The pVApuro vector (see FIG. 12) was constructed in order to obtain T-cell specific expression of transcripts containing Rev binding molecules according to the present invention. This vector comprises the human CD2 promoter, a truncated CD2 gene containing three unique restriction sites for insertion of a molecule of the invention, and the human CD2 LCR, 3' to the unique restriction sites. The CD2 LCR comprises elements conferring T-cell specific expression and chromatin opening domains that allow expression independent of the site of integration. pVApuro was derived from the VA CD2 expression cassette (Zhumabekov et al., 1995) by insertion of a puromycin resistance gene between the KpnI and blunt-ended NotI site of the cassette. The KpnI and blunt-ended DNA fragment encoding the puromycin resistance gene was the KpnI and blunt-ended SalI fragment from pPGKpuro. pPGKpuro comprises the PGK promoter (EcoRI-TaqI fragment (Adra et al.)), the polyA signal from bovine growth hormone (Pfarr et al.), and the puromycin resistance gene from pBABEpuro (HindIII-ClaI fragment (Morgenstern & Land)).

The RRE was cloned as an EcoRI-SmaI fragment from pRREF (pUC19 containing the RRE sequence between EcoRI and SmaI sites) into EcoRI-SmaI digested pVApuro to create vector pVA/RRE.

DNA oligonucleotide RWZ2 [SEQ ID NO: 29] TOP was constructed which contains a sequence corresponding to the RWZ2 sequence [SEQ ID NO: 4] (shown underlined):

5'-AAT TCG GCA GAC CGG AAT TCT TGG GCG CAG CGT CAT TGA CGC TCG GGT ACAD, TCG GAA TTC CGG TCT GCC C-3' [SEQ ID NO: 29]

Oligonucleotide RWZ2-BOTTOM [SEQ ID NO: 30] is complimentary to RWZ2-TOP:

5'-G GGC AGA CCG GAA TTC CGA TGT ACC GCA GCG TCA ATG ACG CTG CGC CCA AGA ATT CCG GTC TGC CG-3' [SEQ ID NO: 30]

and when these two oligonucleotides are annealed a double-stranded structure is formed with a single-stranded overhang of AATT. This structure is compatible at the 5' end of RWZ2-TOP [SEQ ID NO: 29] with EcoRI digested DNA and at the 3' end with SmaI digested DNA and was cloned directly into EcoRI/SmaI digested pVApuro to create vector pVA/RWZ2.

Similarly, DNA oligonucleotide RWZ6-TOP containing [SEQ ID NO: 31] a sequence corresponding to RWZ6 was prepared:

5'-AAT TCG GCA GAC CGG AAT TCT TGG GCG CAG CGT CAT TGA CCGC TCR GGTT ACD, GGC CAG ATT ATC TGA TAA GAA TTC CGG TCT GCC C-31 [SEQ ID NO: 31]

RWZ6-BOTTOM [SEQ ID NO: 32] is complementary to this:

5'-G GGC AGA CCG GAA TTC TTA TCA GAT AAT CTG GCC TGT ACC GCA GCG TCA ATG ACG CTG CGC CCA AGA ATT CCG GTC TGC CG-3' [SEQ ID NO: 32]

and these two oligonucleotides also form a double-stranded structure with a single-stranded overhang of AATT. This double-stranded structure was inserted into EcoRI/SmaI digested pBluescript-KS(−) (Stratagene) to create pKS/RWZ6. RWZ6 [SEQ ID NO: 8] was then excised as an EcoRV-SmaI fragment and cloned into SmaI digested pVApuro to create vector pVA/RWZ6.

EXAMPLE 2

Construction of an episomal vector.

A fundamental parameter in gene therapy is the duration of expression of a given therapeutic gene product. In dividing target cells this is limited principally by the dilution and eventual loss of introduced non-replicating genetic material. Such vectors have been derived from EBV (Yates et al., 1985) and from BPV (Cooper & Miron, 1993). These vectors replicate to give copy numbers of up to about 100 per cell. Both features can be usefully combined with the molecules of the present invention to provide stable expression in dividing T-cells and increased steady-state expression levels of transcripts containing the Rev decoys through a gene dosage effect.

Figure 15:
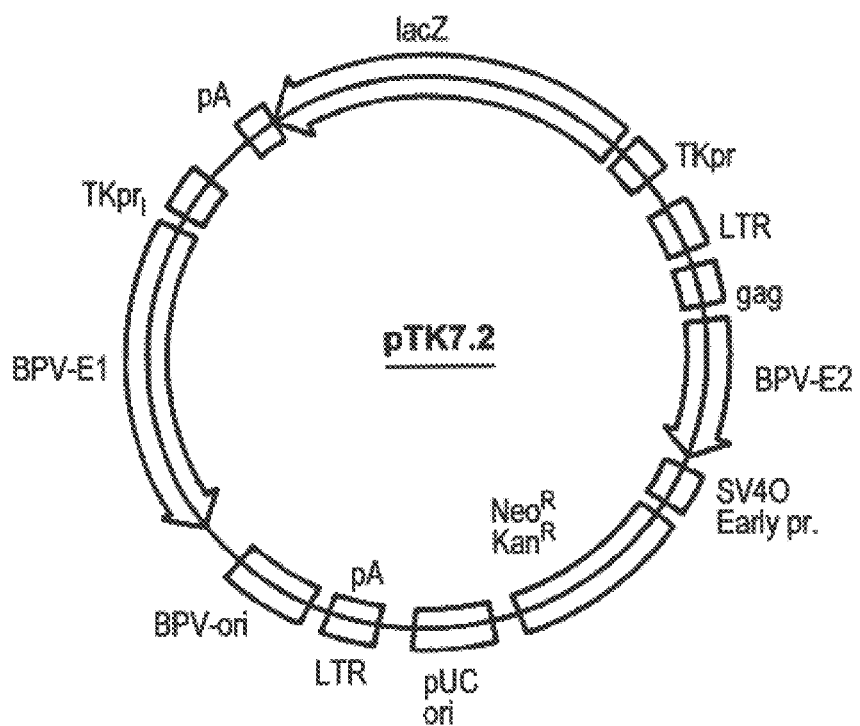
FIG. 15 shows the vector pTK7.2.

A BPV based vector was derived from pTK7.2, which is a BPV-1 based expression vector containing BPV-1 origin of replication, BPV-1 E2 ORF under control of the MoMSV LTR, BPV-1 E1ORF under control of the weak HSV thymidine kinase promoter, and lacZ under control of RSV LTR (FIG. 15). The β-galactosidase gene was removed from pTK7.2 by a HindIII digest and replaced with a multicloning sequence (MCS) created by annealing the primers:

5'-AGC TTA CGA TCG ACC GCG GAG CGG CCG CAG GGC-3' [SEQ ID NO: 33]

Figure 16:
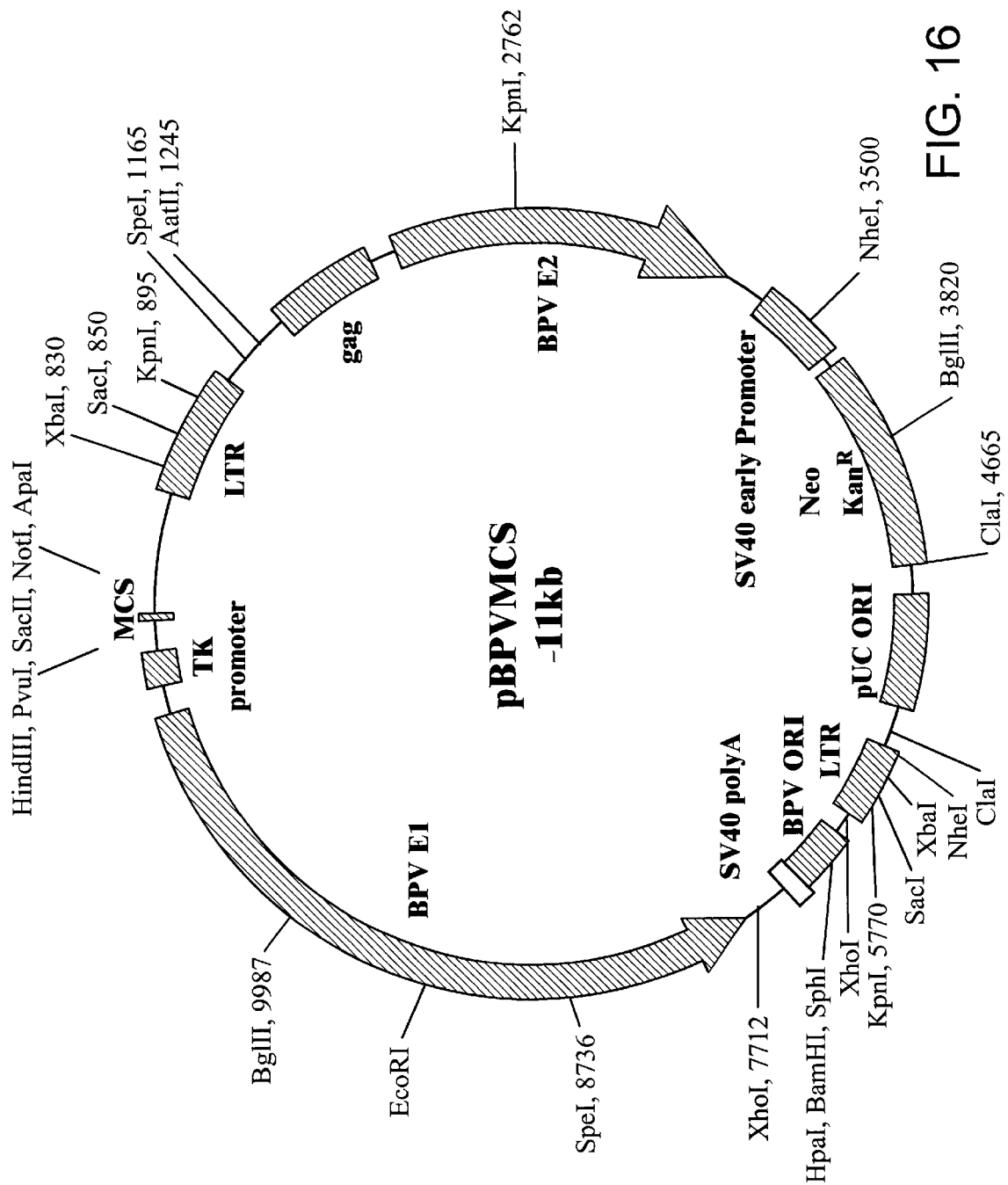
FIG. 16 shoves the vector pBPV.MCS, derived from pTK7.2.

5'-AGC TGG GCC CTG CGG CCG CTC CGC GGT CGA TCG-3' [SEQ ID NO: 34]

to provide unique HindIII, PvuI, SacII and ApaI sites. This vector is termed pBPV.MCS (FIG. 16).

EXAMPLE 3

Combination vectors encoding the Tat-responsive element.

The TAR element [SEQ ID NO: 18] of the HIV-2 LTR was isolated using PCR. The primers used were complementary to regions 5' to the TAR element of HIV-2 (5'-CGG CGG TGA ATT CGT CGC TCT GCG GAG A-3'[SEQ ID NO: 35]) and 3' to the TAR element of HIV-2 (5'-TGG AAT TCG GCC GAC CGG CCA AGT GCT G-3'[SEQ ID NO: 36]). The PCR product generated was digested with EcoRI to create an EcoRI TAR fragment.

This TAR fragment was cloned into EcoRI digested pVApuro to create vector pVA/TAR. Vector pVA/TAR-RRE was created by insertion of the TAR fragment into EcoRI digested pVA/RRE. The RWZ6-containing EcoRV-SmaI fragment from pKS/RWZ6 [SEQ ID NO: 8] was cloned into SmaI digested pVA/TAR to create vector pVA/TAR-RWZ6. Vector pKS/RWZ2 [SEQ ID NO: 4] was prepared by an analogous method to pKS/RWZ6. The RWZ2-containing EcoRV-SmaI fragment from pKS/RWZ2 was cloned into SmaI digested pVA/TAR to create vector pVA/TAR-RWZ2. The orientation of TAR [SEQ ID NO: 18] in all these vectors was determined by analytical PCR and confirmed by DNA sequencing.

EXAMPLE 4

Combination constructs encoding anti-Tat ribozymes.

Vector pTat was constructed by inserting the first 216 nucleotides of the Tat gene (coding for amino acids 1–72) Ratner. et al., 1985) into pBluescript KS(−). These 216 nucleotides were excised as an EcoRI-SalI fragment from pCMVTat72 and cloned into the corresponding sites of pBluescript KS(−). A hammerhead ribozyme (Crisell et al., 1993) was designed which targets the GTC sequence spanning codons 16 and 17 of the Tat gene. The anti-Tat ribozyme was constructed by blunt-end ligation of two PCR products (see FIG. 13).

PCR products were generated using pTat as the template and the primer pairs TXoli1/T3primer or TXoli2/T7primer. The PCR products were ligated and cleaved with EcoRI and SalI. The correct band was gel purified and cloned into pBluescript KS(−) to create vector pTatRzFull. The TatRz-Full fragment was excised from this vector by KpnI digestion, blunt-ending, EcoRI digestion, and the resulting fragment was cloned into EcoRI-SmaI digested pVApuro to create combinational vector pVA/TatRzFull.

Fragments TatRz77 and TatRz33 were created by PCR amplification from pTatRzFull using the primer pairs TXoli15/TXoli16 and TXoli13/TXoli14, respectively:

TXoli13
5'-CGGGATCCGTCGACCTAGACTAGAGCCCTG-3' [SEQ ID NO: 37]
TXoli14 5'-GCGAATTCAATAGCAATTGGTACA-3' [SEQ ID NO: 38]
TXoli15
5'-CGGATCCGTCGACGGCGTTACTCGACAGAG-3' [SEQ ID NO: 39]
TXoli16 5'-CCGAATTCGGCTTTTGTTATGAAAC-3' [SEQ ID NO: 40]

The resulting PCR products were purified, digested with EcoRI and BamHI, then ligated into EcoRI-BamHI digested pBluescript KS(−) to create pTatRz77 and pTatRz33. The T0at ribozyme fragments of pTatRz77 and pTatRz33 were excised by BamHI digestion, blunt-ending, and were subjected to EcoRI digestion. The resulting fragments were cloned into EcoRI-SmaI digested pVApuro to create combinational vectors pVA/TatRz77 and pVa/TatRz33, respectively.

EXAMPLE 5

Combination constructs encoding anti-Tat antisense RNAs.

The Tat gene fragment containing the first 216 nucleotides was excised from pCMVTat72 by SalI digestion, blunt-ending, and EcoRI digestion. This fragment was then cloned into EcoRI-SnaBI digested pVA.pitro to create pVA.antisenseTat.

EXAMPLE 6

Figure 14:
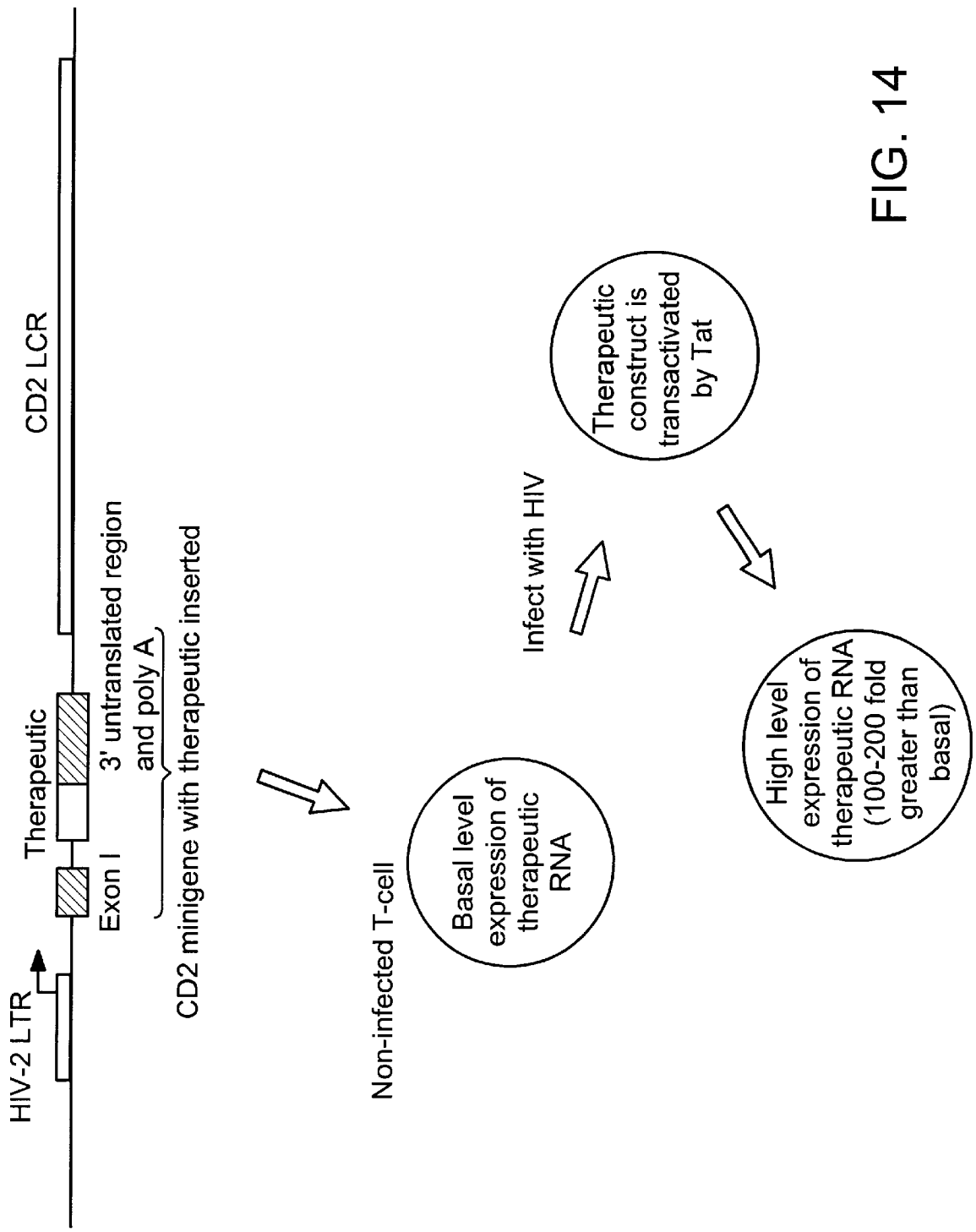
FIG. 14 shows the construction of pHIV-2LTR.VA.puro and illustrates its mode of action.

The success of decoy and ribozyme strategies is dependent upon the achievement of functional concentrations of the molecules, in the present case a mRNA decoy, within the target cells. To obtain levels of expression in excess of that obtained with the pVA expression vector described above, a derivative vector was prepared using the HIV-2 LTR to drive transcription in combination with the CD2 LCR (see FIG. 14). The plasmid was constructed as follows. The HIV-2 LTR was cloned into pBluescript as a KpnI-BamHI fragment, re-excised by BamHI digestion, blunt-ending, and then BglII-digestion to produce a fragment with a sticky BglII end and a blunt end. This fragment was cloned into BglII-Eco72I digested pVApuro to create vector pHIV-2LTR.VA.puro.

The decoy constructs described above were cloned into this vector as follows. The expression cassettes were excised as BglII-XbaI fragments and cloned into pKSP, a pBluescript II KS(+) derivative containing a unique PvuI site at the SacI end of the MCS. This site was introduced by digesting pBluescript II KS(+) with SacI and inserting a double-stranded DNA fragment produced by annealing the two oligonucleotides:

5'-AAACGATCGAAGAGCT-3' [SEQ ID NO: 41] & 5'-CTTCGATCGTTTAGCT-3' [SEQ ID NO: 42]. The cassettes were then excised from this intermediate as ApaI-PvuI fragments and cloned into pBPV.MCS.

Earlier work (EP-A-0689602; Brady et al., 1994) identified a subfragment of the HIV-2 LTR that exhibits a decreased basal expression level while retaining full responsiveness to transactivation by Tat (100–200 fold) and showed that, at least in transgenic mice, this basal expression is largely restricted to lymphoid tissues. This truncated promoter could be used to replace the full-length HIV2 LTR promoter in the vector, thus offering the potential benefits of high decoy concentration restricted to HIV infected cells.

EXAMPLE 7

It may be advantageous to provide a decoy molecule of the invention within the wildtype RRE context. This decoy/wildtype chimeric RRE is believed to increase the maximum number of molecules that bind to a decoy molecule of the invention by providing additional wildtype sequences for Rev binding. The wildtype RRE [SEQ ID NO: 1] is believed to bind up to 12 Rev molecules. The chimeric molecule therefore combines the advantages of co-operative binding of the decoy molecules of the invention and increased capacity to bind Rev, and is believed to provide more effective sequestration of Rev and thus more effective inhibition of HIV replication.

A chimeric decoy/wildtype RRE may be made by incorporation into the RRE of the essential modifications used to create a decoy of the invention. For example, the decoys RWZ2 [SEQ ID NO: 11] and RWZ6 [SEQ ID NO: 8] contain a truncated stem IIC. Compared to wildtype RRE, this decoy lacks 3 three nucleotides on either side of the apical UUA, respectively nucleotides 141–143 and 147–149. These nucleotides in the wildtype RRE [SEQ ID NO: 1] may be removed by two successive in vitro mutagenesis steps using mutagenic oligonucleotides straddling the deletion sites, and the wt RRE cloned in an M13 phage vector as target single strand DNA. The construction of chimeric decoy/wildtype RRE molecules according to the invention may be achieved using similar strategies and conventional cloning techniques.

Decoy sequences prepared according to the invention also may include multiple contiguous copies of the minimal decoy sequences described herein. These multiple copy sequences may be prepared by inserting several individual sequences in tandem into a vector molecule using standard cloning methods. The multi-site contiguous sequence will be of sufficient length so as to permit appropriate folding of individual Rev binding sites along the length of the encoded RNA.

EXAMPLE 8

Vectors according to the invention which encode RNA molecules of the invention may be modified so as to contain a sequence that increases steady state RNA levels. An example of such a sequence is the human beta-globin 3' UTR.

Where a high level of decoy-containing RNA is desirable to bind Rev, the CD2 LCR/HIV-2 LTR-driven vector (described above) may be combined with the 3' untranslated region of the human beta globin gene. The presence of the beta globin 3' untranslated region is believed to produce an increase in expression levels by mediating highly efficient polyadenylation of nascent transcripts.

The construct may be prepared, as follows. The CD2 3' UTR is removed from the decoy expressing construct by SmaI+BamHI digestion and replaced with an adaptor containing BamHI and PmeI sites to create a cloning intermediate, which has the CD2 3' UTR deleted. The beta-globin 3' UTR is excised from the globin region as a 1.2 kb BamHI-(StyI) fragment by StyI digestion, filled-in using T4 DNA, polymerase and BamHI digestion and cloned into pBluescript BamHI-SmaI. It is then excised as a BamHI-EcoRV fragment and cloned into BamHI-PmeI restricted 3' UTR-CD2 deletion construct.

Jurkat T cells stably transfected with constructs modified in this way generated 50–100 fold more decoy-containing transcript compared to cells stably transfected with the original construct.

EXAMPLE 9

It may be desirable according to the invention to provide constitutive expression of an RNA molecule according to the invention using a strong constitutive promoter. It also may be desirable to provide for expression of an RNA molecule of the invention in all cells which contain the transcript, that is, in uninfected as well as infected cells.

The HIV-2 LTR regulatory region may be replaced with a strong constitutive promoter to produce increased levels of decoy transcript in all cells containing the construct, i.e., in infected as well as uninfected cells, as decoy expression under control of a constitutive promoter is Tat-independent. Such constructs have been prepared wherein the decoy sequence is driven by the phosphoglycerate kinase and human beta-actin promoters. Optionally, in addition to including a strong constitutive promoter, the β-globin IVSII also may be included in the vector to ensure efficient processing.

The HIV-2 LTRP was excised from pHIV-2hGH1 (Brady et al., 1994, Proc. Nat. Acad. Sci. 91:365) as a BamHI-HindIII fragment and cloned into pBluescript cut with the same enzymes. It was then re-excised by BamHI digestion, T4 DNA polymerase treatment and BglII redigestion as a BglII-blunt end fragment and cloned into BglII-Eco72I cut pVApuro.

The murine PGK promoter was excised from pPKKpuro as a 450 bp TaqI fragment, blunted with T4 DNA polymerase and cloned into pBluescript cut with SmaI. It was then reexcised as a BamHI-EcoRV fragment and cloned into BglII-Eco72I cut pVApuro.

The promoter and first intron of human beta-actin were excised from pHbeta-APr-1neo (Proc. Nat. Acad. Sci. 84:4831, 1987) as a 4.3 kb EcoRI-SalI fragment and cloned into pBluescript as a BamHI-HincII fragment and cloned into BglII-Eco72I cut pVApuro.

Within these vectors, the polyA signal was obtained from the bovine growth hormone gene (Pfarr et al., DNA 5:115); the puro resistance gene as a HindIII-ClaI fragment of pBABEpuro (Morgenstern et al., Nucl. Acids Res. 18:12); the backbone vector was the pBluescript II KS(–) vector (Stratagene) with the XbaI site at position 677 changed to an XhoI site.

EXAMPLE 10

It may be advantageous according to the invention to provide for nuclear localization of an RNA molecule of the invention.

The frequency of interaction of the decoy transcript with Rev protein may be enhanced by colocalization of decoy and target protein within the cell. In the case of the decoys which are not colocalized to the nucleus, the anti-HIV activity may reflect either the interception of nascent protein or the activity of nascent/non fully processed decoy-containing RNA present in the nucleus or a combination of the two. It is believed that full nuclear localization of the decoy-containing RNA will significantly increase the efficiency of Rev sequestration. One method of achieving nuclear retention of an RNA transcript is to prevent the removal of intervening sequences. Decoy pre-mRNAs containing the beta-globin 3' UTR fragment described above modified so as to contain a non-functional splice donor sequence should accumulate in the nucleus.

The beta-globin 3' UTR useful according to this aspect of the invention contains a GT→AC splice donor mutation within a truncated IVSII. Truncation of the IVS from a O.9 kb fragment to an 89bp fragment is believed to result in a smaller construct retaining fall processing activity. The sequence of the human beta globin IVSII between the 3' end of exon II and the 5' end of exon III of the beta globin coding region is as follows. Human β(IVS)-89 bp fragment (underlined below and as follows)

5'GT GAG TCT ATG GGA CCC TTG ATG CCC GGG TAC AGT CCA AGC TAG GCC CTT TTG CTA ATC ATG TTC ATA CCT CTT ATC TTC CTC CCA CAG 3' [SEQ ID NO: 43] nucleotides. 20–108.

The 89 bp IVSII fragment may be carried in a larger fragment which encompasses a portion of the surrounding exons, as follows. Human β-globin BamHI/EcoRI fragment encompassing 3' end of exon II/IVSII/5' end of exon III 5'GGA TCC TGA GAA CTT CAG <u>GGT GAG TCT ATG GGA CCC TTG ATG CCC GGG TAC AGT CCA AGC TAG GCC CTT TTG CTA ATC ATG TTC ATA CCT CTT ATC TTC CTC CCA CAG</u> CTC CTG GGC AAC GTG CTG GTC TGT GTG CTG GCC CAT CAC TTT GGC AAA GAA TTC 3' [SEQ ID NO: 43] Inclusion of the GT→AC splice mutation in this fragment is believed to abrogate splicing activity. The splice donor mutant may be created from the wildtype sequence using site-directed mutagenesis, or other techniques available in the art. The 89 bp fragment containing the splice donor mutant is cloned into the decoy expressing constructs as follows.

The CD2 3' UTR deletion construct described above is linearized downstream of the decoy sequences with BamHI. The beta-globin 3' UTR fragment containing the splice donor mutant and truncated IVSII may be excised from as a 370 bp BamHI fragment and cloned into the CD2 3'UTR deletion mutant, and the proper orientation confirmed by EcoRI digestion.

EXAMPLE 11

Transfection of target cells

Jurkat cells (E6-1 clone, Weiss et al., 1984) or CEM cells (CCRF-CEM clone, eg. Cancer 18, 522–529 (1965)) were seeded at 4×10$^5$ cells/ml 24–36 hours before transfection. For each transfection, 2×10$^7$ cells were spun down, washed in 50 ml PBS (Life technologies), and resuspended in 900 μl electroporation buffer (EB: 25 mM HEPES, pH 7.4; 140 mM NaCl; 0.7 mM Na2HPO$_4$; filter-sterilized and stored at 4° C.).

The vector to be transfected into the target cells was linearized prior to transfection. Approximately 50 μg of linearized vector was ethanol precipitated, washed in 75% ethanol, and resuspended in 100 μl EB. This preparation was added to the target cells and the transfection mixture was left at room temperature for 10 minutes with occasional mixing.

The cells were electroporated at 250V, 950 μF. After being left at room temperature for a further 5 minutes they were then resuspended in 25 ml RF10 (RPMI-1640 (Sigma), 10% FBS, 1000U/ml penicillin, 0.1 mg/ml streptomycin). After 48 hours, transfected cells were selected using 5 ml RF10 containing 15 μg/ml puromycin. After a further 3 days incubation the medium was changed for conditioned RF10 (RPMI-1640 plus 10% FCS) containing 2.5 μg/ml puromycin. Transfected cells were then cultured and grown up.

EXAMPLE 12

Expression of transcripts containing RVWZ2 [SEQ ID NO: 4] and RWZ6 [SEQ ID NO: 8] in T-cells To demonstrate that transcripts containing the RWZ2 [SEQ ID NO: 4] and RWZ6 [SEQ ID NO: 8] motifs can be stably expressed in T-cells and to at least the same steady state level as RRE-containing transcripts the constructs described above were transfected into Jurkat and CEM T-cell lines and pools resistant to G418 sulfate (Geneticin®, Life Technologies) were selected.

Total RNA was prepared from the Jurkat pools (transfected cells and non-transfected control cells) using TRIzol™ reagent (Life Technologies) for an RNase protection assay. This RNA was probed using a uniformly labeled probe designed to detect both decoy-containing transcripts and endogerous CD2 mRNA. The latter feature was incorporated to confirm that equal amounts of RNA were analyzed.

The template to produce the riboprobe (ie. RNA probe) was pBluescript II KS(+) with the 315bp StuI-SacI fragment (ie. end of exon 5 and part of 3' untranslated region of the CD2 gene) inserted into SmaI-SacI digested plasmid. This template is called pKS/CD2frag. The riboprobe was made as a run off transcript using pKS/CD2frag linearized with SaiI and transcribing with T7 RNA polymerase. Transcription took place in a mixture comprising 1× transcription buffer (Promega); 10 mM DTT; 500 μM each of rATP, rCTP, rGTP; 2 μg template DNA; 40U RNAsin (Promega); (α-$^{32}$P)-UrP (2.5 mCi/ml, approx. 800 mCi/mmol); and 1U T7 RNA polymerase (Promega). This mixture was incubated at 37° C. for 60min. The probe was purified using PAGE before use.

The riboprobe was incubated with 10 μg cellular RNA in hybridisation mix (70% v/v formamide; 400 mM NaCl; 40 mM PIPES, pH 6.4; 1 mM EDTA) at 80° C. for 5 min, followed by incubation at 50° C. overnight. Unhybridized RNA was digested by incubation in 350 μl digestion mix (10 mM Tris, pH 7.5; 5 mM EDTA; 300 mM NaCl; 700 units/ml RNase T1) at 37 μC for 30 mins. 20 μl 10% SDS and 50 μg Protease K were added and the mixture was incubated for a further 10 mins at 37° C. The RNA was vortexed with an equal volume of phenol/chloroform/isoamylalcohol (25:24:1), centrifuged (5 minutes, 12000g), and the upper aqueous phase removed to a fresh tube. The RNA was ethanol precipitated, washed in 75% ethanol, then resuspended in 4 μl DEPC-treated water and 4 μl formamides dyes.

The samples we,re heated to 90° C. for 5 mins before running on a prewarmed 8M urea, 6% polyacrylamide gel. The gel was fixed and dried, and the bands were visualized by autoradiography.

Figure 17:
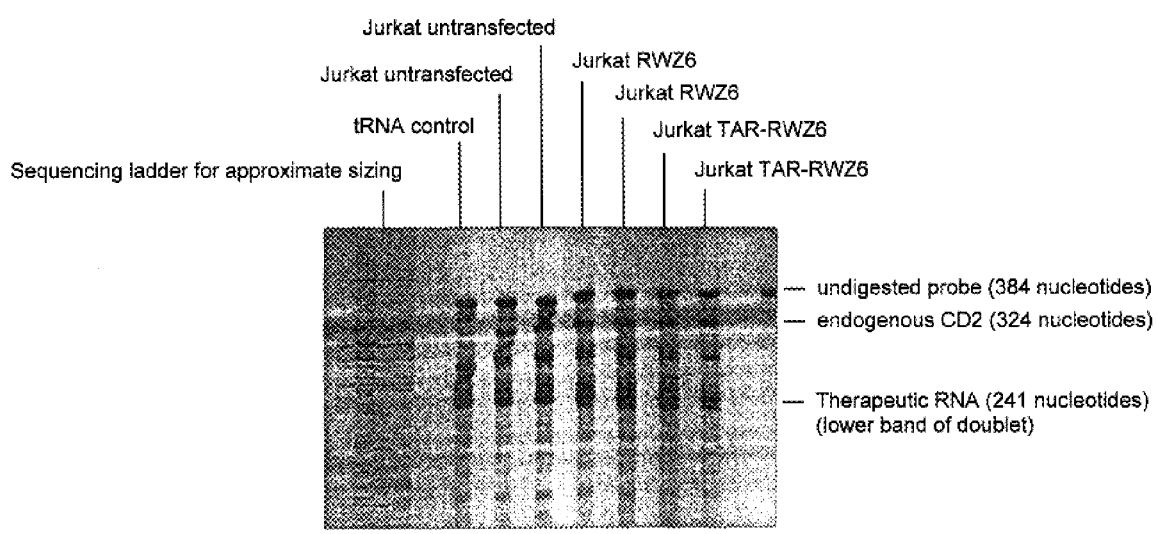
FIG. 17 shows the results of an RNase protection assay, demonstrating the stable expression on constructs according to the invention.

Constructs were able to direct the synthesis of a stable mRNA species, as shown, for example, in FIG. 17. No significant difference in expression level was apparent based on the relative intensity of the protected fragment.

EXAMPLE 13

Transactivation of HIV'-2 LTR driven decoy constructs

Tat-mediated transactivation of decoy-encoding plasmids containing the HIV-2 LTR is confirmed by transient cotransfection into Cos cells with a Tat expression vector and semi-quantitative RT-PCR. To take into account variability in transfection efficiency, a luciferase expressing plasmid is included and RNA levels also determined by RT-PCR. Primers are designed to flank an intron so that the expressed product may be differentiated from the input DNA product.

Cells are transfected at 50% confluence in 10cm petri dishes using lipofectin (Life Technologies). DNA mixes (8 ug total) are prepared with/without 0.4 ug of pCMVtat construct. These mixes contain 2 ug of an RSVluciferase reporter construct, 4 ug of the HIV-2 LTR-driven decoy construct and 2 ug (untransactivated sample) or 1.6 ug (transactivated samples) of pBR322 carrier DNA in a final volume of 100 ul. 300 ul of DMEM medium is added to each DNA mix. 40 ul of lipofectin (lipofectin:DNA ratio of 5: 1) is added to 360 μl DMEM (Dulbecco's modified eagle's medium) and incubated at room temperature for 35–40 minutes. The DNA mix is added to the diluted lipofectin and incubated at room temperature for 10–15 minutes.

Prior to transfection, growth medium is removed and residual serum-containing medium by washing with phosphate buffered saline (PBS). 3.2 ml of DMEM is then added to each plate followed by the addition of the lipofectin/DNA mix. The cells are then incubated in a 5% CO2/air incubator at 37° C. for 5 hours. Lipofectin/DNA-containing medium is removed from the cells and replaced with serum-containing DMEM medium. The cells are then incubated for a further 48 hours in a 5% CO$^2$/air incubator at 37° C. The medium is removed from the cells and the cells are lysed by adding ml of Trizol reagent (Life Technologies) to each petri dish with passing of the cell lysate several times through a pipette. The lysates are either processed immediately to make RNA or stored at −80° C. RNA is isolated according to the manufacturers instructions and resuspended in a final volume of 50 μl of DEPC-treated $H_2O$.

Residual transfected DNA is removed prior to reverse transcription with RNase-free DNase I (Boehringer Mannheim). 20 ul of RNA is incubated with 10 units of RNase-free DNase at 37° C. for 30 minutes in 100 ul of 1× DNase I buffer. The reaction is stopped by the addition of DNase stop solution. DNA-free RNA is purified by successive extractions with phenol/chloroform/isoamylalcohol and chloroform and by ethanol precipitation and resuspended in 20 ul of DEPC-treated $H_2O$.

Reverse transcription is performed as follows: 1 ul of Oligo dT is added to 5 ul of DNA-free RNA and the volume made up to 12 ul with DEPC-treated $H_2$0. Oligo-dT primers are annealed to the RNA template by incubating at 9'(C for 4 minutes and 70° C. for 6 minutes, followed by snap-cooling on ice. 4 ul of 5 ul first strand buffer, 2 ul of 0.1M DTT and 1 ul of 10 mM dNTPs mixture are then added and the reaction incubated at 42° C. for 2 minutes. 1 ul of Superscript II reverse transcriptase (Life Technologies) is added and the reaction incubated at 42° C. for 50 minutes, followed by 70° C. for 15 minutes and snap-cooling on ice.

PCR is performed as follows: 1 ul of the cDNA is amplified in a 25 ul reaction in 1× reaction containing primers, dNTPs mixture and $MgCl_2$ are used at 1 μM, 200uM and 2 mM final concentration respectively buffer with "Thermoprime plus" enzyme at 20 units/ml. The following cycle conditions are used: initial denaturation 95° C. for 4 minutes followed by 35 cycles of: 57° C. for 1 minute, 72° C. for 1. minute 30 seconds, 95° C. for 1 minute. A final cycle is performed with a 4 minute extension reaction. PCR products (5 ul) are analyzed by electrophoresis on an agarose gel.

EXAMPLE 14

Inhibition of HIV replication

The relative efficacy of the transcripts containing Rev decoys of the present invention in inhibiting HIV replication was compared using an HIV spread assay. In this assay, transfected Jurkat T-cell pools expressing the different inhibitory transcripts were infected at a low multiplicity of infection (moi) and the efficiency of spread of virus through the majority uninfected cells was monitored over a 3 week period and compared to control cells. Two control cell-lines were used, one being non-transfected and the other being transfected with an expression vector lacking decoy inserts. HIV-1 strain IIIB was used for this assay since, although a lab adapted strain, it is a widely available and well characterized virus for which a lot of comparative data is available in the literature.

The titer of the HIV-IIIB used in these tests was determined as follows. Serial virus dilutions were applied to Jurkat T-cells in 24 well plates. 7 days after infection, cell free supernatant was harvested from each well and virus levels were determined by assaying levels of two HIV proteins: p24 and reverse transcriptase (RT). p24 levels were determined with a sandwich ELISA (DuPont NEN, HIV p24 core profile ELISA, catalogue no. NEK-060B) and RT levels by a non-radioactive enzymic assay (RT assay from Amersham International, PolyR(A) RT SPA enzyme assay, catalogue no. NK-9020). Both kits were used according to the manufacturers' instructions. The $TCID_{50}$ was defined as the dilution which resulted in productive virus production in 50% of wells.

Figure 18A:
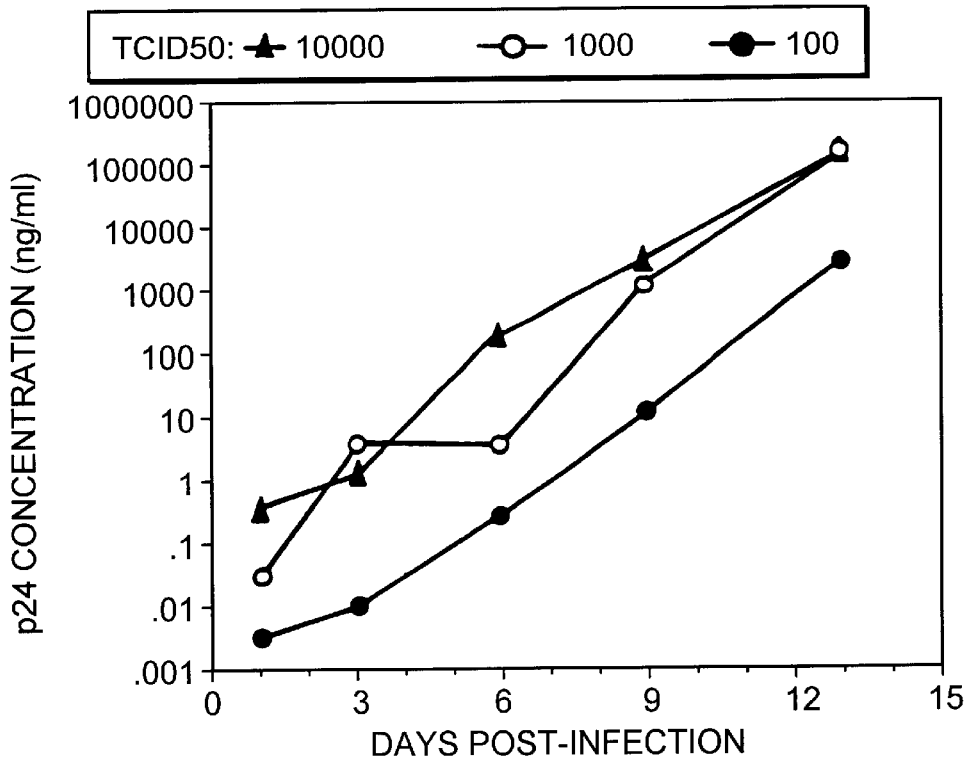
FIG. 18 shows the dependence of viral spread on multiplicity of infection.
Figure 18B:
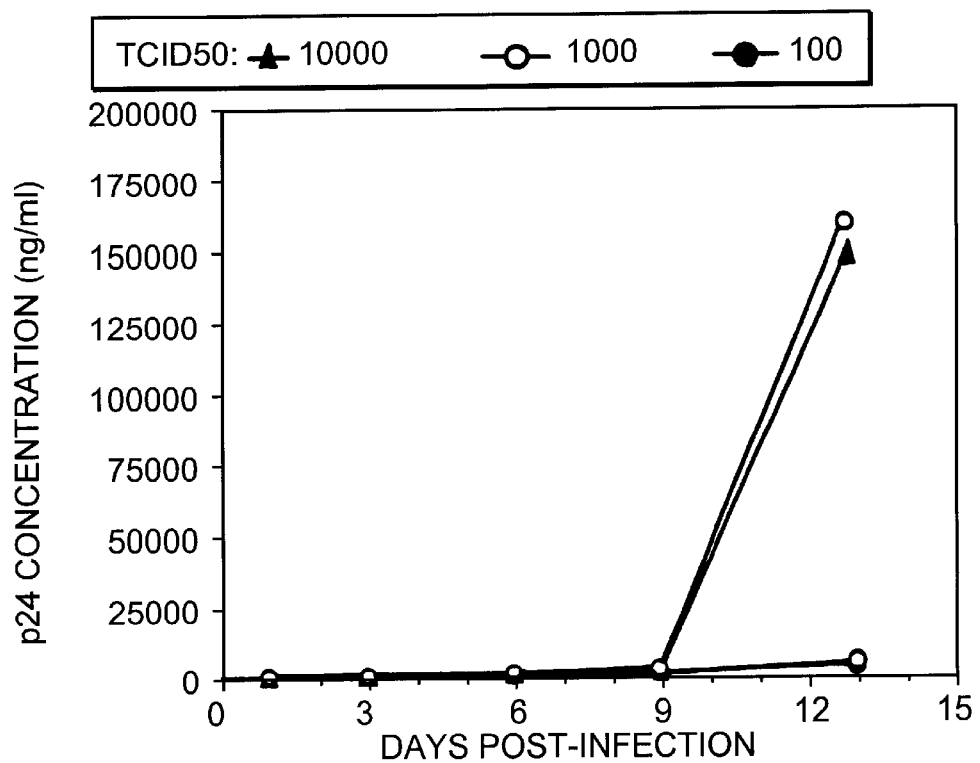

To determine a moi for HIV-IIIB which results in progressive virus spread throughout Jurkat cultures, cells were infected with 100, 1000 and 10,000×$TCID_{50}$ and processed in the following way. After a 16 hour adsorption step, infected cells were collected by centrifugation and resuspended in fresh growth medium to remove non-adsorbed virus and virus debris. Virus release was then monitored over successive 3 day periods by resuspending the infected cell cultures at the end of each 3 day period in fresh medium and assaying levels of p24 and RT in the cell free supernatants taken. The dependence of viral spread on the initial moi used is shown in FIG. 18. Based on this data, an moi of 100×$TCID_{50}$ was selected to challenge Jurkat and CEM pools expressing candidate decoys in the above HIV spread assay.

The spread assail results indicate that molecules according to the present invention are able to inhibit HIV replication. Accumulation of virus in the culture medium is significantly delayed in comparison to control cells. Maintenance of CD4 expression is prolonged. Staining for gp120 shows that the time taken to achieve 100% infection of the cultures is significantly extended.

EXAMPLE 15

Efficacy of RNA Molecules of the Invention in Inhibiting HIV replication in transfected cells.

Jurkat T cells were transfected with constructs comprising the pHIV-2LTR.VA.puro vector containing a TAR [SEQ ID NO: 18] element and, respectively, the full-length RRE[SEQ ID NO: 1], RWZ2 [SEQ ID NO: 4] and RWZ6 [SEQ ID NO: 4] and clonal puromycin resistant lines isolated by limiting dilution cloning.

Clonal cell lines were then subjected to HIV challenge at two moi's (1000 and 100 TCID50) using the MN virus strain as follows. $10^5$ cells of Jurkat clones (0.5 ml/well, 3 wells for each clone) were plated in a 24 well plate. 0.5 ml of MN (2 dilutions) (0.5 ml medium to control well) virus was added to each well, and incubated 3 hr. The plate was spun down at 400 g, 5 min, then 1.5 ml of S/N was discarded. The wells were washed twice using 1.5 ml fresh medium. Cells were then resuspended in 2 ml medium (RPMI 1640+ FCS +P/S+0.5 puromycin) and incubated for 1 hr. 200 ul from the top of each well was taken as a base line sample for ELISA and 1.2 ml medium was added to each well, and incubated 37° C. Each day, the wells were examined for syncytia. After 7 days, samples were taken for a p24 assay. Syncytia were scored daily (−means 0; +means 10%; ++means 50%; and +++means 90–100%).

Inhibition of syncytia formation and inhibition of virus release (via p24 ELISA) were determined. Non-infected and infected parental Jurkat cells were used as negative and positive controls, respectively.

9 Tar-RWZ2 clones, 5 TAR-RWZ6 clones and 3 TAR-RRE clones were analyzed. The following results were obtained for cells infected with an moi of 100 TCID50 (% inhibition of HIV replication based on p24 ELISA). Plates were coated with 100 ul D7320 (diluted to 1 mg/ml) to 9.9 ml coating buffer (100 mM NaHCO3 pH 8.5), and 100 ul added to each well. After remaining at room temperature overnight, the plates were washed with 1× TBS for 3×200 ul; 200 ul blocking buffer (0.4 g milk powder in 20 ml 1× TBS) was added to each well for 30 min, and wells were washed with 1× TBS using 3×200 ul. 100 ul supernatant (previously treated with 0.1%–0.2% empigen and heat-inactivated for 30 min. At 56° C.) was placed into each well. Plates were left overnight at room temperature. Plates were washed 6×200 ul TBS with 1× TBS, and diluted biotinylated antibody to p24 (100 ul of a 100 ul in 10 ml TMT/SS solution) was added and left at room temperature for 2 hr. Anti-p24 antibody (D7320) was obtained from Aalto Bioreagents Ltd., Dublin, Ireland. (TMT/SS contains 1× TBS with 2% milk, 20% lamb serum, 0.5% Tween 20). Plates were washed with 1× TBS (6×200 ul). 100 ul (20 µl in 10 ml TMT/SS) streptavidin-AP was added and plates were left at room temperature for 1 hr. Plates were then washed with 1× TBS (6×200 ul). 100 ul (2×5 mg tablets in 10 ml reaction buffer) pNpp solution was added to each well. The plate was then placed in the dark until a control plate OD of 100 ng/ml >1.000 was reached. OD is read at 405 nm.

The results demonstrated that the TAR-RWZ2 constructs showed varying results (<50%, <50%, 72%, <50%, 60%, 0%, 67%, 66%, 0%), the TAR-RWZ6 constructs showed significant inhibition (85%, 99%, 95%, <50%, 86%), and both RWZ constructs showed better inhibition than TAR-RRE (<50%, <50%, <50%), which consistently showed less than 50% inhibition. The data are thus consistent with the conclusion that both RWZ2 [SEQ ID NO: 4] and RWZ6 [SEQ ID NO: 8] RNA molecules of the invention possess anti-HIV activity which is better than that of the native RRE [SEQ ID NO: 1] competitor, and that RWZ6 [SEQ ID NO: 8] is better inhibitor of the two RNA molecules of the invention which were tested.

EXAMPLE 16

Targeted delivery of decoys to T-cell lines

Certain embodiments of the present invention require that expression vectors encoding decoys are specifically introduced into T-cells using targeted delivery systems relying, for instance, on molecules with binding-affinity for T-cells. A luciferase reporter gene is efficiently and selectively delivered to Jurkat T-cells using an anti-CD7 monoclonal antibody to achieve selective uptake of the gene complex by T-cells. The use of appropriate ligands will allow equivalent targeting to other cells of relevance to HIV disease, such as monocyte and macrophages (anti CD14), dendritic cells (mannose), and haematopoietic stem cells (anti CD34).

It will be understood that the invention is described above by way of example only and modifications may be made within the scope and spirit of the invention.

REVDECOY TABLE 1A

Jurkat infection inhibition assay

| # | Clone/Construct | TCIDMN | Syncytium formulation in Jurkat Cells | | | | | p24 Antigen | | | |
|---|---|---|---|---|---|---|---|---|---|---|---|
| | | | d3 | d4 | d5 | d6 | d7 | d0 | d7 | dp24% | Inhib % |
| | Jurkat Control | None | − | − | − | − | − | 0.069 | 0.059 | 0.0 | 0.0 |
| | | None | − | − | − | − | − | 0.075 | 0.060 | 0.0 | 0.0 |
| | Jurkat Control | 1000 | | +++ | +++ | +++ | +++ | 0.153 | 1.406 | 100.0 | 0.0 |
| | | 100 | | ++ | +++ | +++ | ++ | 0.075 | 1.340 | 100.0 | 0.0 |
| 51 | C7 TAR RWZ6 | 1000 | | ++ | ++ | ++ | ++ | 0.167 | 0.506 | 25.5 | 74.5 |
| | | 100 | | + | + | + | + | 0.070 | 0.085 | 1.2 | 93.8 |
| 52 | C8 TAR RWZ6 | 1000 | | − | − | + | ++ | 0.129 | 0.30 | 58 | <50 |
| | | 100 | | ++ | ++ | −+ | ++ | 0.070 | 0.138 | 5.4 | 94.6 |
| 53 | C9 TAR RWZ6 | 1000 | | + | + | + | ++ | 0.135 | 1.471 | 100 | <50 |
| | | 100 | | + | + | + | ++ | 0.071 | 0.949 | 69.4 | <50 |
| 54 | C11 TAR RWZ6 | 1000 | | + | + | + | + | 0.138 | 1.012 | 65.7 | <50 |
| | | 100 | | + | + | + | + | 0.072 | 1.251 | 14.1 | 85.9 |
| 55 | C11 TAR RRE | 1000 | | ++ | +++ | +++ | ++ | 0.146 | 2.168 | 152 | — |
| | | 100 | | | | | | 0.079 | 1.567 | 117.6 | — |
| 56 | C1 TAR RRE | 1000 | | +++ | +++ | +++ | ++ | 0.140 | 1.219 | 81.1 | <50 |
| | | 100 | | ++ | ++ | +++ | ++ | 0.071 | 1.219 | 90.0 | <50 |
| 57 | C10 TAR RRE | 1000 | | + | + | + | ++ | 0.125 | 0.929 | 60.4 | <50 |
| | | 100 | | − | − | − | + | 0.069 | 0.301 | 13.3 | 81.7 |
| 58 | C4 TAR RRE | 1000 | | +++ | +++ | +++ | +++ | 0.141 | 1.296 | 86.8 | <50 |
| | | 100 | | + | ++ | + | ++ | 0.072 | 0.99 | 78.3 | <50 |

REVDECOY TABLE 1B

Jurkat infection inhibition assay

| # | | | Syncytium formation in Jurkat cells | | | | | p24 Antigen | | | |
|---|---|---|---|---|---|---|---|---|---|---|---|
| | | | d3 | d4 | d5 | d6 | d7 | d0 | d7 | p24% | Inhib % |
| | Jurkat Control | None | − | − | − | − | − | 0.068 | 0.059 | 0.0 | 0.0 |
| | | None | − | − | − | − | − | 0.067 | 0.060 | 0.0 | 0.0 |
| | Jurkat Control | 1000 | | ++ | +++ | +++ | ++ | 0.116 | 1.703 | 100 | 0.0 |
| | | 100 | | + | + | +++ | +++ | 0.071 | 1.351 | 100 | 0.0 |
| 41 | C1 TAR RWZ2 | 1000 | | + | ++ | ++ | ++ | 0.116 | 1.213 | 69 | <50 |
| | | 100 | | − | − | + | ++ | 0.062 | 0.456 | 30.8 | 69.2 |
| 42 | C4 TAR RWZ2 | 1000 | | +++ | +++ | +++ | +++ | 0.085 | 1.503 | 89.0 | <50 |
| | | 100 | | + | ++ | +++ | +++ | 0.063 | 1.179 | 87.0 | <50 |
| 43 | C7 TAR RWZ2 | 1000 | | +++ | +++ | +++ | +++ | 0.087 | 1.122 | 65.2 | <50 |
| | | 100 | | + | ++ | ++ | ++ | 0.067 | 0.435 | 28.8 | 71.8 |
| 44 | C9 TAR RWZ2 | 1000 | | +++ | +++ | +++ | ++ | 0.090 | 1.404 | 82.7 | <50 |
| | | 100 | | ++ | ++ | +++ | ++ | 0.067 | 0.904 | 65.4 | <50 |
| 45 | C11 TAR RWZ2 | 1000 | | +++ | +++ | +++ | +++ | 0.092 | 1.499 | 88.6 | <50 |
| | | 100 | | + | ++ | ++ | ++ | 0.072 | 0.587 | 40.2 | 60 |
| 46 | C12 TAR RWZ2 | 1000 | | +++ | +++ | +++ | ++ | 0.079 | 1.664 | 99.8 | <50 |
| | | 100 | | ++ | ++ | ++ | +++ | 0.063 | 1.432 | 106.9 | — |
| 47 | C6 TAR RWZ2 | 1000 | | ++ | ++ | ++ | ++ | 0.091 | 1.225 | 71.4 | <50 |
| | | 100 | | − | − | − | + | 0.065 | 0.616 | 43.0 | 67 |
| 48 | C8 TAR RWZ2 | 1000 | | ++ | +++ | +++ | +++ | 0.088 | 0.999 | 57.4 | <50 |
| | | 100 | | − | ++ | +++ | +++ | 0.068 | 0.634 | 44.2 | 66 |
| 49 | C1 TAR RWZ2 | 1000 | | ++ | +++ | +++ | ++ | 0.105 | 1.070 | 60.8 | <50 |
| | | 100 | | − | ++ | +++ | ++ | 0.068 | 0.257 | 14.8 | 85 |
| 50 | C6 TAR RWZ2 | 1000 | | −+ | +++ | +++ | ++ | 0.104 | 1.587 | 93.4 | <50 |
| | | 100 | | ++ | ++ | ++ | ++ | 0.075 | 1.360 | 100 | 0.0 |

Inhib = Inhibition (%)

References

Aboul-ela, F., Karn, J. & Varani, G. (1995). The structure of the human immunodeficiency virus type 1 TAR RNA reveals principles of RNA recognition by Tat protein. *J. MoL BioL*, 253, 313–332.

Adra et al. Gene 60, 65–74.

Bartel, D. P., Zapp, M. L., Green, M. R. & Szostak, J. W. (1991). HIV-1 Rev regulation involves recognition of non-Watson-Crick base pairs in viral RNA. *Cell*, 67, 529–536.

Battiste, J. L., Tan, R., Frankel, A. D. & Williamson, J. R. (1994). Binding of an HIV Rev peptide to Rev responsive element RNA induces formation of purine-purine base pairs. *Biochemistry*, 33, 2741–2747.

Bogerd, H. P., Fridell, R. A., Madore, S. & Cullen, B. R. (1995). Identification of a novel cellular co-factor for the Rev/Rex class of retroviral regulatory proteins. *Cell*, 82, 485–494.

Brady H J, Miles C G. Pennington D J, Dzierzak E A. (1994). Specific ablation of human immunodeficiency virus Tat-expressing cells by conditionally toxic retroviruses. *Proc Natl Acad Sci USA* 91, 365–369.

Cochrane, A. W., Chen, C.-H. & Rosen, C. A. (1990). Specific interaction of the human immunodeficiency virus Rev protein with a structured region in the env mRNA. *Proc. Natl. Acad Sci. USA*, 87, 1198–1202.

Cook, K. S., Fisk, G. J., Hauber, J., Usman, N., Daly, T. J. & Rusche, J. R. (1991). Characterization of HIV-1 Rev protein: binding and stoichiometry and minimal RNA substrate. *Nucl. Acid Res.*, 19, 1577–1583.

Cooper MJ & Miron S. (1993). Efficient episomal expression vector for human transitional carcinoma cells. *Human Gene Therapy* 4, 557–566.

Crisell P, Thompson S, James W (1993) Inhibition of HIV-1 replication by ribozymes that show poor activity in vitro. *Nucl. Acids Res.*, 21, 5251–5255.

Daly, T. J., Cook, K. S., Gary, G. S., Maione, T. E. & Rusche, J. R. (1989). Specific binding of HIV-1 recombinant Rev protein to the Rev-responsive element in vitro. Nature, 342, 816–819.

Dayton, E. T., Konings, D. A. M., Powell, D. M., Shapiro, B. A., Butini, L., Maizel, J. V. & Dayton, A. I. (1992). Extensive sequence-specific information throughout the CARIRRE, the target sequence of the human immunodeficiency virus type 1 rev protein. *J. Virol.*, 66, 1139–1151.

Dayton, E. T., Powell, D. M. & Dayton, A. I. (1989). Functional analysis of CAR, the target sequence for the Rev protein of HIV-1. Science, 246, 1625–1629.

Emerman, M., Vazea;ax, R. & Peden, K. (1989). The rev gene product of the human immunodeficiency virus affects envelope specific RNA localization. *Cell*, 57, 1155–1165.

Emerman M, Guyader CM, Montagnier L, Baltimore D, Muesing Mass. (1987). The specificity of the human immunodeficiency birus type 2 transactivator is different from that of human immunodeficiency virus type 1. *EMBO J* 6, 3755–3760.

Fischer, U., Huber, J., Boelens, W. C., Mattaj, I. W. & Luhnmann, R. (1995). The HIV-1 Rev activation domain is a nuclear export signal that accesses an export pathway used by specific cellular RNAs. *Cell*, 82, 475–483.

Fischer, U., Meyer, S., Teufel, M., Heckel, C., Luhrnann, R. & Rautmann, G. (1994). Evidence that HIV-1 Rev directly promotes the nuclear export of unspliced RNA. *EMBO J.*, 13, 4105–4112.

Giver, L., Bartel, D., Zapp, M., Pawul, A., Green, M. & Ellington, A. D. (1993). Selective optimization of the rev-binding element of HIV-1. *Nucleic Acids Research*, 21, 5509–5516.

Hall, L. & Emery, D. C. (1991). A rapid and efficient method for site-directed mutagenesis by PCR using biotinylated universal primers and streptavidin-coated magnetic beads. *Protein Eng.*, 4,601.

Harada K., Martin S. S., Frankel A. D. (1996). Selection of RNA-binding peptides in vivo. *Nature*, 380, 175–179.

Heaphy, S., Dingwall, C., Ernberg, I., Gait, M. J., Green, S. M., Karn, J., Lowe, A. D., Singh, M. & Skinner, M. A. (1990)). HIV-1 regulator of virion expression (Rev) protein binds to an RNA stem-loop structure located within the Rev-response element region. *Cell*, 60, 685–693.

Heaphy, S., Finch, J. T., Gait, M. J., Karn, J. & Singh, M. (1991). Human immunodeficiency virus type1 regulator of virion expression, Rev, forms nucleoprotein filaments after binding to a purine-rich "bubble" located within the Rev-responsive region of viral RNA. *Proc. Natl. Acad. Sci. USA*, 88, 7366–7370.

Holland, S. M., Chavez, M., Gerstberger, S. & Venkatesan, S. (1992). A specific sequence with a bulged guanosine residue(s) in a stem-bulge-stem structure rev-responsive element RNA is required for trans-activation by human immunodeficiency virus type 1 rev. *J. Virol.*, 66, 3699–3706.

Huang, X., Hope, T. J., Bond, B. L., McDonald, D., Grahl, K. & Parslow, T. G. (1991). Minimal Rev-response element for type 1 human immunodeficiency virus. *J. Virol.*, 65, 2131–2134.

Iwai, S., Pritchard, C., Mann, D. A., Karn, J. & Gait, M. J. (1992). Recognition of the high affinity binding site in rev-response element RNA by the human immunodeficiency virus type-1 rev protein. *Nucl. Acids Res.*, 20, 6465–6472.

Jaeger, J. A., Turner, D. H. & Zuker, M. (1989a). Inproved predictions of secondary structures for RNA. *Proc. Natl. Acad. Sci. USA*, 86, 7706–7710.

Jaeger, J. A., Turner, D. H. & Zuker, M. (1989b). Predicting optimal and suboptimal secondary structures for RNA. *Methods Enzymol.*, 183, 281–306.

Jensen, K. B., Green, L., MacDougal-Waugh, S. & Tuerk, C. (1994). Characterization of an in vitro-selected RNA ligand to the HIV-1 Rev protein. *J. Mol. Biol.*, 234, 235–247.

Jensen, T. H., LefferE,s, H. & Kjems, J. (1995). Intermolecular binding sites of human immunodeficiency virus type 1 Rev protein determined by protein footprinting. *J. Biol. Chem.*, 270, 13777–13784.

Jensen K. B., Atkinson B. L., Willis M. C., Koch T. H., Gold L. (1995) Using in vitro selection to direct the covalent attachment of human immunodeficiency virus type 1 Rev protein to high-affinity RNA ligands. *Proc. Natl. Acad. Sci. USA*, 92, 12220–12224.

Kjeems, J., Brown, M., Chang, D. D. & Sharp, P. A. (1991). Structural analysis of the interaction between the human immunodeficiency virus Rev protein and the Rev response element. *Proc. Natl. Acad. Sci. USA*, 88, 683–687.

Kjems, J., Calnan, B. J., Frankel, A. D. & Sharp, P. A. (1 992). Specific binding of a basic peptide from HIV-1 Rev. *EMBO J.*, 11, 1119–1129.

Krupp, G. (1988). RNA synthesis: strategies for the use of bacteriophage RNA polymerases. *Gene*, 73, 73–89.

Malim, M. H., Bohnlein, S., Hauber, J. & Cullen, B. R. (1989a). Functional dissection of the HIV-1 Rev transactivator: Derivation of a trans-dominant repressor of Rev function. *Cell*, 58, 205–214.

Malim, M. H. & Cullen, B. R. (1991). HIV-1 structural gene expression requires the binding of multiple Rev monomers to the viral RRE: Implications for HIV-1 latency. *Cell*, 65, 241–248.

Malim, M. H. & Cullen, B. R. (1993). Rev and the fate of pre-mRNA in the nucleus: Implications for the regulation of RNA processing in eukaryotes. *Mol. Cell Biol.*, 13, 6180–6189.

Malim, M. H., Hauber, J., Le, S.-Y., Maizel, J. V. & Cullen, B. R. (1989b). The HIV-1 Rev trans-activator acts through a structured target sequence to activate nuclear export of unspliced viral mRNA. *Nature*, 338, 254–257.

Malim, M. H., McCarn, D. F., Tiley, L. S. & Cullen, B. R. (1991). Mutational definition of the human immunodeficiency virus type 1 Rev activation domain. *J. Virol.*, 65, 4248–4254.

Malim, M. H., Tiley, L,. S., McCarn, D. F., Rusche, J. R., Hauber, J. & Cullen, B. R. (1990). HIV-1 structural gene expression requires binding of the Rev trans-activator to its RNA target sequence. *Cell*, 60, 675–683.

Mann, D. A., Mikaeliani, I., Zemmel, R. W., Green, S. M., Lowe, A. D., Kimura, T., Singh, M., Butler, P. J. G., Gait, M. J. & Karn, J. (1994). A molecular rheostat: Co-operative Rev binding to Stem I of the Rev-response element modulates human immunodeficiency virus type-1 late gene expression. *J. Mol. Biol.*, 241, 193–207.

Martin, C. T. & Coleman, J. E. (1987). Kinetic analysis of T7 RNA polymerase-promoter interactions with small synthetic promoters. *Biochemistry*, 26, 2690–2696.

McGhee, J. D. & von Hippel, P. H. (1974). Theoretical aspects of DNA-protein interactions: Cooperative and non-cooperative binding of large ligands to a one-dimensional homogeneous lattice. *J. Mol. Biol.*, 8i6, 469–489.

Meyer, B. E. & Malim, M. H. (1994). The HIV-1 rev trans-activator shuttles between the nucleus and the cytoplasm. *Genes Develop.*, 8, 1538–1547.

Morgenstern & Land. *Nucl. Acid. Res.* 12, 3587–3595.

Olsen, H. S., Nelbrock, P., Cohrane, A. W. & Rosen, C. A. (1990). Secondary structure is the major determinant for interaction of HIV rev protein with RNA. *Science*, 247, 845–848.

Peterson, R. D., Bartel, D. P., Szostak, J. W., Horvath, S. J. & Feigon, J. (1994a). 1H NMR studies of the high-affinity rev binding site of the rev response element of HIV-1 mRNA: Base pairing in the core binding element. *Biochemistry*, 33, 5357–5366.

Peterson, P. D., Bartel, .D. P., Szostak, J. W., Horvath, S. J. & Feigon, J. (1994b). 1H NMR studies of the high affinity Rev binding site of the Rev-response element of HIV-1 mRNA: Base pairing in the core binding element. *Biochemistry*, 33, 5357–5366.

Pfarr et al. *DNA* 5, 115–122.

Piirsoo, M., Ustav, E., Mandel, T., Stenlund, A. & Ustav, M. (1995). Cis and trans requirements for stable episomal maintenance of the BPV-1 replicator. *EMBO J*, 14, 101–110.

Powell, D. M., Zhang M. J., Konings A. M., Wingfield P. T., Stahl S. J., Dayton E. T., Dayton A. I. (1995) Sequence specificity in the higher-order interaction of the Rev protein of HIV-1 with its target sequence, the RIZE. *J. Acq. Imm. Def. Syndr. & Hum. Retrov.*, 10, 317–323.

Pritchard, C. E., Grasby, J. A., Hamy, F., Zachareck, A. M., Singh, M., Karn, J. & Gait, M. J. (1994). Methylphosphonate mapping of phosphate contacts critical for RNA recognition by the human immunodeficiency virus tat and rev proteins. *Nucl. Acids Res.*, 22, 2592–2600.

Puglisi, J. D., Tan, R., Calnan, B. J., Frankel, A. D. & Williamson, J. R. (1992). Conformation of the TAR RNA-arginine complex by NMR spectroscopy. *Science*, 257, 76–80.

Ratner et al. (1985) Complete nucleotide sequence of the AIDS virus, HTLV-III. *Nature* 313,277–284.

Rosen, C. A., Terwilliger, E., Dayton, A. I., Sodrowski, J. G. & Haseltine, W. A. (1988). Intragenic cis-acting art-responsive sequences of the human immunodeficiency virus. *Proc. Natl. Acad. Sci. USA*, 85,2071–2075.

Stutz, F., Neville, M. &; Rosbach, M. (1995). Identification of a novel nuclear pore-associated protein as a functional target of the HIV-1 Rev protein in yeast. *Cell*, 82, 495–506.

Tabor, S. & Richardson, C. C. (1985). A bacteriophage T7 RNA polymerase/promoter system for controlled exclusive expression of specific genes. *Proc. Nat. Acad. Sci., USA*, 82, 1074–1078.

Tiley, L. S., Malim, M. H., Tewary, H. K., Stockley, P. G. & Cullen, B. R. (1992). Identification of a high-affinity RNA-binding site for the human immunodeficiency virus type 1 rev protein. *Proc. Natl. Acad. Sci. USA*, 89, 758–762.

Weeks, K. M. & Crothers, D. M. (1991). RNA recognition by tat-derived peptides: Interaction in the major groove? *Cell*, 66, 577–588.

Weiss A, Wiskocil R L, Stobo J D. (1984). The role of T3 surface molecules in the activation of human T cells. *J. Immunol.* 133, 123–128.

Wen, W., Meinkoth, J. L., Tsien, R. Y. & Taylor, S. S. (1995). Identification of a signal for rapid export of proteins from the nucleus. *Cell*, 82, 463–473.

Wolff, B., Cohen, G., Hauber, J., Meshcheryakova, D. & Rabeck, C. (1995). Nucleocytoplasmic transport of the rev protein of human immunodeficiency virus type 2 is dependent on the activation domain of the protein. *Exper. Cell Res.*, 217, 31–41.

Yates J L, Warren N, Sugden B. (1985). Stable replication of plasmids derived from Epstein-Barr virus in various mammalian cells. *Nature* 313, 812–815.

Zapp, M. L. & Green, M. R. (1989). Sequence-specific binding by the HIV-1 rev protein. *Nature*, 342, 714–716.

Zapp, M. L., Hope, T. J., Parslow, T. G. & Green, M. R. (1991). Oligomerization and RNA binding domains of the type 1 human immunodeficiency virus rev protein: A dual function for an arginine-rich binding motif. *Proc. Nat. Acad. Sci. USA*, 88, 7734–7738.

Zapp, M. L., Stem, S. & Green, M. R. (1993). Small molecules that selectively block RNA binding of HIV-1 rev protein inhibit rev function and viral production. *Cell*, 74, 969–978.

Zhumabekov T, Carbella P, Tolaini M, Kioussis D. (1995). Improved version of a human CD2 minigene based vector for T cell-specific expression in transgenic mice. *J. Immunol. Methods*, 185, 133–140.

Zuker, M. (1989). On finding all suboptimal foldings of an RNA molecule. *Science*, 244, 48–52.

What is claimed is:

1. An isolated nucleic acid comprising two operatively linked binding sites for HIV Rev protein, said sites comprising a nucleation motif and an oligomerization motif, wherein said nucleic acid binds Rev protein monomers with a higher degree of co-operativity than the wild-type RRE.

2. The nucleic acid of claim 1, comprising RNA.

3. The nucleic acid of claim 1, wherein said nucleation motif comprises the following generic structural formula:

—EG RN AYP—3'

—FCR'(N')$_n$GR"Q—5' where n=0 or 1; Y & R" are, respectively, a pyrimidine and purine; E & F are nucleotides which can form a base pair; P & Q are nucleotides which can form a base pair; R and R' are purines; and N and N' are any nucleotide.

4. The nucleic acid of claim 3, wherein n=0, E is C, F is G, N is U, R is G, R' is G, Y is C, R" is G.

5. The nucleic acid of claim 1, wherein said oligomerization motif comprises a region of duplex disruption in a double-stranded nucleic acid.

6. The nucleic acid of claim 5, wherein said region of duplex disruption comprises a UC dinucleotide bulge functionally linked to said nucleation motif followed by a potential non-Watson-Crick G•U base pair.

7. The nucleic acid of claim 1, comprising a single nucleation motif.

8. The nucleic acid of claim 7, comprising two oligomerization motifs.

9. The nucleic acid of claim 1, wherein said oligomerization motif is upstream of said nucleation motif.

10. The nucleic acid of claim 1, wherein said oligomerization motif is downstream of said nucleation motif.

11. The nucleic acid of claim 1, further comprising a spacer sequence between the disruptions in adjacent Rev-binding motifs of less than about 11 base pairs.

12. The nucleic acid of claim 11, said spacer being less than 8 base pairs.

13. The nucleic acid of claim 12, said spacer being less than 5 base pairs.

14. The nucleic acid of claim 1, comprising two nucleation motifs.

15. The nucleic acid of claim 1, further comprising one of the HIV TAR sequence, a ribozyme that cleaves within the Tat open reading frame, and a sequence that hybridizes to Tat mRNA.

16. A vector which encodes an isolated nucleic acid according to claim 1.

17. A host cell transfected with the vector of claim 16.

* * * * *

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
       (A) LENGTH: 352 bases
       (B) TYPE: nucleic acid
       (C) STRANDEDNESS: single
       (D) TOPOLOGY: unknown (ii) MOLECULE TYPE: mRNA (xi) SEQUENCE DESCRIPTION: SEQ ID NO: 1:

```
UAGCACCCAC CAAGGCAAAG AGAAGAGUGG UGCAGAGAGA AAAAAGAGCA G UGGGAAUAG      60

GAGCUUUGUU CCUUGGGUUC UUGGGAGCAG CAGGAAGCAC UAUGGGCGCA G CGUCAAUGA     120

CGCUGACGGU ACAGGCCAGA CAAUUAUUGU CUGAUAUAGU GCAGCAGCAG A ACAAUUUGC     180

UGAGGGCUAU UGAGGCGCAA CAGCAUCUGU UGCAACUCAC AGUCUGGGGC A UCAAACAGC     240

UCCAGGCAAG AAAUCCUGGC UGUGGAAAGA UACCUAAAGG AUCAACAGCU C CUGGGGAUU     300

UGGGGUUGCU CUGGAAAACU CAUUUGCACC ACUGCUGUGC CUUGGAAUGC U A             352
```

(2) INFORMATION FOR SEQ ID NO: 2:

(i) SEQUENCE CHARACTERISTICS:
       (A) LENGTH: 238 bases
       (B) TYPE: nucleic acid
       (C) STRANDEDNESS: single
       (D) TOPOLOGY: unknown (ii) MOLECULE TYPE: mRNA (xi) SEQUENCE DESCRIPTION: SEQ ID NO: 2:

```
UAGCACCCAC CAAGGCAAAG AGAAGAGUGG UGCAGAGAGA AAAAAGAGCA G UGGGAAUAG      60

GAGCUUUGUU CCUUGGGUUC UUGGGAGCAG CAGGAAGCAC UAUGGGCGCA G CGUCAAUGA     120

CGCUGACGGU ACAUAGUGCU UCCUGCUGUG GAAAGAUACC UAAAGGAUCA A CAGCUCCUG     180

GGGAUUUGGG GUUGCUCUGG AAAACUCAUU UGCACCACUG CUGUGCCUUG G AAUGCUA       238
```

(2) INFORMATION FOR SEQ ID NO: 3:

(i) SEQUENCE CHARACTERISTICS:
       (A) LENGTH: 62 bases
       (B) TYPE: nucleic acid
       (C) STRANDEDNESS: single
       (D) TOPOLOGY: unknown (ii) MOLECULE TYPE: other nucleic acid (xi) SEQUENCE DESCRIPTION: SEQ ID NO: 3:

```
GGCAGACCGG AAUUCUUGGG CGCAGCGUCA UUGACGCUGC GGUACAAGAA U UCCGGUCUG      60

CC                                                                     62
```

(2) INFORMATION FOR SEQ ID NO: 4:

(i) SEQUENCE CHARACTERISTICS:
       (A) LENGTH: 64 bases
       (B) TYPE: nucleic acid
       (C) STRANDEDNESS: single
       (D) TOPOLOGY: unknown (ii) MOLECULE TYPE: other nucleic acid (xi) SEQUENCE DESCRIPTION: SEQ ID NO: 4:

GGCAGACCGG AAUUCUUGGG CGCAGCGUCA UUGACGCUGC GGUACAUCGG A AUUCCGGUC     60

UGCC     64

(2) INFORMATION FOR SEQ ID NO: 5:

(i) SEQUENCE CHARACTERISTICS:
        (A) LENGTH: 62 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 5:

GGCAGACCGG AAUUCUUCGG GGCAGCGUCA UUGACGCUGC CGUAGAAGAA U UCCGGUCUG     60

CC     62

(2) INFORMATION FOR SEQ ID NO: 6:

(i) SEQUENCE CHARACTERISTICS:
        (A) LENGTH: 64 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 6:

GGCAGACCGG AAUUCUUCGG GGCAGCGUCA UUGACGCUGC CGUAGAUCGG A AUUCCGGUC     60

UGCC     64

(2) INFORMATION FOR SEQ ID NO: 7:

(i) SEQUENCE CHARACTERISTICS:
        (A) LENGTH: 62 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 7:

GGCAGACCGG AAUUCUGGGC GCAGCGUCAU UGACGCUGCG GUACAAAGAA U UCCGGUCUG     60

CC     62

(2) INFORMATION FOR SEQ ID NO: 8:

(i) SEQUENCE CHARACTERISTICS:
        (A) LENGTH: 79 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 8:

GGCAGACCGG AAUUCUUGGG CGCAGCGUCA UUGACGCUGC GGUACAGGCC A GAUUAUCUG     60

AUAAGAAUUC CGGUCUGCC     79

(2) INFORMATION FOR SEQ ID NO: 9:

(i) SEQUENCE CHARACTERISTICS:
        (A) LENGTH: 64 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 9:

```
GGCAGACCGG AAUUCUAAUG GGCGCAGCGU CAUUGACGCU GCGGUACAAG A AUUCCGGUC      60

UGCC                                                                   64
```

(2) INFORMATION FOR SEQ ID NO: 10:

(i) SEQUENCE CHARACTERISTICS:
        (A) LENGTH: 62 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 10:

```
GGCAGACCGG AAUUCUGGGC GCAGCGUCAU UGACGCUGCG GUACAGAAAA U UCCGGUCUG      60

CC                                                                     62
```

(2) INFORMATION FOR SEQ ID NO: 11:

(i) SEQUENCE CHARACTERISTICS:
        (A) LENGTH: 62 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 11:

```
GGCAGAAACC GGAAUUCUGG GCGCAGCGUC AUUGACGCUG CGGUACAGAA U UCCGGUCUG      60

CC                                                                     62
```

(2) INFORMATION FOR SEQ ID NO: 12:

(i) SEQUENCE CHARACTERISTICS:
        (A) LENGTH: 64 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 12:

```
GGCAGACCGG AAUUCUGGGC GCAGCGUCAU UGACGCUGCG GUACAAAGAA U UCCAAGGUC      60

UGCC                                                                   64
```

(2) INFORMATION FOR SEQ ID NO: 13:

(i) SEQUENCE CHARACTERISTICS:
        (A) LENGTH: 62 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 13:

GGCAGACCGG AAUUCUCGGU ACACAGCGUC AUUGACGCUG UGGGCGAGAA U UCCGGUCUG        60

CC                                                                       62

(2) INFORMATION FOR SEQ ID NO: 14:

(i) SEQUENCE CHARACTERISTICS:
        (A) LENGTH: 62 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 14:

GGCAGCGGUA CAACCGGAAU UCUCAGCGUC AUUGACGCUG AGAAUUCCGG U UGGGCGCUG        60

CC                                                                       62

(2) INFORMATION FOR SEQ ID NO: 15:

(i) SEQUENCE CHARACTERISTICS:
        (A) LENGTH: 62 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 15:

GGCAGUGGGC GACCGGAAUU CUCAGCGUCA UUGACGCUGA GAAUUCCGGU C GGUACACUG        60

CC                                                                       62

(2) INFORMATION FOR SEQ ID NO: 16:

(i) SEQUENCE CHARACTERISTICS:
        (A) LENGTH: 64 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 16:

GGCAGACCGG AAUUCUCGGU ACACAGCGUC AUUGACGCUG UGGGCGUCGG A AUUCCGGUC        60

UGCC                                                                     64

(2) INFORMATION FOR SEQ ID NO: 17:

(i) SEQUENCE CHARACTERISTICS:
        (A) LENGTH: 79 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 17:

GGCAGACCGG AAUUCUCGGU ACACAGCGUC AUUGACGCUG UGGGCGGGCC A GAUUAUCUG        60

AUAAGAAUUC CGGUCUGCC                                                     79

(2) INFORMATION FOR SEQ ID NO: 18:

(i) SEQUENCE CHARACTERISTICS:
        (A) LENGTH: 53 bases
        (B) TYPE: nucleic acid
        (C) STRANDEDNESS: single
        (D) TOPOLOGY: unknown (ii) MOLECULE TYPE: mRNA (xi) SEQUENCE DESCRIPTION: SEQ ID NO: 18:

```
CUGCGGAGAG GCUGGCAGAU UGAGCCCUGG GAGGUUCUCU CCAGCACUAG C AG          53
```

(2) INFORMATION FOR SEQ ID NO: 19:

(i) SEQUENCE CHARACTERISTICS:
        (A) LENGTH: 24 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 19:

```
CUGAUGAGUC CGUGAGGACG AAAC                                           24
```

(2) INFORMATION FOR SEQ ID NO: 20:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

```
TTTATCGACT ACACTATAG                                                 19
```

(2) INFORMATION FOR SEQ ID NO: 21:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 21:

```
ACCNNNNNNG GT                                                        12
```

(2) INFORMATION FOR SEQ ID NO: 22:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 22:

```
ACCGTTGCCG GT                                                        12
```

(2) INFORMATION FOR SEQ ID NO: 23:

(i) SEQUENCE CHARACTERISTICS:
        (A) LENGTH: 33 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 23:

```
Lys Ala Val Lys Pro Lys Ala Ala Lys Pro L ys Lys Pro Lys Lys Lys
1               5                   10                  15
Arg Lys Val Glu Lys Lys Ser Pro Lys A la Lys Lys Pro Ala Ala
                20                  25                  30
Cys
```

(2) INFORMATION FOR SEQ ID NO: 24:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 24:

```
Lys Lys Ser Pro Lys Lys Ala Lys Lys Pro A la Ala Lys Lys Ser Pro
1               5                   10                  15
Lys Lys Ala Lys Lys Pro Ala Ala Cys
                20                  25
```

(2) INFORMATION FOR SEQ ID NO: 25:

(i) SEQUENCE CHARACTERISTICS:
        (A) LENGTH: 37 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 25:

```
Lys Lys Ser Pro Lys Lys Ala Lys Lys Pro A la Ala Lys Lys Ser Pro
1               5                   10                  15
Lys Lys Ala Lys Lys Pro Ala Ala Lys Lys S er Pro Lys Lys Ala Lys
                20                  25                  30
Lys Pro Ala Ala Cys
        35
```

(2) INFORMATION FOR SEQ ID NO: 26:

(i) SEQUENCE CHARACTERISTICS:
        (A) LENGTH: 49 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 26:

```
Lys Lys Ser Pro Lys Lys Ala Lys Lys Pro A la Ala Lys Lys Ser Pro
1               5                   10                  15
Lys Lys Ala Lys Lys Pro Ala Ala Lys Lys S er Pro Lys Lys Ala Lys
                20                  25                  30
```

```
Lys Pro Ala Ala Lys Lys Ser Pro Lys Ala Lys Lys Pro Ala Ala
        35                  40                  45
Cys
```

(2) INFORMATION FOR SEQ ID NO: 27:

(i) SEQUENCE CHARACTERISTICS:
        (A) LENGTH: 31 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 27:

```
Thr Arg Arg Ala Trp Arg Arg Ala Lys Arg Arg Ala Ala Arg Arg Cys
1               5                   10                  15
Gly Val Ser Ala Arg Arg Ala Ala Arg Arg Ala Trp Arg Arg Glu
            20                  25                  30
```

(2) INFORMATION FOR SEQ ID NO: 28:

(i) SEQUENCE CHARACTERISTICS:
        (A) LENGTH: 31 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 28:

```
Thr Lys Lys Ala Trp Lys Lys Ala Glu Lys Lys Ala Ala Lys Lys Cys
1               5                   10                  15
Gly Val Ser Ala Lys Lys Ala Ala Lys Lys Ala Trp Lys Lys Ala
            20                  25                  30
```

(2) INFORMATION FOR SEQ ID NO: 29:

(i) SEQUENCE CHARACTERISTICS:
        (A) LENGTH: 70 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 29:

```
AATTCGGCAG ACCGGAATTC TTGGGCGCAG CGTCATTGAC GCTGCGGTAC ATCGGAATTC    60
CGGTCTGCCC                                                          70
```

(2) INFORMATION FOR SEQ ID NO: 30:

(i) SEQUENCE CHARACTERISTICS:
        (A) LENGTH: 66 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 30:

```
GGGCAGACCG GAATTCCGAT GTACCGCAGC GTCAATGACG CTGCGCCCAA GAATTCCGGT    60
CTGCCG                                                              66
```

(2) INFORMATION FOR SEQ ID NO: 31:

(i) SEQUENCE CHARACTERISTICS:
        (A) LENGTH: 85 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 31:

```
AATTCGGCAG ACCGGAATTC TTGGGCGCAG CGTCATTGAC GCTGCGGTAC A GGCCAGATT        60

ATCTGATAAG AATTCCGGTC TGCCC                                              85
```

(2) INFORMATION FOR SEQ ID NO: 32:

(i) SEQUENCE CHARACTERISTICS:
        (A) LENGTH: 81 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 32:

```
GGGCAGACCG GAATTCTTAT CAGATAATCT GGCCTGTACC GCAGCGTCAA T GACGCTGCG        60

CCCAAGAATT CCGGTCTGCC G                                                  81
```

(2) INFORMATION FOR SEQ ID NO: 33:

(i) SEQUENCE CHARACTERISTICS:
        (A) LENGTH: 33 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 33:

```
AGCTTACGAT CGACCGCGGA GCGGCCGCAG GGC                                     33
```

(2) INFORMATION FOR SEQ ID NO: 34:

(i) SEQUENCE CHARACTERISTICS:
        (A) LENGTH: 33 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 34:

```
AGCTGGGCCC TGCGGCCGCT CCGCGGTCGA TCG                                     33
```

(2) INFORMATION FOR SEQ ID NO: 35:

(i) SEQUENCE CHARACTERISTICS:
        (A) LENGTH: 28 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 35:

```
CGGCGGTGAA TTCGTCGCTC TGCGGAGA                                           28
```

(2) INFORMATION FOR SEQ ID NO: 36:

(i) SEQUENCE CHARACTERISTICS:
        (A) LENGTH: 28 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 36:

```
TGGAATTCGG CCGACCGGCC AAGTGCTG                                    28
```

(2) INFORMATION FOR SEQ ID NO: 37:

(i) SEQUENCE CHARACTERISTICS:
        (A) LENGTH: 30 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 37:

```
CGGGATCCGT CGACCTAGAC TAGAGCCCTG                                  30
```

(2) INFORMATION FOR SEQ ID NO: 38:

(i) SEQUENCE CHARACTERISTICS:
        (A) LENGTH: 24 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 38:

```
GCGAATTCAA TAGCAATTGG TACA                                        24
```

(2) INFORMATION FOR SEQ ID NO: 39:

(i) SEQUENCE CHARACTERISTICS:
        (A) LENGTH: 30 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 39:

```
CGGATCCGTC GACGGCGTTA CTCGACAGAG                                  30
```

(2) INFORMATION FOR SEQ ID NO: 40:

(i) SEQUENCE CHARACTERISTICS:
        (A) LENGTH: 25 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 40:

```
CCGAATTCGG CTTTTGTTAT GAAAC                                       25
```

-continued (2) INFORMATION FOR SEQ ID NO: 41:

(i) SEQUENCE CHARACTERISTICS:
        (A) LENGTH: 16 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 41:

AAACGATCGA AGAGCT                         16

(2) INFORMATION FOR SEQ ID NO: 42:

(i) SEQUENCE CHARACTERISTICS:
        (A) LENGTH: 16 bases
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 42:

CTTCGATCGT TTAGCT                         16

(2) INFORMATION FOR SEQ ID NO: 43:

(i) SEQUENCE CHARACTERISTICS:
        (A) LENGTH: 162 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 43:

GGATCCTGAG AACTTCAGGG TGAGTCTATG GGACCCTTGA TGCCCGGGTA C AGTCCAAGC    60

TAGGCCCTTT TGCTAATCAT GTTCATACCT CTTATCTTCC TCCCACAGCT C CTGGGCAA    120

GTGCTGGTCT GTGTGCTGGC CCATCACTTT GGCAAAGAAT TC    162